US012453829B2

(12) United States Patent
Kim

(10) Patent No.: US 12,453,829 B2
(45) Date of Patent: Oct. 28, 2025

(54) MULTIPURPOSE AIRWAY DEVICE

(71) Applicant: Chong S. Kim, Holmdel, NJ (US)

(72) Inventor: Chong S. Kim, Holmdel, NJ (US)

( * ) Notice: Subject to any disclaimer, the term of this patent is extended or adjusted under 35 U.S.C. 154(b) by 791 days.

(21) Appl. No.: 17/752,758

(22) Filed: May 24, 2022

(65) Prior Publication Data

US 2022/0280737 A1 Sep. 8, 2022

Related U.S. Application Data

(63) Continuation-in-part of application No. 17/110,268, filed on Dec. 2, 2020, now Pat. No. 11,793,962.

(51) Int. Cl.

| | |
|---|---|
| ***A61M 16/04*** | (2006.01) |
| ***A61B 1/00*** | (2006.01) |
| ***A61B 1/005*** | (2006.01) |
| ***A61B 1/018*** | (2006.01) |
| ***A61B 1/267*** | (2006.01) |
| ***A61B 1/32*** | (2006.01) |
| ***A61M 16/00*** | (2006.01) |

(52) U.S. Cl.

CPC .... *A61M 16/0409* (2014.02); *A61M 16/0434* (2013.01); *A61M 16/0463* (2013.01); *A61M 16/0484* (2014.02); *A61M 16/0486* (2014.02)

(58) Field of Classification Search

CPC .......... A61M 16/0409; A61M 16/0488; A61M 16/0459; A61M 16/04; A61M 16/0434; A61M 16/0456; A61B 1/267–2676; A61B 1/32; A61B 1/00135

See application file for complete search history.

(56) References Cited

U.S. PATENT DOCUMENTS 2,541,402 A 2/1951 Caine
3,802,440 A 4/1974 Ziegler et al.
(Continued)

FOREIGN PATENT DOCUMENTS

EP 0448878 A2 10/1991
GB 2478988 A 9/2011
(Continued)

*Primary Examiner* — Kendra D Carter
*Assistant Examiner* — Mautin I Ashimiu
(74) *Attorney, Agent, or Firm* — Jessica Smith; LOZA & LOZA, LLP

(57) ABSTRACT

An airway device facilitates the insertion of an ETT into a patient, the delivery of oxygenated air into a patient, an exchange of the pre-inserted ETT in an intubated patient, and an evaluation of the larynx and trachea in an intubated patient, The device comprises an overtube having a mask section attached to a distal portion of the overtube. An inflatable bladder affixed to the mask section includes a shape and surface configured to seamlessly contact the circumference of the elliptical construction of the laryngeal opening. Once the inflatable bladder is positioned adjacent the laryngeal opening enhanced sealing properties are created so that the axis of the airflow entering the device matches the axis of the trachea, allowing for the improved delivery of oxygenated air into the patient's lungs. The specific utilization of the bladder allows for the device to be constructed smaller than a typical airway device, which may more easily facilitate the insertion process. Additionally, the device may provide a seamless transition into endotracheal intubation when necessary.

24 Claims, 39 Drawing Sheets

(56) References Cited

U.S. PATENT DOCUMENTS

| | | | |
|---|---|---|---|
| 4,329,983 | A | 5/1982 | Fletcher |
| 4,685,457 | A | 8/1987 | Donenfeld |
| 4,832,020 | A | 5/1989 | Augustine |
| 4,840,172 | A | 6/1989 | Augustine et al. |
| 5,038,766 | A | 8/1991 | Parker |
| 5,042,469 | A | 8/1991 | Augustine |
| 5,174,283 | A | 12/1992 | Parker |
| 5,203,320 | A | 4/1993 | Augustine |
| 5,443,063 | A | 8/1995 | Greenberg |
| 5,743,258 | A | 4/1998 | Sato et al. |
| 5,873,362 | A | 2/1999 | Parker |
| 5,896,858 | A | 4/1999 | Brain |
| 6,443,156 | B1 | 9/2002 | Niklason et al. |
| 6,543,447 | B2 | 4/2003 | Pacey |
| 6,722,368 | B1 | 4/2004 | Shaikh |
| 6,729,325 | B2 | 5/2004 | Alfery |
| 6,761,170 | B2 | 7/2004 | Van Landuyt |
| 7,013,890 | B2 | 3/2006 | Wakabayashi |
| 7,013,899 | B2 | 3/2006 | Alfery et al. |
| 7,040,312 | B2 | 5/2006 | Alfery et al. |
| 7,040,322 | B2 | 5/2006 | Fortuna |
| 7,159,589 | B2 | 1/2007 | Brain |
| 7,896,007 | B2 | 3/2011 | Brain |
| 9,038,636 | B2 | 5/2015 | Baska |
| 9,199,051 | B2 | 12/2015 | Booth |
| 9,750,912 | B2 | 9/2017 | McCormick et al. |
| 9,770,567 | B2 | 9/2017 | Baska |
| 9,937,311 | B2 | 4/2018 | Jassell et al. |
| 9,956,367 | B1 | 5/2018 | Sun |
| 9,974,912 | B2 | 5/2018 | Brain |
| 10,188,815 | B2 | 1/2019 | Sagales et al. |
| 10,307,043 | B2 | 6/2019 | Rutgers |
| 10,314,995 | B2 | 6/2019 | Sun |
| 10,426,908 | B1 | 10/2019 | Annis |
| 10,434,272 | B1 | 10/2019 | Annis |
| 10,478,054 | B2 | 11/2019 | Nave et al. |
| 10,478,576 | B2 | 11/2019 | Baska |
| 10,556,077 | B2 | 2/2020 | Avitsian et al. |
| 10,576,229 | B2 | 3/2020 | Brain |
| 10,639,443 | B2 | 5/2020 | Avitsian et al. |
| 10,702,665 | B2 | 7/2020 | Gardner |
| 10,980,955 | B2 | 4/2021 | Nawn et al. |
| 11,051,682 | B2 | 7/2021 | Molnar |
| 2003/0062039 | A1 | 4/2003 | Sniadach |
| 2003/0225432 | A1 | 12/2003 | Baptiste et al. |
| 2004/0020491 | A1* | 2/2004 | Fortuna ............. A61M 16/0486 128/200.26 |
| 2005/0256452 | A1 | 11/2005 | DeMarchi et al. |
| 2007/0106121 | A1 | 5/2007 | Yokota et al. |
| 2008/0099026 | A1 | 5/2008 | Chang |
| 2008/0257356 | A1 | 10/2008 | Swick |
| 2009/0000622 | A1* | 1/2009 | Murray ............. A61M 16/0459 128/200.26 |
| 2009/0090356 | A1 | 4/2009 | Cook |
| 2009/0192350 | A1 | 7/2009 | Mejia |
| 2010/0249639 | A1 | 9/2010 | Bhatt |
| 2011/0277772 | A1 | 11/2011 | Nasir |
| 2012/0073572 | A1 | 3/2012 | Li |
| 2013/0220332 | A1 | 8/2013 | Baska et al. |
| 2013/0237763 | A1 | 9/2013 | Qiu |
| 2014/0000624 | A1 | 1/2014 | Miller |
| 2014/0014114 | A1 | 1/2014 | Miller |
| 2020/0030575 | A1 | 1/2020 | Bogusky et al. |
| 2020/0147331 | A1 | 5/2020 | Viren |
| 2020/0375448 | A1 | 12/2020 | Hartley et al. |
| 2021/0162154 | A1 | 6/2021 | Sun |

FOREIGN PATENT DOCUMENTS

| | | | |
|---|---|---|---|
| WO | 1998023317 | A1 | 6/1998 |
| WO | 2010017685 | A1 | 2/2010 |
| WO | 2012164532 | A1 | 12/2012 |
| WO | 2016147107 | A1 | 9/2016 |
| WO | 2018112057 | A1 | 6/2018 |

* cited by examiner

METHOD 1400

MULTIPURPOSE AIRWAY DEVICE

CROSS-REFERENCE TO RELATED APPLICATIONS

This application is a continuation-in-part application of currently pending U.S. patent application Ser. No. 17/110,268, filed Dec. 2, 2020, which is incorporated by reference in its entirety herein.

FIELD OF THE INVENTION

The present invention relates to airway devices, and more specifically to an airway management system and methods that facilitate the exposure and evaluation of the larynx and the trachea and that further facilitate various internal medical processes/procedures within a patient.

BACKGROUND OF THE INVENTION

The most effective and basic way of securing definitive airway management remains direct laryngoscopy with subsequent placement of an endotracheal tube. A laryngoscope consists of a handle and a blade. The blade of a laryngoscope is typically comprised of a flat element (usually made of stainless steel) and is designed to be placed either in the vallecula (behind the tongue) or posterior to the epiglottis. By lifting up an inserted laryngoscope, the mandible, tongue, epiglottis, hyoid bone, and other soft tissue are displaced out of the line of sight of the laryngoscopist in order to expose the glottic opening.

The success of intubation is dependent upon being able to clearly expose the laryngeal opening. A generally accepted way to improve a limited laryngeal opening includes increasing elevation of the patient's head and placing the patient in a "sniff" position, which involves extending the atlanto-occipital joint and flexing the lower cervical spine. In cases where cervical immobilization is necessary (e.g., trauma involving possible cervical spine injury), head elevation and cervical spine manipulation are not permitted. While the majority of cases of intubations are straightforward and simple, difficulty in airways do occur and can result in catastrophic outcomes such as death, brain damage, cardiopulmonary arrest, tracheotomy, and trauma to the pharynx, larynx, and trachea.

There are many causes of difficult intubation: a small mouth, recessed mandible, prominent upper teeth, limited upper cervical spine or atlanto-occipital mobility, limited jaw opening, enlarged tongue, tumors (in the mouth, tongue, larynx, and/or pharynx), obesity with redundant soft tissue, and edema (of the epiglottis, larynx, and/or pharynx).

Tracheal intubation involves placing a flexible plastic tube into the trachea as a conduit to supply oxygen to and eliminate carbon dioxide from a patient. Tracheal intubation is frequently performed for patients that are critically injured, ill, or who require anesthesia. Optimal visualization of the laryngeal opening is best achieved by extending the head and flexing the neck, which is known as a "sniffing position".

Successful intubation requires two distinct processes: 1) clear visualization and identification of the vocal cords and 2) proper insertion of an endotracheal tube into the trachea. These two processes are equally important. Achieving the first step is of great importance because when the patient is placed under general anesthesia and given paralytic agents, all of the laryngopharyngeal structures become flaccid and collapse, resulting in complete blockage of the airway. During intubation, the operator has to first "clear" the blockage before inserting an ETT. The performance of the second step can be demanding and requires skill and experience. If the former step fails, this is a situation referred to as "can't see and can't intubate." If the latter process fails, this is referred to as "can see but can't intubate."

Proper visualization and identification of the vocal cords is commonly aided by a rigid laryngoscope (which consists of a handle containing batteries that power the light and a rigid and flat blade which is either straight or curved) that is the primary equipment to aid intubation. During intubation, the laryngoscope blade is inserted through the mouth of the patient and positioned in the vallecula (the area between the base of the tongue and the epiglottis that is configured as oval shaped structure located on top of the larynx) the blade acts as a lid over the laryngeal vestibule that opens into the larynx to prevent the passage of food into the trachea during eating. Once properly placed, the laryngoscope is then pulled anteriorly in an effort to displace the tongue and epiglottis in the upward direction to permit direct visualization of the laryngeal opening.

While its usefulness is unquestioned, rigid laryngoscopes, nonetheless, are not without shortcomings. By virtue of the laryngoscope blades being made of hard metal, traumatic injury to dental structures and soft tissues in the oral cavity and the pharynx are not uncommon. In order to mitigate intubation-related injuries, there exists a need for an approach or a device that is capable of supplanting rigid laryngoscopes without compromising results.

As alluded to earlier, one of the main functions of rigid laryngoscopes is the displacement of the tongue and the epiglottis from the operator's line of vision. Whilst laryngoscopes are adequate in certain cases, they frequently, however, fail simply because they only expose the airway to the level of the epiglottis and not beyond. Should narrowing, swelling, or excessive soft tissue exist below the level of the epiglottis, the usefulness of rigid laryngoscopes is severely limited. Likewise, its utility is restricted in the presence of factors such as a large tongue, large tumors in the oral cavity or oropharynx, an edematous tongue, a receded chin, an immobile jaw, elongated upper incisors, a stiff and immobile neck, and facial and neck trauma. In this regard, the development of video laryngoscopes has made an enormous contribution in the betterment of the operator's visualization of the larynx. Video laryngoscopes are distinguished from traditional laryngoscopes by having a camera and light installed at the tip of the blade. The presence of the camera at the tip allows the user to inspect the anatomy from the vantage point of the blade tip. It is analogous to having an eye at the tip of the blade. Notwithstanding these advantages, challenges still remain due to the blade of the video laryngoscope being ordinarily positioned at the vallecula (the point between the base of the tongue and the epiglottis). In situations where blockage is present beyond the laryngeal blade (i.e. between the tongue base and the vocal cords), video laryngoscopes are inadequate and cannot better the visualization of the laryngeal opening.

Currently, a solution is needed that proffers methods and/or means that can assist in surmounting the challenges of exposing the vocal cord when obstructive pathology (such as excessive soft tissue, tumor, infection, edema, and hematoma) exists between the epiglottis and the larynx.

One skilled in art may recognize that the path an ETT (endotracheal tube) takes, rather than being straight, is very much convoluted. In understanding the convoluted pathway an ETT traverses, it is helpful to divide the pathway into three segments: the first segment (from the mouth opening to the posterior pharynx), the second segment (from the pharynx to the base of the epiglottis), and the third segment (from the base of the epiglottis to the trachea through the larynx). Two approximately 90-degree bends exist, with the first being between the first and second segments and the second between the second and third segments. The overall trajectory of an ETT, then, is shaped like an S with two sharp turns.

Recognizing the complex nature of the ETT path, an operator, before intubating, may manually shape the endotracheal tube by means of a rigid malleable stylet, which is placed inside the ETT. Commonly, the stylet is bent approximately 90 degrees at the junction between the middle and distal one third segments (presented above). The fashioned ETT now has a built-in first pivot, facilitating the operator to advance the ETT through the first and second segments. If problems arising in this phase of intubation can be managed with relative ease, the next phase of intubation (navigating the ETT through the second pivot point) can be more daunting.

An important issue with intubation that cannot be ignored is the need to quickly intubate the patient. There are countless situations where seconds of oxygen deprivation matter to the well-being of the patient. In the cases of difficult airways, it is not uncommon for the operator to take a significant amount of time to intubate. Because the oxygen is held during the intubation process, the patient may suffer from hypoxia.

Another vital aspect of intubation is the existence of technical limitations that force the operator to stop oxygenation during intubation. The most important factors include: presence of a stylet inside the full length of the ETT, inability to control oxygen escaping out of the mouth, and ineffectual means of preventing the air diverted into the stomach. For these reasons, supplying oxygen ceases during the entire duration of intubation. When the patient's blood oxygen level drops to a significant level, the intubation process has to stop immediately. The next intubation attempt can commence only when the patient's oxygen level is raised to a satisfactory level. A repeated stop and go cycle can be frustrating and can reduce the likelihood of successful intubation, not to mention the potential adverse impact on the patient.

Supraglottic airway devices (known as SGAs or SADs) are an important group of devices that assist in providing oxygenated air to unconscious or anesthetized patients. SGAs generally consist of a tube attached to an inflatable, elliptical mask. The mask is typically a flattened, pear-shaped, inflatable cuff with an open front. It is widely taught that when properly positioned, the opening of an SGA overlies the glottis, the proximal end of the SGA opposes the base of the tongue, and the distal rim wedges against the upper esophageal sphincter, making a seal. They are designed to be inserted blindly through the mouth and into the hypopharynx. When deployed, SGAs facilitate oxygen delivery into the lungs and are a useful alternative to the traditional airway known as the endotracheal tube (ETT).

Endotracheal tubes comprise a long slender tubular body with an inflatable balloon disposed at the tube's distal end. When intubating a patient, the endotracheal tube's distal end is inserted through the mouth of the patient, past the patient's laryngeal inlet (or glottic opening), and into the patient's trachea. Once properly positioned within the trachea, the balloon is inflated to form a seal with the interior lining of the trachea.

Although they have been enormously successful for many decades, endotracheal tubes suffer from several major disadvantages. According to T. M. Cook, N. Woodall, C. Frerk in "Major complications of airway management in the UK: results of the Fourth National Audit Project of the Royal College of Anaesthetists and the Difficult Airway Society. Part 1: Anaesthesia," (British Journal of Anaesthesia, vol. 106, no. 5, pp. 617-631, 2011), the principal disadvantage of the endotracheal tube relates to the difficulty of properly inserting the tube. Inserting an endotracheal tube into a patient is a procedure that requires a high degree of skill. Even for skilled practitioners, insertion of an endotracheal tube is sometimes difficult or not possible. In many instances, the difficulty of inserting endotracheal tubes has tragically resulted in the deaths or permanent brain injuries of patients.

There are additional disadvantages associated with endotracheal tubes as well. Endotracheal tubes may cause at least one of the following: postintubation sore throats, bronchospasms, laryngospasms, vocal cord injuries, tracheal mucosal injuries, and arytenoid dislocations. While some of these problems are minor or temporary, others can be permanent or life-threatening. Another disadvantage with endotracheal tubes is that the insertion of an endotracheal tube requires manipulations of the patient's head and neck. These necessary manipulations, however, may be difficult or contraindicated in some patients, thus rendering successful intubation difficult or even impossible.

In contrast to the endotracheal tube, SGAs provide an invaluable alternative. Compared to the endotracheal tube, it is relatively easy to insert SGAs into a patient to establish an airway. SGAs are considered a more "forgiving" device in that even if the SGA is inserted improperly, it still tends to establish an airway. Accordingly, SGAs are often thought of as a "life-saving" device. SGAs, in addition, may be inserted with relatively minor manipulations of the patient's head, neck, and jaw (unlike endotracheal tubes). Furthermore, since SGAs do not require contact with the trachea, postintubation complications are significantly less common.

Due to these advantages, SGAs have enjoyed increasing popularity over the last thirty years. The 4th National Audit Project (NAP4, previously presented) conducted in the United Kingdom estimated that 56% of general anesthetics performed were carried out using SGAs to manage the airway. Within the art, SGAs are a preferred mode of use for anesthesia related medical procedures, particularly in cases less than two hours in duration.

Notwithstanding the popularity, SGAs can have many drawbacks. According to Michalek, P., Donaldson, W., Vobrubova, E., & Hakl, M. (2015) in "Complications Associated with the Use of Supraglottic Airway Devices in Perioperative Medicine." (BioMed research international, 2015, 746560), difficulty inserting an SGA into a patient's throat, among the many disadvantages of SGAs, is the greatest concern to a clinician. When a patient is in respiratory distress, being able to establish an airway promptly without any delay is paramount. If an SGA cannot be inserted with facility, the results can be dire. It is noted that the feature that makes it difficult for an SGA to be inserted easily, besides its bulkiness, is its configuration.

To better understand the problems with SGAs, it is necessary to recognize that during an intubation process, the SGA travels a convoluted path: it travels from the lips posteriorly straight to the posterior oropharyngeal wall, at which point, it heads down into the hypopharynx. After the bend at the posterior pharyngeal wall, the mask portion of the SGA will tend to proceed anteroinferiorly from the posterior oropharyngeal wall. Naturally, then, the mask will end up in the larynx, being that it is located anterior to the hypopharyngeal wall, which is undesirable. Instead, it is necessary to force the SGA mask to advance it inferiorly only. Thus, a unique configuration of SGAs is needed in order to make it easier to introduce SGAs into a patient. Since the introduction of the first SGAs in the early 1990s, SGAs have undergone numerous modifications in terms of design and functionality. In fact, at the present, there are more than 20 different SGAs available in the commercial market.

The facility with which an SGA is able to be inserted is related principally to its bulkiness and profile. Most of the SGAs that exist today are rather large and have a thick profile such that inserting them into a patient poses no small challenge. Part of the reasons for the SGAs' unwieldiness is related to their need to produce a non-leaking seal since the mask cuffs are designed to obstruct the large space that exists in the oropharynx and the hypopharynx. Improvements can be made if the sealing site is more focused and anatomically sound. More specifically, it is asserted that sealing just the inlet of the larynx would be an improvement from previous SGAs. The inlet of the larynx consists of the mid-portion of the epiglottis anteriorly, aryepiglottic (AE) folds laterally, and arytenoids posteriorly. The inlet takes on an elliptical shape measuring roughly 8-24 millimeters in the anterior-posterior direction and 10-24 millimeters along the transverse axis. Anteriorly, the aryepiglottic folds meet the epiglottis on the side, and not the superior tip, at an angle slightly larger than 90 degrees. This important anatomical fact is completely ignored by most SGAs as their masks are smooth-surfaced. The smooth masks do not squarely seal the angulated epiglottis and AE fold junction.

An additional weakness of the prior art is that the proximal aspect of the mask/cuff is designed to make contact with the superior tip of the epiglottis, which is a specific portion of the epiglottis that is free-floating and does not rest against any firm structures. As such, the mask/cuff resting against the top of the epiglottis is an ineffective means to obtain an effective seal. Moreover, all SGAs that produce a seal in this manner run the risk of applying pressure over the tip of the hyoid bone, which is in very close proximity to the hypoglossal nerve, making the nerve vulnerable to injury.

The crux of the problem, therefore, is a lack of anatomical understanding. United States patent application number US20190160243A1, entitled "Laryngeal mask cuff", recognized the need for more localized sealing focusing on the inlet of the larynx and not the entire space of the oropharynx and hypopharynx. However, the disclosure failed to teach an effective means. Therefore, there is still a gap in the art that needs to be filled concerning more precise and effective localized sealing. Prior art, furthermore, fails to address the issue of directing airflow preferentially toward the trachea. Anyone skilled in art would recognize the importance of this matter. It is noted that most of the prior art includes airway openings near the laryngeal inlet without any means of directing the airflow. These devices would, therefore, allow only a small fraction of the air to be directed toward the trachea, highlighting another disadvantage of the state of the art of SGAs.

Furthermore, an ideal SGA must allow easy conversion into endotracheal intubation. There can be diverse situations where this is not only desirable but paramount. A surgical case may begin with an SGA, but in mid-course, the nature of the case may change and endotracheal intubation may then be required. Also, a patient's clinical status may suddenly deteriorate on an SGA, so inserting an endotracheal tube becomes essential. Transitioning from an SGA to an ETT should ideally be so facile and seamless that it does not cause substantial disruptions to a progressing surgery. U.S. Pat. No. 5,303,697A, entitled "Artificial airway device", teaches a means to insert an ETT through an SGA. What is actually taught, however, is a method of inserting an ETT blindly. While the effort is laudable, blindly inserting a breathing tube is not only inadvisable but it can cause life-threatening complications for a patient. With other SGAs, before an ETT can be inserted, the SGA has to be completely removed from the body. A device that does not need to be removed before insertion of an ETT and that includes the following characteristics, is needed in the art; characteristics include: easy insertion, creation of an anatomically focused seal without exerting excessive pressure, properly directed airflow toward the trachea, and easy conversion to endotracheal intubation.

During the course of caring for an intubated patient, there may come a time (due to tube obstruction, improper size, malfunctioning tube, etc.) where it is necessary to remove the existing breathing tube and insert an entirely new endotracheal tube in the patient. At present, the usual practice is to remove the old tube and re-intubate with a new tube. The problem is that when the old tube is removed, the physician loses, (possibly up to a few minutes) control of the airway of the patient. If the patient is not reintubated successfully in a short amount of time, the patient's life starts to become in danger.

Additionally, the examination of the larynx and/or trachea of an intubated patient may be invaluable when dealing with the process of extubation. Extubation is a process in which an endotracheal tube (ETT) is removed from a patient's airway. The process is performed when the patient is no longer in need of an ETT and usually occurs in the operating room or in the intensive care unit. In practice, while the majority of patients do well after extubation, a surprising number of patients fail, requiring re-intubation; in fact, the incidence of required reintubation in the ICU is on the order of 6 to 25 percent. At present, there is no consensus among airway experts what the best clinical predictors of successful extubation are. At the same time, the same experts agree that the ability to visualize the larynx and assess its function can be invaluable to reduce the rate of "failed extubation." A fiberoptic evaluation tool, a potential tool available today, however, is severely limited, if not useless, due to the ETT blocking the core structures of the larynx. Thus, an effective means of visualizing the larynx in intubated patients is needed.

BRIEF SUMMARY OF THE INVENTION

The disclosed subject matter provides a system, method, and device utilized to introduce an ETT (endotracheal tube) into a trachea of a patient. The device comprises an overtube having a semirigid proximal portion, a flexible distal tip, and a hood. The semirigid portion includes a proximal end and a distal end. The flexible tip affixes to the distal end of the semirigid portion. The distal end may house a feeder mechanism for displacing the ETT. A hood slideably attached to the distal end of the overtube includes a stem, a base, an esophageal seal, and an expandable body. Expansion of the hood body may advance the overtube and place the flexible tip in an optimal location (i.e. at the laryngeal opening) with the ETT in alignment with the tracheal axis. An actuation module actuates the wire-controlled flexible tip of the overtube in order to fine tune the positioning of the flexible tip for arrival at its ultimate position. The ETT may be advanced into the trachea by a plurality of means.

In embodiments, the feeder mechanism may include a first roller and a second roller. The first roller may be laterally displaced by the actuation module towards the second roller in order to retain the ETT. Actuation module may control at least one of a screw mechanism and a spring mechanism that displaces the first roller. Once displaced, at least one of the first and second rollers may be actuated by the actuation module in order to feed the ETT through the flexible tip.

Actuation module, in other embodiments, may control a plurality of wires affixed to the flexible tip of the overtube. The wires may be extended and retracted by actuation module in order to articulate the flexible tip of the overtube. Flexible tip may articulate at least 30 degrees in at least one of a vertical direction and a horizontal direction in response to the extension and retraction of the plurality of wires.

A method is provided for positioning an ETT adjacent a patient's laryngeal opening and inserting an ETT into a patient's trachea. The method includes inserting the device, with an ETT positioned within an overtube, into a patient's throat. The attachment between the hood and the overtube may be unlocked, allowing the overtube to slide/advance within the hood. The expandable hood body is then expanded. Since the anteroinferior portion of the hood body and the distal portion of the overtube are connected, the expandable hood body pulls the overtube anteroinferiorly. An alternative directional wire originating from the anteroinferior portion of the hood body affixed to the distal end of the overtube, when triggered, pulls the overtube adjacent the laryngeal opening. The end result of this positioning motion is the placement of the overtube and the ETT at the opening of the larynx. Thusly positioned overtube may be further adjusted via articulating functionality of the flexible portion of the overtube. The ETT may be advanced into the trachea through a plurality of means.

An additional embodiment provides an airway device including an inflatable bladder with an adaptable construction for delivering oxygenated air into a patient. The device may additionally facilitate the exposure of the larynx and the trachea, deliver oxygenated air into a patient, enable an exchange of the pre-inserted ETT in an intubated patient, and enable an evaluation of the larynx and trachea in an intubated patient. The device comprises an overtube having a proximal end and a distal end. A mask section attached to the distal end of the overtube includes a spine section, an expandable body disposed on a proximal portion of the spine section, an inflatable bladder, and an esophageal obdurator disposed a distal section of the spine section. The expandable body includes a sheath and a tunnel. A sheath of the expandable body spans along the spine section from the inlet portion to the inflatable bladder to create a sealed environment between the inlet portion, the inflatable bladder, and the spine section. A tunnel section disposed within the sheath extends from the inlet portion to the inflatable bladder to create a sealed connection between the inlet portion and the inflatable bladder within the sheath. Via the air-tight sealing means of a sheath and a tunnel section, the expandable body is made reversibly inflatable. When deflated, the volume of the expandable body becomes minimal which facilitates the insertion of the device into the patient. The inflating bladder is a torus with a hole in the middle and a circular or ellipsoid ring in the periphery (the position and the placement of the inflating bladder may be more precisely described by utilizing the terminology and system defined in the Standard Automotive Engineering (SAE) J670). The inflating bladder is structured to connect to the spine section with the "tire plane" of the inflating bladder at an angle larger than 90 degrees to the dorsal surface of the spine section. The inclination angle of the inflating bladder may be 1 degree to 45 degrees. The inflating bladder's longitudinal axis is aligned parallel to the transverse axis of a patient. The mask section is configured for sealing engagement with a laryngeal opening of the patient to create an unobstructed path into the trachea of the patient. Additionally, the distal end of the spine section includes an esophageal obturator that protrudes from the distal end of the spine section. The entire length of the spine section is gently curved whose curvature is defined by a radius and the center, which is located on the posterior aspect of the spine section. Thus, the convex surface of the spine section faces in the anterior direction. This novel configuration allows the distal tip of the spine section, during the insertion process, to be positioned posterior to the mid-point of the same, and thus preferentially guides the esophageal obdurator into the hypopharynx/proximal esophagus. Incorporated within a part or the whole length of the spine section may be a stent or reinforcing material to provide further rigidity to the spine section. Once lodged in the esophagus of the patient, an inflated inflatable esophageal obturator cuff affixed to a distal end of the esophageal obturator is configured to securely lodge the esophageal obturator in the hypopharynx/proximal esophagus of the patient.

An additional embodiment provides a mask section for an airway device. The mask section includes a spine section and an expandable body disposed on a distal portion of the overtube, an inflating bladder, and an esophageal obdurator. The expandable body includes a sheath and a tunnel both of which joins an inlet portion of the mask proximally, the spine section posteriorly, and an inflating bladder distally. A tunnel section disposed within the sheath extends from the inlet portion to the inflatable bladder to create a sealed engagement between the inlet portion and the inflatable bladder. The inflating bladder is shaped like a torus with a circular or ellipsoid inflatable ring. It may be in an inflated or deflated state. The inflating bladder positioned a distance from the inlet portion is connect to the spine section with the "tire plane" (as defined in SAE J670) of the inflating bladder at an angle larger than 90 degrees to the dorsal surface of the spine section. The inclination angle of the inflating bladder may be 1 degree to 45. In the deflated state, the inflatable bladder shrinks and is devoid of its volume, a characteristic that is critical for ease of introduction into the patient's body. When inflated, the inflatable bladder expands in a radial direction to ultimately form a circular or ellipsoid ring with a hole in the middle. The radial expansion is required to effectively clear the soft tissue that exists in the hypopharynx adjacent the laryngeal opening. The hole in the middle of the inflated bladder provides a clear air passage into the patient's trachea. Fully expanded inflatable bladder provides an airtight seal adjacent the laryngeal opening. These features of the inflatable bladder are important for proper functioning of the airway device disclosed herein, viz an insertion of an ETT, the delivery of oxygenated air or inhalation anesthetics, an evaluation of the airway to assess the appropriateness of extubation in an intubated patient, and an safe exchange of the ETT in an intubated patient. The esophageal cuff is inflated to protect the patient from gastric reflux and to block the mechanically delivered from going into the stomach.

An additional embodiment provides an expandable body for an airway device. The expandable body is a part of the mask section of the airway device. The expandable body includes a sheath and a tunnel. A sheath sealingly engages an inlet portion of the mask proximally, the spine section posteriorly, and an inflating bladder distally. A tunnel section disposed within the sheath extends from the inlet portion to the inflatable bladder to create a sealed connection between the inlet portion and the inflatable bladder within the sheath. Via the air-tight sealing means of both sheath and tunnel section, the expandable body is made reversibly inflatable. The expandable body may be deflated through a dedicated airtube equipped with an one-way valve. When deflated, the expandable body shrinks and becomes void, which facilitates the insertion of the device into the patient. The expandable body may be inflated through a dedicated airtube equipped with an one-way valve. Alternatively, the expandable body may be inflated passively by allowing the air to ingress into it through a one-way valve during the deployment of the inflatable bladder. When inflated, the expandable body provides an air-tight conduit that is prerequisite for the airway device disclosed herein.

An additional embodiment provides a convex spine section. The entire length of the spine section is gently curved whose curvature is defined by a radius and the center, which is located on the posterior aspect of the spine section. Thus, the convex surface of the spine section faces in the anterior direction. This novel configuration allows the distal tip of the spine section, during the insertion process, to be located in a more favorable posterior position in the hypopharynx, thus preferentially guiding the esophageal obdurator into the hypopharynx/proximal esophagus. Without the convexity disclosed herein, the spine tip will tend to be directed more anteriorly into the larynx.

A method is provided for intubating a patient. The method comprises inserting an airway device into a throat of the patient. The airway device may be preinserted with an ETT and/or endoscope. The airway device may be similar to the device mentioned in the previous paragraph and includes an overtube having a proximal end and a distal end. A mask section attached to the distal end of the overtube includes a spine section, an expandable body disposed on a proximal portion of the spine section, and an inflating bladder positioned a distance from the inlet portion, and an esophageal obdurator. The expandable body includes a sheath and a tunnel. A sheath joins an inlet portion of the mask proximally, the spine section posteriorly, and an inflating bladder distally. A tunnel section disposed within the sheath extends from the inlet portion proximally to the inflatable bladder distally to create a sealed engagement between the inlet portion and the inflatable bladder. The inflating bladder is structured to connect to the spine section with the "tire plane" (as defined SAE J670) of the inflating bladder at an angle larger than 90 degrees to the dorsal surface of the spine section. The inclination angle of the inflating bladder may be 1 degree to 45 degrees. The inflating bladder's longitudinal axis is aligned parallel to the transverse axis of a patient. When the inflatable bladder is inflated, its structure and attachment configuration as described herein effectively creates an unobstructed air passage into the trachea of the patient and an airtight seal adjacent the laryngeal opening. With the air passage cleared, if not pre-engaged in the overtube when the patient is intubated with it, an ETT and a flexible endoscope disposed within it are inserted through the overtube and advanced to the mask portion. The laryngeal opening is visualized, and under visualization, a flexible endoscope is further advanced through the laryngeal opening into the trachea. An ETT is then advanced with the flexible endoscope as a guide into the trachea. After visually confirming the proper placement and position of the ETT, the overtube and the flexible endoscope may be removed together or separately from the throat and mouth of the patient.

An additional method is provided for maintaining ventilation of a patient. The method includes the utilization of an airway device similar to that mentioned above and includes inserting an airway device into a throat of the patient. An inflatable bladder (adapted to retract soft tissue adjacent a laryngeal opening of the patient to expose vocal cords and a trachea) may then be inflated to form an airtight seal around the laryngeal opening of the patient. The method comprises inserting an airway device into a throat of the patient. The airway device may be preinserted with an ETT and/or endoscope. The airway device may be similar to the device mentioned in the previous paragraph and includes an overtube having a proximal end and a distal end. A mask section attached to the distal end of the overtube includes a spine section and an expandable body disposed on a proximal portion of the spine section, an inflating bladder positioned a distance from the inlet portion. The expandable body includes a sheath and a tunnel both of which joins an inlet portion of the mask proximally, the spine section posteriorly, and an inflating bladder distally. A tunnel section disposed within the sheath extends from the inlet portion to the inflatable bladder to create a sealed engagement between the inlet portion and the inflatable bladder. The inflating bladder is structured to connect to the spine section with the "tire plane" (as defined SAE J670) of the inflating bladder at an angle larger than 90 degrees to the dorsal surface of the spine section. The inclination angle of the inflating bladder may be 1 degree to 45. When the inflatable bladder is inflated, its structure and attachment configuration as described herein effectively creates an unobstructed air passage into the trachea of the patient and an airtight seal adjacent the laryngeal opening, so that the delivered oxygenated air may not leak out of the patient. The esophageal cuff is inflated to protect the patient from gastric reflux and to block the mechanically delivered oxygenated air or inhalation anesthetics going into the stomach. The proper placement of the airway device may be visually confirmed by a flexible endoscopy via the overtube. The proximal end of the overtube may then be connected to a ventilator that may deliver at least one of oxygen, air, and anesthetic to the patient.

An additional method is provided for exchanging an ETT on an intubated patient. The method includes the utilization of an airway device similar to that mentioned above and includes inserting the airway device over an inserted/preexisting ETT into a throat of a patient. The airway device includes an overtube having a proximal end and a distal end. A mask section attached to the distal end of the overtube includes a spine section and an expandable body disposed on a proximal portion of the spine section, an inflating bladder positioned a distance from the inlet portion. The expandable body includes a sheath and a tunnel both of which joins an inlet portion of the mask proximally, the spine section posteriorly, and an inflating bladder distally. A tunnel section disposed within the sheath extends from the inlet portion to the inflatable bladder to create a sealed engagement between the inlet portion and the inflatable bladder. The inflating bladder is structured to connect to the spine section with the "tire plane" (as defined SAE J670) of the inflating bladder at an angle larger than 90 degrees to the dorsal surface of the spine section. The inclination angle of the inflating bladder may be 1 degree to 45. When the inflatable bladder is inflated, its structure and attachment configuration as described herein effectively creates an unobstructed view of the larynx and the trachea the patient. An endoscope may then be advanced through a mask section of the device and into the trachea of the patient. Once the endoscope is advanced and properly positioned, the preexisting ETT may then be removed and a new ETT may be advanced over the endoscope and into the trachea of the patient. At this point, the overtube may be retracted until the overtube is fully removed from the throat and mouth of the patient. Subsequently, the endoscope is then retracted until the endoscope is fully removed from the throat of the patient.

An additional method is provided for examining at least one of the larynx and trachea of an intubated patient. The method includes the utilization of an airway device similar to that mentioned above and includes inserting the airway device over a preinserted/preexisting ETT into a throat of a patient. Once inserted, an inflatable bladder adapted to retract soft tissue adjacent a laryngeal opening of the patient to expose vocal cords and a trachea of the device is inflated to form an airtight seal around a laryngeal opening of the patient. An endoscope may then be advanced through the ETT and into the trachea of the patient. Once the endoscope is advanced and properly positioned, the ETT cuff (inflated previously) may be deflated and the preexisting ETT may then be retracted proximal to the larynx. At this point, the larynx and/or trachea may be examined and the preexisting ETT or a new ETT may then be advanced back into the trachea over the fiberoptic endoscope.

An additional method is provided for clearing the soft tissue from the larynx and hypopharynx of a patient. The method utilizes an airway device similar to that mentioned above and includes an expandable, torus-shaped bladder attached to the mask framework in its transverse axis. The airway device is inserted into the patient and subsequently positioned so that the bladder is adjacent the larynx and hypopharynx of the patient. Once inserted into the patient, the bladder is expanded and assumes a rigid, circular or ellipsoid torus. The inflatable bladder expands in a radial direction to ultimately form a circular or ellipsoid ring with a hole in the middle. The said radial expansion of the inflatable bladder pushes the soft tissue that is normally present within the hypopharyngeal lumen adjacent the laryngeal opening toward the periphery to provide an unobstructed air passage into the trachea of the patient.

An additional method is provided for collecting and evacuating oronasal secretion from a patient. The method includes inserting an airway device that is equipped with a collection apparatus into a patient. The airway device provided may be similar to the airway device mentioned above and additionally includes a collection apparatus attached to the posterior surface of the mask section/spine and the inflating bladder. The collection apparatus is enclosed by a thin-walled, semi-rigid plastic that follows the contour of the vental segment of the inflating bladder—that is the portion of the inflating bladder posterior to the spine section. The superior portion of the collection apparatus is left open to allow ingress of secretion into the collection. The floor of the collection apparatus is formed by the superior surface of the posterior segment of the inflating bladder. The superior edge of the collection apparatus is configured to flare out to ensure the superior edge to make a water-tight seal with the hypopharyngeal wall. The collection apparatus is hermetically sealed (by means of adhesives, chemicals, heat, ultrasonic bonding, etc.), to the posterior surface of the spine anteriorly and the inflating bladder inferiorly. Once the airway device is properly positioned adjacent the laryngeal opening of the patient, the collection apparatus may be positioned in the patient's hypopharynx in an open configuration so that oronasal secretion may be collected in the collection apparatus instead of having the oronasal secretion travel near or into the laryngeal opening of the patient, thus creating a safe environment for the patient. A suction catheter may then be utilized to evacuate the oronasal secretion or blood from the collection apparatus. The suction catheter may be pre-installed on a wall of the overtube or may be introduced along the pre-formed path (along the bottom of the airway device) after the airway device is inserted into a patient.

An additional method is provided for producing an airway device. The airway device may include a structure similar to the airway device mentioned above and may enhance facility with which it can be introduced into a patient. The method includes forming a spine section as a thin strip that may embody a length ranging from 50 millimeters to 120 millimeters, a width ranging from 5 millimeters to 20 millimeters, and a thickness ranging from 1 millimeter to 10 millimeters. The entire length of the spine section and the esophageal obdurator is configured to form a gentle convexity with the convexity pointing in the anterior direction, and the radius of the convex curvature ranging 100 to 500 millimeters. The configuration of the spine embodying the dorsal convexity may lessen the mask section's tendency to move anteroinferiorly toward the larynx and encourage the mask section to advance (preferably) in the inferior direction into the hypopharynx/proximal esophagus of the patient. A torus-shaped inflatable bladder is then affixed to the spine section a distance from the inlet portion. This attachment is so structured that the inflating bladder may attach to the anterior or posterior surface of the spine. Alternatively, the inflating bladder may be positioned in the center of the spine section with the anterior and posterior portion of the spine section positioned adjacent each side of the bladder.

BRIEF DESCRIPTION OF THE DRAWINGS

The disclosed subject matter, objectives, and advantages thereof, will best be understood by reference to the following detailed description of an illustrative embodiment when read in conjunction with the accompanying drawings, wherein.

DETAILED DESCRIPTION

Reference now should be made to the drawings, in which the same reference numbers are used throughout the different figures to designate the same components.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Figure 1:
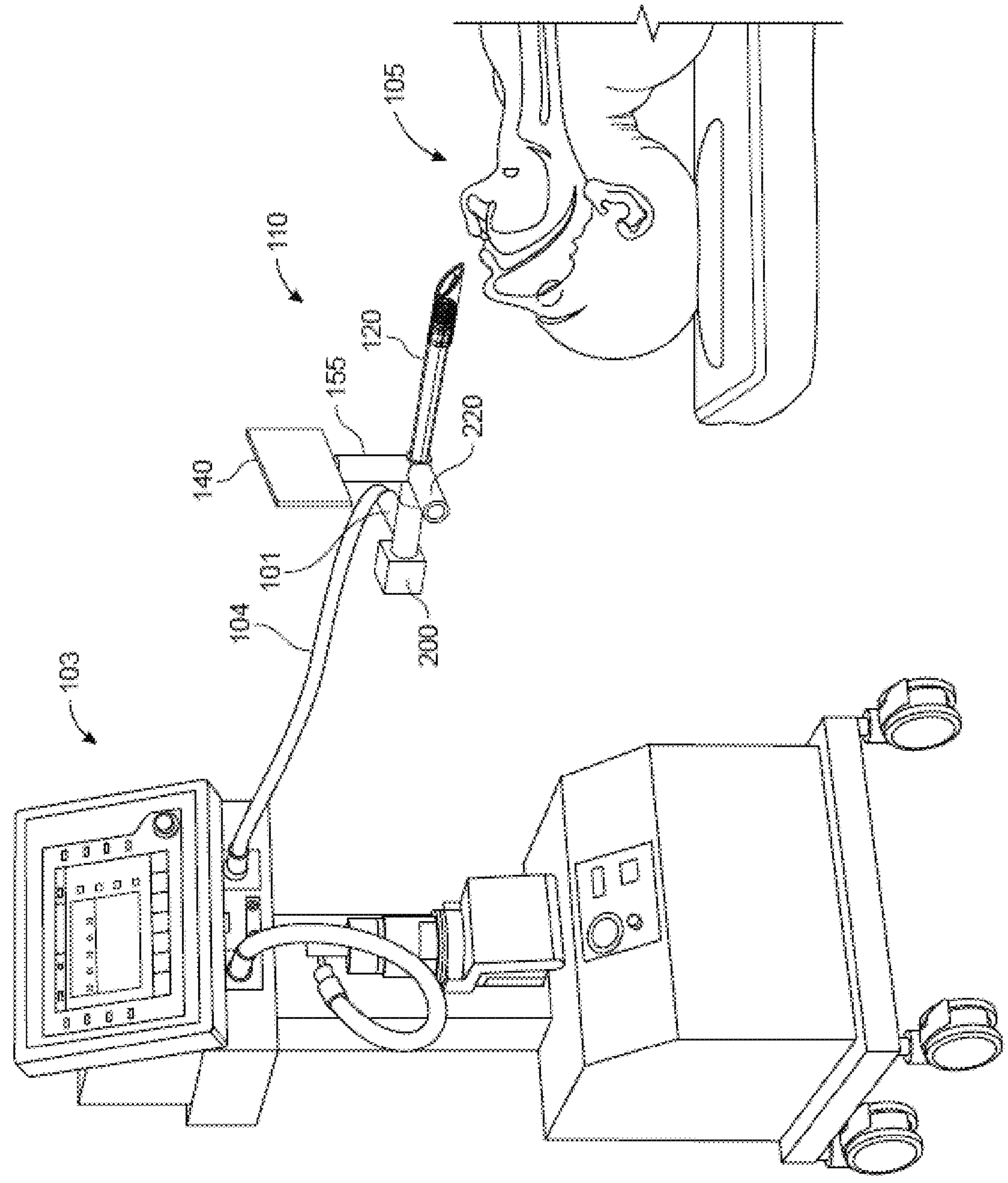
FIG. 1 displays a perspective view of an intubation system in accordance with embodiments.

FIG. 1 displays a perspective view of an intubation system 100 in accordance with embodiments. Intubation system 100 may be utilized to efficiently insert an ETT (endotracheal tube) 130 into a patient's trachea (see FIGS. 7A, 7B, and 7C). System 100 may comprise a ventilator 103, ventilator tubing 104, a ventilator connector 101, and an intubation device 110. Ventilator 103 may be utilized in conjunction with intubation device 110 in order to supply air to a patient 105 while intubation device 110 is inserted/positioned within patient 105. Ventilator 103 may, in embodiments, be any type of standard ventilator found in a hospital. Ventilator 103 may include a ventilator tubing 104 that is connectable to a port (not depicted) of ventilator connector 101 (shown in FIG. 1 as a T-joint). Ventilator connector 101 may be hollow in order to allow air to pass through to intubation device 110. In embodiments, ventilator connector 101 may be incorporated as a single body with intubation device 110.

In other embodiments, ventilator connector 101 may affix to intubation device 110 via means including, but not limited to threading, twist-lock engagement, O-ring attachment, magnetic attachment, form-fitting, and male-female engagement. When intubation device 110 is not in use, ventilator connector 101 may be removed for storage purposes. In other instances, ventilator connector 101 may be left on intubation device 110 and a lid 102 may be affixed to an end of intubation device 110 proximal the location of attachment of ventilator connector 101 (see FIG. 2). In embodiments, lid 102 may be affixed to an end of intubation device 110 via means previously mentioned including, but not limited to threading, twist-lock engagement, O-ring attachment, magnetic attachment, form-fitting, and male-female engagement.

Figure 2:
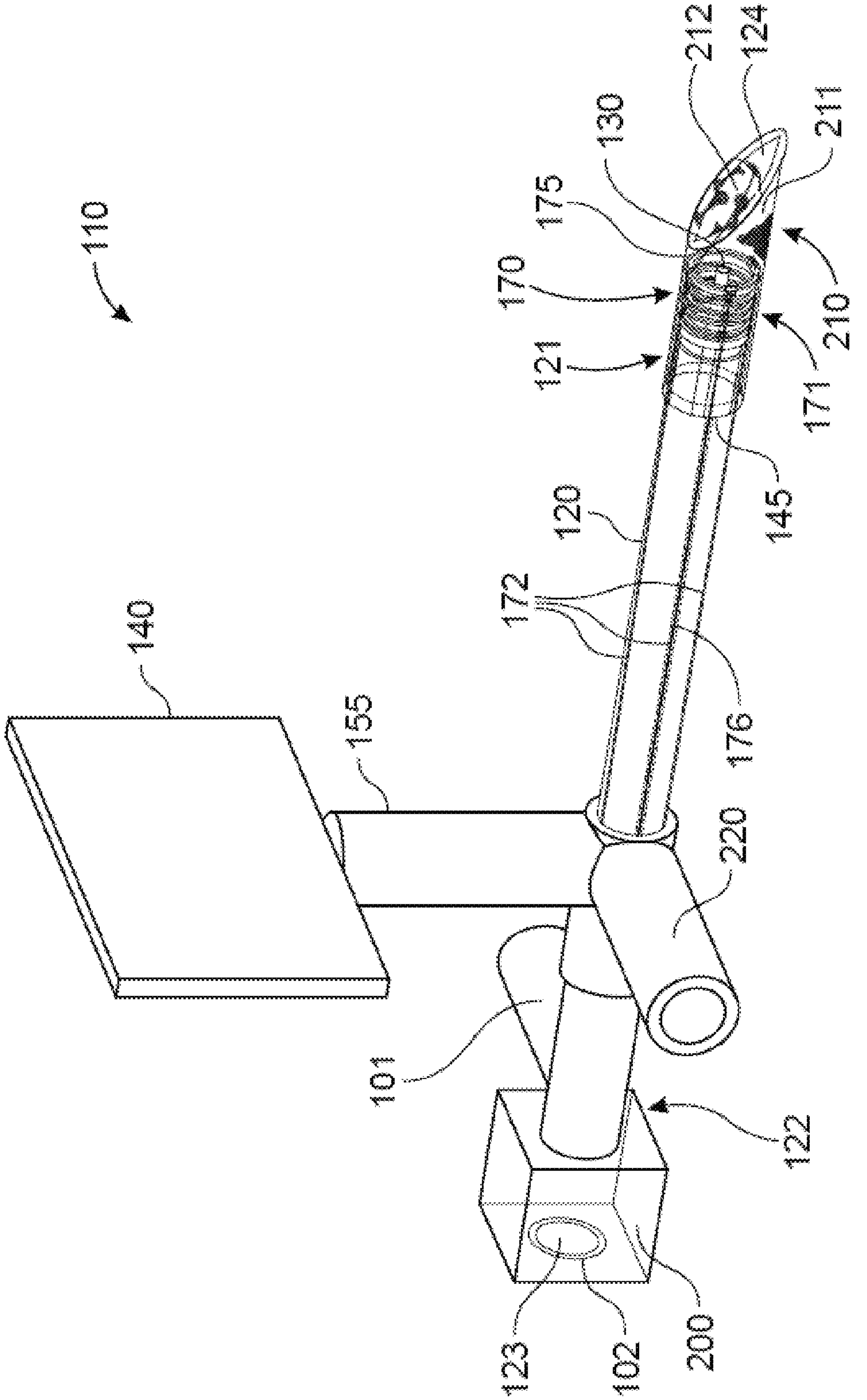
FIG. 2 displays a perspective view of an intubation device in accordance with embodiments.

As shown in FIGS. 1 and 2, ventilator tubing 104 is connected to the open end of ventilator connector 101. One end of the horizontal member of the ventilator connector 101 may be connected to the proximal end 122 of a semirigid portion of overtube 120. The other end of the horizontal member may be affixed to actuation module 200. Intubation device 110 may comprise, in embodiments, a video monitor 140 and a monitor attachment section 155 affixed to overtube 120. These elements may be further described in subsequent figures. Handle 220 may be removably affixable adjacent the proximal end 122 of overtube 120. In embodiments, handle 220 may be affixed directly to at least one of monitor attachment section 155 and overtube 120.

In embodiments, ETT (endotracheal tube) 130 may be any other form of medical airway tube. Endotracheal tube (ETT) may also be referred to as an "airway tube" or an "intubation tube".

Figure 3:
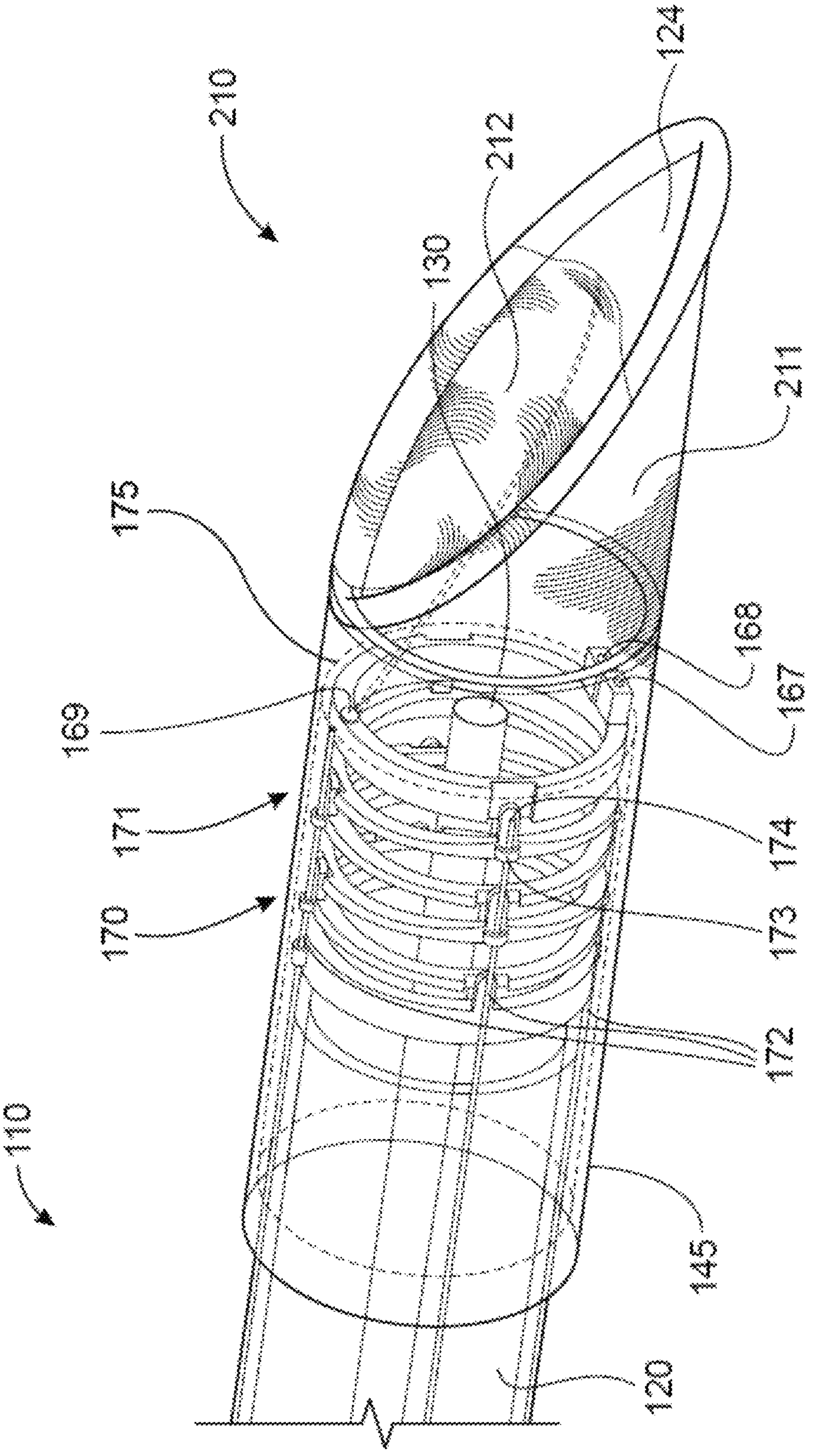
FIG. 3 displays a perspective front view of an intubation device in accordance with embodiments.

FIG. 2 displays a perspective view of an intubation device 110 in accordance with embodiments. Intubation device 110 may be utilized to position an ETT 130 into a laryngeal opening 213 of patient 105. Intubation device 110 may comprise an overtube 120, a flexible tip 170, a stem 145, a hood 210, a video monitor 140, a monitor attachment section 155, a ventilator connector 101, and an actuation module 200. Overtube 120 includes a semirigid proximal portion, a flexible distal tip 170, and a hood 210. Hood 210 may include stem 145, hood base 211 contiguous with a posterior wall of stem 145, esophageal seal (not depicted), and hood body 212 having an expandable structure. The semirigid portion includes a proximal end 122 and a distal end 121. The flexible tip 170 affixes to the distal end 121 of the semirigid portion via the plurality of control wires 172 and malleable covering 175 (depicted in dotted lines in FIG. 3). As shown in FIG. 3, malleable covering 175 may cover the plurality of discs 171 and may be affixed to the distal end 121 of overtube 120. In embodiments, malleable covering 175 may be affixed to the distal end 121 of overtube 120 via at least one of ultrasonic welding, thermal bonding, and adhesive.

Overtube 120 may comprise an interior surface, an exterior surface, and an interior space that may house at least the ETT 130. Semirigid portion of overtube 120 may be designed to be semi-rigid/semi-flexible and may be made from a material in order to meet certain rigidity/flexibility requirements (such as, but not limited to, bending to efficiently fit within a patient's throat 214). In certain embodiments, overtube 120 may comprise polymer tubing such as, but not limited to polyvinyl chloride (PVC), silicone, and/or other thermoplastic materials. In embodiments, portions of the semirigid portion of overtube 120 may comprise a corrugated configuration in order to allow for additional flexibility.

Flexible tip 170 may be disposed within hood 210 and/or stem 145; both the flexible tip 170 and hood 210 may maintain rigidity and attachment to overtube 120 via stem 145. Stem 145 is a tubular portion of hood 210 that may overlap the semirigid portion of overtube 120, flexible tip 170, and stem 145 so that flexible tip 170 and additional material of hood 210 are secured between stem 145 and exterior surface of overtube 120. In certain embodiments, stem 145 may be removably affixable to overtube 120 using any of the aforementioned affixing means.

Flexible tip 170 may be fashioned to be more flexible than overtube 120 and may be freely contained within at least one of the stem 145 and hood 210. Flexible tip 170 may articulate 30 degrees or more in a vertical and/or horizontal direction within flexible tip 170 so that when device 110 is positioned adjacent a laryngeal opening 213 of a patient 105, flexible tip 170 may be manipulated to aim directly at the laryngeal opening 213 so that an ETT 130 (or other intubation tube) may be easily fed into the laryngeal opening 213 (and not into esophageal opening 215).

Monitor attachment section 155 may be affixed to an exterior surface of overtube 120 so that video monitor 140 may be maintained in a position viewable by an individual using device 110 when device 110 is positioned within the throat 214 of a patient 105. In certain embodiments, monitor attachment section 155 may be removably affixable so that the position of monitor attachment section 155 and video monitor 140 may be adjusted.

To insert the ETT 130 into device 110, the ETT 130 may be manually advanced through either the proximal opening (actuation module orifice 123) or distal opening 124 of hood 210 until the ETT 130 is positioned completely inside overtube 120. In embodiments, internal components of device 110 may hold ETT 130, at least temporarily, in place within device 110.

The plurality of control wires 172 affixed to the flexible tip 170 may be utilized to manipulate the position of the flexible tip 170. The plurality of control wires 172 may be connected to an actuation module 200 positioned at proximal end 122 of overtube 120. Each of the wires 172, in embodiments, may be surrounded by a flexible sheath 176 (see dotted line surrounding middle wire 172) that may be affixed to an interior surface of overtube 120 in order to keep wires 172 isolated from the ETT 130 or other components found within overtube 120. The flexible sheath 176 may also be constructed to flex with overtube 120 when overtube 120 is flexed within a patient 105. Flexible sheath 176 may be made of the same or a similar material as that of overtube 120. In other embodiments, each of the wires 172 may be positioned adjacent an exterior surface of overtube 120. The wires 172 may be surrounded by a flexible sheath 176 that may be affixed to an exterior surface of overtube 120 in order to keep wires 172 isolated from any interior components found within overtube 120. In embodiments, flexible sheath 176 may be affixed to overtube 120 via one or more attachment means such as, but not limited to, adhesive, heat bonding, solvent bonding, and ultrasonic welding.

It is noted that the wires 172 may embody a medium to low flexural rigidity in order for the wires 172 to bend with overtube 120 but may also embody a high compressive force in order for the wires 172 to be pushed forward in the flexible tip 170 so that flexible tip 170 may be moved in one or more directions. In certain embodiments, wires 172 may comprise an elastic material.

FIG. 3 displays a perspective front view of an intubation device 110 in accordance with embodiments. As shown, flexible tip 170 may include an interior frame comprising a plurality of discs 171 spaced apart from one another as well as a malleable covering 175. Alternatively, flexible tip may be a spring of sufficient flexibility covered with malleable covering 175. The four wires 172 may extend through loops 173 positioned on all discs 171 except for the disc 171 closest to distal opening 124; wires 172 may include wire ends 174 anchored to the disc 171 closest to the distal opening 124. This configuration may allow for the movements of all disks 171 when wires 172 are actuated. As shown, the four wires 172 may be equally spaced around the circumference of overtube 120. The four wires 172 may be separated into pairs of wires 172 (left-right and top-bottom). The left—right pair of wires 172 controls the flexible tip 170 bending left and right, while the top-bottom pair of wires 172 controls the flexible tip 170 bending up and down. Actuation module 200 actuates wire-controlled flexible tip 170 of overtube 120 in order to fine tune the positioning of the flexible tip 170 for arrival at its ultimate position once flexible tip 170 is positioned at the laryngeal opening 213. ETT 130 may be advanced into the trachea by a plurality of means.

In order to keep the discs 171 stationary (not sliding along wires 172) and spaced from one another, a malleable covering 175 may be disposed around the discs 171. The malleable covering 175 may be thin and may comprise a high flexural strength; covering 175 may comprise a polymeric material such as, but not limited to, polytetrafluoroethylene (PTFE), fluorinated ethylenepropylene (FEP), perfluoroalkoxy (PFA), ethylene tetrafluoroethylene (ETFE), polyether ether ketone (PEEK), polyvinyl chloride (PVC), and rubbers. In other embodiments, covering 175 may be corrugated in order to keep discs 171 from sliding along wires 172. In other embodiments, resilient devices, such as, but not limited to springs, may be positioned between and attached to adjacent discs 171 in order to keep discs stationary and allow for flexibility when in use.

Hood 210 may comprise a base 211, a hood body 212, an inferior projection acting as an esophageal seal (not depicted). Base 211 may comprise a solid semi-flexible structure and may be designed to sit against the posterior hypopharyngeal wall. Hood body 212 is affixed to base 211 and may provide the function of applying pressure to the soft tissue in the laryngeal vestibule and the hypopharynx of an individual so as to retract the soft tissue out of the line of vision of the device 110/a user of intubation device 110. Hood body 212 may be fashioned as a domeshaped expandable/inflatable structure affixed to the sides of base 211. In embodiments, hood body 212 may be half frustospherical or half frusto-conical in shape (roughly frustospherical or frusto-conical in shape in combination with base 211. The superior portion of the body 212 (adjacent overtube 120) may be contiguous or non-contiguous with the superior portion of body 212. The inferior portion, which faces the larynx when in use, is left open. In certain embodiments, hood body 212 may comprise an expandable/inflatable section having an inflating bladder made of soft plastics and/or fabrics. A deflated/collapsed hood body 212 may be inflated to a rigid/expanded state and may inflate outwardly away from base 211 to push out the soft tissue from the hypopharynx and laryngeal vestibule 213. Additionally, hood body 212 may be made taut and advanced anteriorly by a plurality of mechanisms including at least one of a hydraulic, pneumatic, and electromechanical system in order to apply pressure anteriorly to the hood body 212 to push out the soft tissue from the hypopharynx and laryngeal vestibule 213 (hood body 212 may act as a tent and may, in embodiments, include an expandable frame/element and/or expandable covering). The esophageal seal (not depicted) may be an inferior projection of hood body 212 and may comprise a solid, semi-flexible structure. It may serve to occlude the esophageal opening 215 when device 110 is positioned properly within a throat 214. In embodiments, esophageal seal may be any type or configuration of esophageal seal found in the art. Once device 110 is placed in the throat 214, deflated inflatable bladder of hood body 212 is inflated to a rigid state and inflates outwardly away from base 211 to push out the soft tissue from the hypopharynx and laryngeal vestibule 213. After the soft tissue is cleared out of the field of vision of a user of device 110, overtube 120 is advanced via a plurality of mechanisms including, but not limited to, an attachment means (tip director 169/alternative tip director 165) between the hood body 212 and flexible tip 170 of overtube 120 or base 211 and flexible tip 170. In embodiments, stem 145 and base 211 may be one contiguous part (made of the same material). It is noted that hood body 212 may be described as being in a retracted state when hood body 212 is not expanded and in an expanded state when hood body 212 is inflated/expanded to a rigid structure.

Via the tip director 169, the two processes of the soft tissue clearing and the overtube 120 positioning are effected simultaneously when hood body 212 is expanded.

When flexible tip 170 is positioned (by the inflating action of inflatable bladder/expansion of hood body 212) adjacent a laryngeal opening 213 of a patient 105, flexible tip 170 may be further maneuvered to precisely align overtube 120 with the laryngeal opening 213 of a patient 105 via manipulation of wires 172 using the mechanisms found in actuation module 200. Tip director 169 and its functionality may be discussed further in the following paragraphs.

Mechanisms in actuation module 200 may administer applied forces to one or more of the wires 172 so that wires 172 may be extended and/or retracted in flexible tip 170, which may adjust the position of flexible tip 170. In embodiments, the mechanisms may include one or more motors 250 (see FIG. 8) that control one or more wind-up/retraction systems (not shown) that may administer an applied force to the wires 172, which may pull or push the wires 172 (thus moving flexible tip 170). In other embodiments, the mechanisms may include ends of a pair of wires 172 affixed to a first chain 188 (see FIG. 8). First chain 188 may be rotated by one or more gears 255 actuated by one or more motors 250. The other two ends of the remaining pair of wires 172 may also be affixed to a second chain 198 that may be rotated by one or more gears 255 actuated by one or more motors 250. The rotation of the gears 255 may administer an applied force to the wires 172, which may pull or retract one wire 172 in a pair and push or extend the other wire 172 in the pair (thus moving flexible tip 170). In embodiments, each of the gears 255 may be actuated by separate motors 250 or both may be actuated by a single motor 250. Each of the described mechanisms may be positioned within actuation module 200 for proper functionality within device 110. It is noted that one skilled in the art can conceive of and create the components contained in actuation module 200 (such as, but not limited to the one or more motors 250 and the one or more wind-up/retraction systems).

A camera 168 and a light source 167 may be positioned on the distal portion of flexible tip 170. These elements help an individual using device 110 to view the location of flexible tip 170 in relation to the laryngeal opening 213 of a patient 105 (when device 110 is inserted into a throat 214) so that the individual may manipulate the device 110 to an optimal positioning within throat 214 to allow flexible tip 170 to extend into laryngeal opening 213. Wiring of the light source 167 may extend through device 110 to a power source 257 (see FIG. 8) positioned in monitor attachment section 155. Wiring of the camera 168 may also extend through device 110 to power source 257 positioned in monitor attachment section 155. Additional wiring of the camera 168 may extend through device 110 and monitor attachment section 155 to monitor 140 to provide a video feed inside of a patient 105 when device 110 is adjacent a laryngeal opening 213.

The wiring of camera 168 and light source 167, in embodiments, may be surrounded by a flexible sheath (similar to or the same as the flexible sheath 176 covering the wires 172) that may be affixed to either an interior surface of overtube 120 or an exterior surface of overtube 120 depending on whether the wiring is run along an interior surface or an exterior surface of overtube 120. This may allow the wiring to be isolated from other components of device 110. The flexible sheath of the wiring of camera 168 and light source 167 may be constructed to flex with overtube 120 when overtube 120 is flexed within a patient 105. Flexible sheath may be made of the same or a similar material as what overtube 120 is made of. In embodiments, flexible sheath may be affixed to overtube 120 via one or more attachment means such as, but not limited to, adhesive, heat bonding, solvent bonding, and ultrasonic welding.

In other embodiments, flexible tip 170 may include a malleable covering 175 without discs 171. In this configuration, wires 172 may be affixed to a portion of covering 175 closest to distal opening 124 in order to allow for manipulation of flexible tip 170. It is noted that in this embodiment, malleable covering 175 may comprise a polymer that maintains its structural integrity without using discs 171.

In other embodiments, interior frame of flexible tip 170 may comprise a spring as opposed to discs 171. In this configuration, wires 172 may be affixed to a portion of the spring closest to distal opening 124 in order to allow for manipulation of flexible tip 170. It is noted that in this embodiment, the spring may provide a more stable interior frame/user experience due to the compressive force of the spring in combination with the extension and retraction of wires 172.

In other embodiments, actuation module 200, wires 172, flexible sheaths 176, and loops 173 may be absent from device 110. In this configuration of device 110, flexible tip 170 may include either discs 171 and a malleable covering 175 or may only include a malleable covering 175. With the absence of wires 172 and other components used by wires 172, flexible tip 170 may rely on tip director 169 or alternative tip director 169 to position flexible tip 170 adjacent a laryngeal opening 213.

In other embodiments, the setup and number of wires 172 may vary. For example, device 110 may comprise less than four wires 172 or more than four wires 172 positioned similarly or differently than the example described above.

Figure 4:
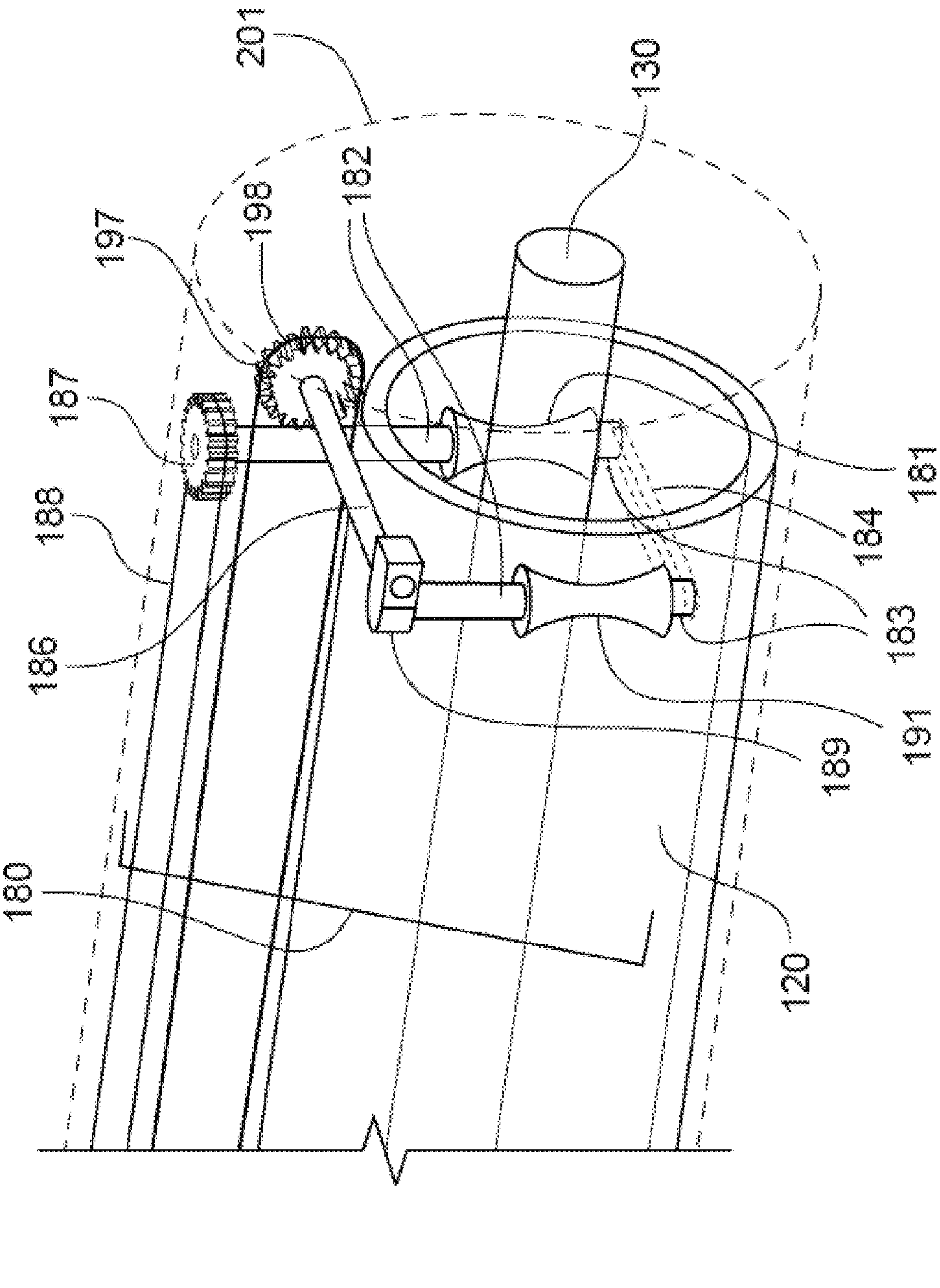
FIG. 4 displays a partial cutaway view of an intubation device having a feeder mechanism in accordance with embodiments.

FIG. 4 displays a partial cutaway view of an intubation device 110 having a feeder mechanism 180 in accordance with embodiments. The feeder mechanism 180 may be positioned at the junction of the flexible tip 170 and semi-rigid portion of the overtube 120 (partially or fully overlapped by stem 145) and may function to advance ETT 130 through overtube 120 and out of the distal end 121 of overtube 120. Feeder mechanism 180 may include a pair of diametrically opposed rollers 181, 191. A first roller 181 may be stationary and may be incorporated into an interior wall of overtube 120 via a base 183. First roller 181 may be affixed to base 183 via a shaft 182, which also juts out of the top side of first roller 181. Base 183 may include a bearing engageable with shaft 182 so that first roller 181 may rotate. To control the spinning movement of first roller 181, shaft 182 at the top side of first roller 181 may be affixed to a first gear 187 positioned horizontally in relation to first roller 181; first gear 187 may be driven by a first chain 188 that extends into actuation module 200 which houses a gear 255 affixed to a motor 250 (see FIG. 8) that turns first gear 187 and causes first chain 188 to move (thus rotating first roller 181).

Second roller 191 may include a shaft 182 that juts out of a top side of second roller 191. The shaft 182 of second roller 191 may be affixed to a screw receiver 189 that juts outward towards the distal end 121 of overtube 120 (in relation to where second roller shaft 182 is affixed to screw receiver 189). In certain embodiments, a screw shaft 186 may be positioned within screw receiver 189 at one end and may be affixed to an interior wall of overtube 120 at a screw shaft base (not depicted) adjacent first roller 181. The screw shaft base may include a bearing in order to allow screw shaft 186 to rotate. This configuration may be constructed on either end of screw shaft 186. In embodiments (as depicted in FIG. 4), when portions of the feeder mechanism 180 are positioned externally to overtube 120, screw shaft base may be affixed to an exterior wall of overtube 120 in this instance. Additionally, it is noted that screw receiver 189 and screw shaft 186 both comprise threads that allow the screw shaft 186 to move/twist through screw receiver 189.

A second gear 197 may be affixed to a second chain 198 that extends into actuation module 200 which houses a gear 255 affixed to a motor 250 that turns second gear 197 and causes second chain 198 to move, thus rotating screw shaft 186 and causing screw receiver 189 and second roller 191 to move laterally towards first roller 181. This in turn forces both the first roller 181 and the second roller 191 to engage ETT 130 and securely feed ETT 130 through distal opening 124 of device 110 (ETT 130 moves due to the rotation of first roller 181). In this instance, ETT 130 is "automatically" fed through distal opening 124. In embodiments, first and second rollers 181,191 may be covered with a material with a high coefficient of friction and may be shaped to conform to the contour of ETT 130.

In other embodiments, a spring may be utilized in place of screw shaft 186. One end of a spring may affix to screw receiver 189, while the other end may affix to either the shaft 182 of first roller 181 or to the interior surface of overtube 120. When ETT 130 is positioned between first roller 181 and second roller 191, the spring may extend to allow second roller 191 to move laterally away from first roller 181 to provide a secure feeder mechanism 180 for ETT 130. In some instances, an inner support shaft may be positioned within the spring (and affixed to screw receiver 189 and either the shaft 182 of first roller 181 or the interior surface of overtube 120) in order to avoid lateral bending of the spring.

Figure 8:
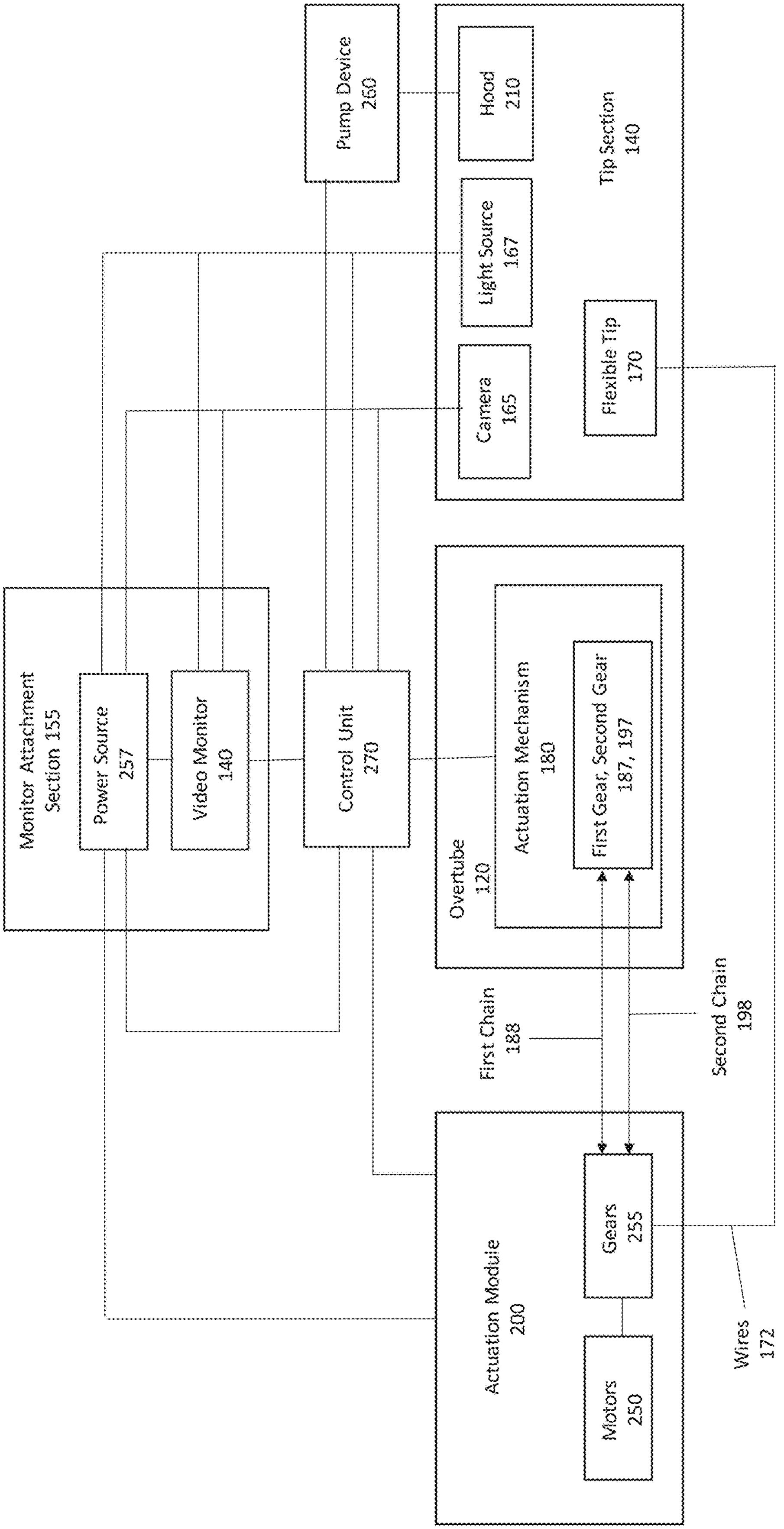
FIG. 8 displays a components diagram of an intubation device in accordance with embodiments.

It is noted that the actuation of feeder mechanism 180 may be carried out either by hand, such as, but not limited to, using one or more hand cranks, or using a control unit 270 (see FIG. 8). Control unit 270 may include a user input for controlling the motors 250 that run the gears 255 and chains 188,198 for controlling feeder mechanism 180.

In any of the aforementioned embodiments, a base 183 of second roller 191 may be disposed within a roller track 184 in order to keep the second roller 191 balanced and avoid shifting within overtube 120. Roller track 184, in embodiments, may comprise walls on each side of second roller base 183 that extend from one side of overtube 120 to the other in order to have second roller 191 avoid shifting problems and keep it moving along a path across the width of overtube 120.

In embodiments, one or more components of feeder mechanism 180 may be disposed outside of overtube 120. These components may be covered by an outer covering 201. For example, first and second gears 187,197 may be positioned outside of overtube 120; outer covering 201 may only cover these components. It is noted that outer covering 201 may be affixed to overtube 120 so that overtube, including outer covering 201, is airtight.

Figure 5:
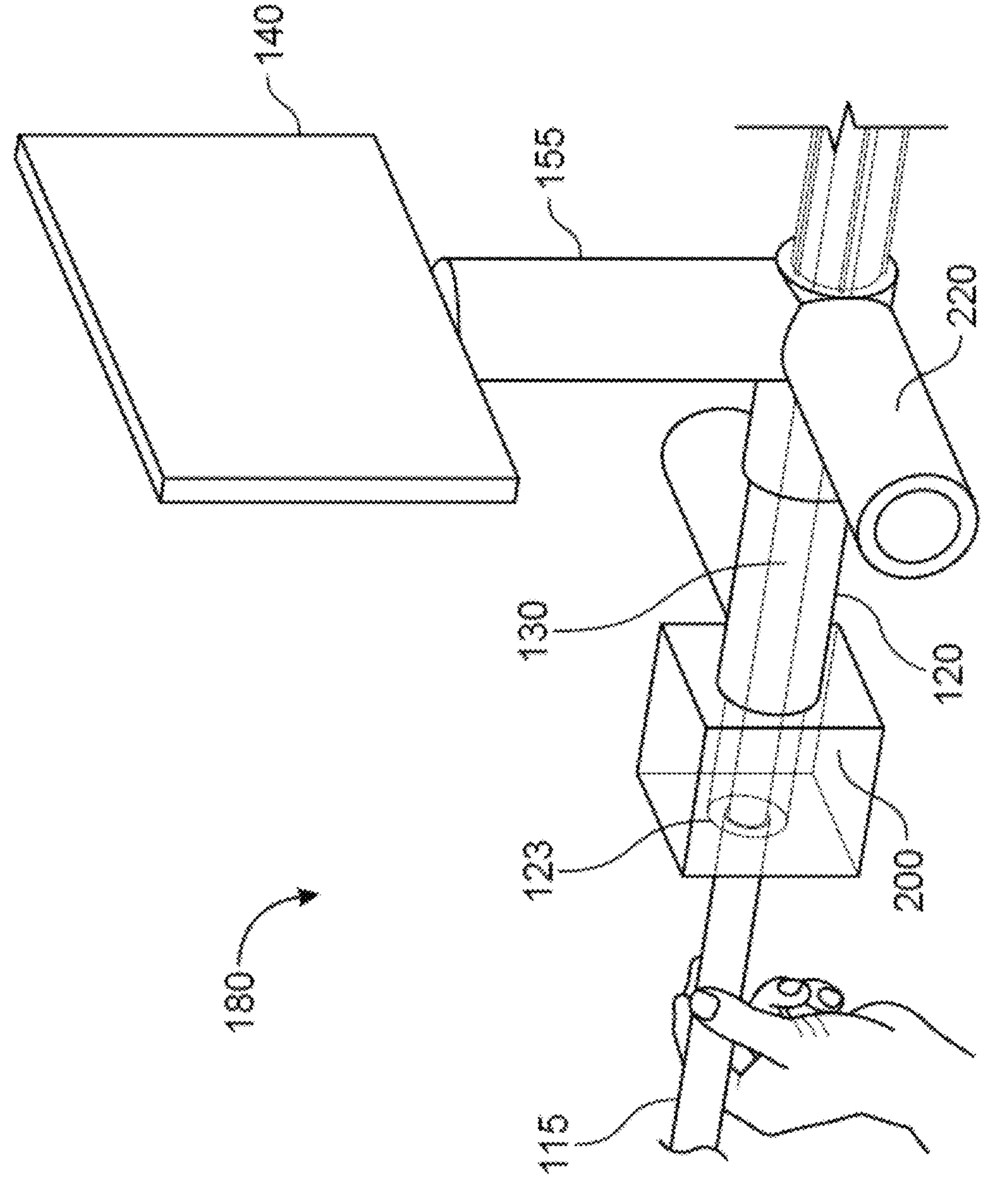
FIG. 5 displays a partial cutaway view of an intubation device having an alternative feeder mechanism in accordance with embodiments.

FIG. 5 displays a partial cutaway view of an intubation device 110 having an alternative feeder mechanism 180 in accordance with embodiments. Feeder mechanism 180 found in FIG. 5 may be an alternative feeder mechanism 180 that may be utilized to advance ETT 130 through overtube 120 and out of the distal opening 124 of hood 210. Lid 102 (see FIG. 2) of actuation module 200 may be taken off to reveal an orifice (actuation module orifice 123) that may extend through actuation module 200 to overtube 120. In order to advance ETT 130, an individual operating device 110 may use a rod 115 to manually push and advance ETT 130 through overtube 120. This may be carried out in order to push ETT 130 into the laryngeal opening 213 of a patient 105 once the flexible tip 170 is positioned adjacent a laryngeal opening 213.

Figure 6:
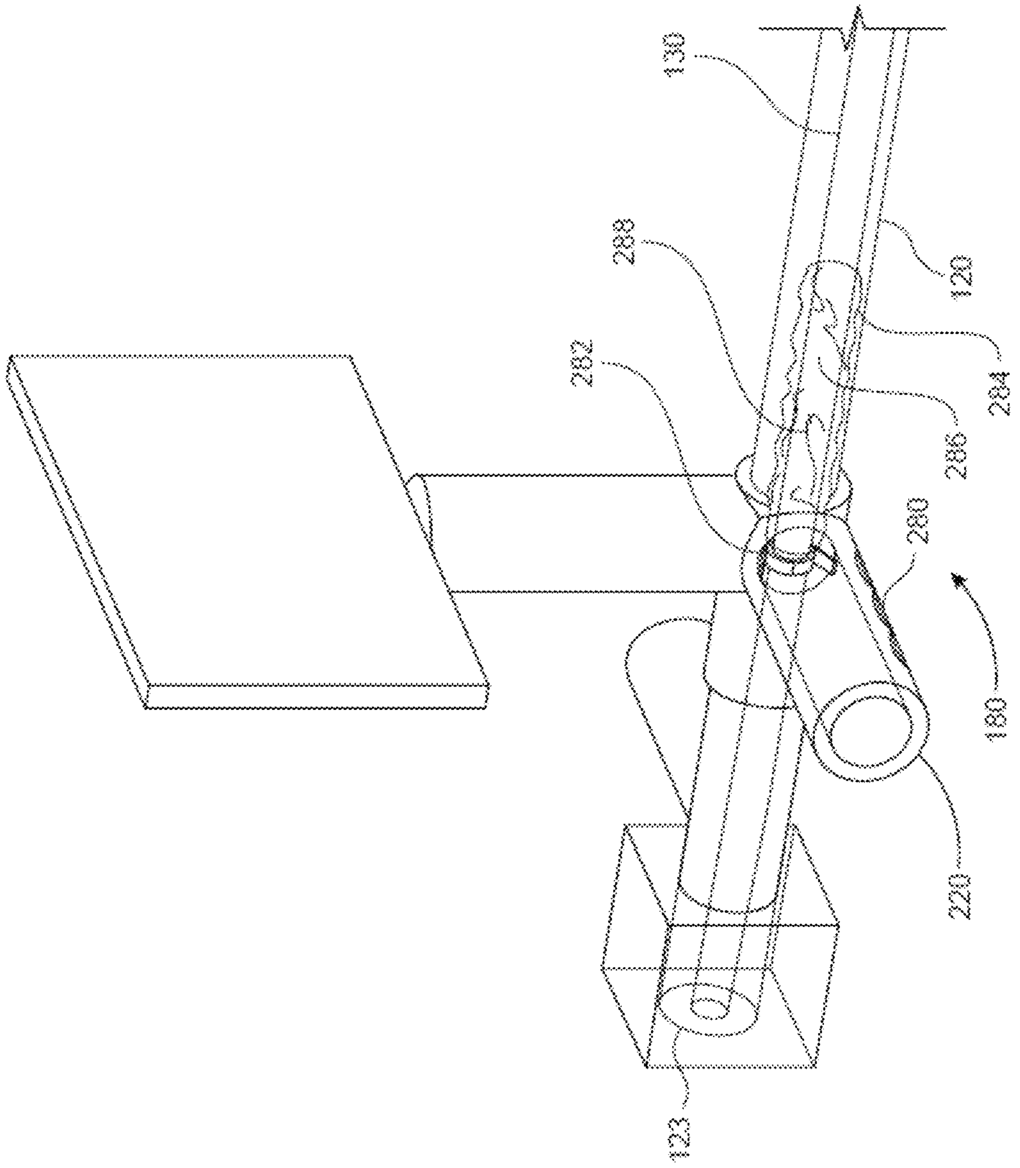
FIG. 6 displays a partial cutaway view of an intubation device having an alternative feeder mechanism in accordance with embodiments.

FIG. 6 displays a partial cutaway view of an intubation device 110 having an alternative feeder mechanism 180 in accordance with embodiments. Feeder mechanism 180 found in FIG. 6 may be an alternative feeder mechanism 180 that may be utilized to advance ETT 130 through overtube 120 and out of the distal opening 124 of hood 210. Handle 220 may include a trigger mechanism 280 that may be actuated by the hand of a user of device 110. Trigger mechanism 280 may be affixed to a clamp 282 so that when trigger mechanism 280 is disengaged, clamp 282 securely clamps onto ETT 130 so that ETT 130 does not shift in any direction/is stationary. When clamp 282 is secured, handle 220 may be shifted along the length of overtube 120 to advance ETT 130 out of the distal opening 124 of hood 210. To keep handle 220 secure and device 110 airtight, handle 220 may be run along a track 286 (such as an extended male-female engagement system/track, etc.) affixed to or within device 110. The area surrounding track 286 (the length of device 110 where handle 220 moves in track 286), referred to as the extension zone 284, may be covered with malleable covering 288 which may comprise a polymeric covering (similar to material surrounding a stick shift in an automobile). Malleable covering 288 may comprise an elasticity to allow a user to move handle 220 laterally and to keep device 110 airtight. It is noted that handle 220 may be able to move ETT 130 a longer or shorter distance depending on the elasticity of malleable covering 288.

It is noted that one skilled in the art can conceive of and create the components for affixing trigger mechanism 280 to clamp 282 so that when trigger mechanism 280 is actuated, clamp 282 securely clamps onto ETT 130.

Figure 7A:
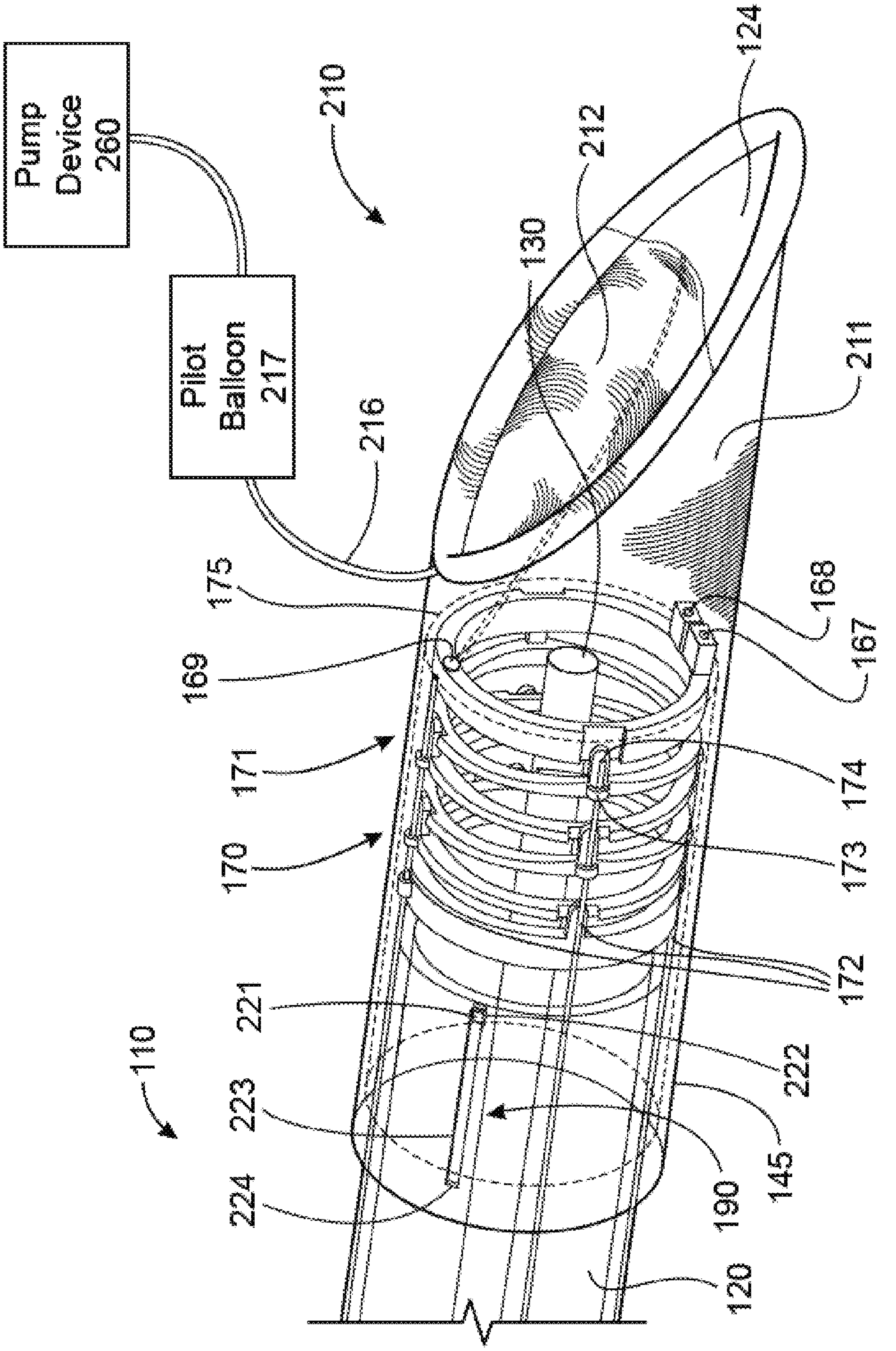
FIG. 7A displays a partial cutaway view of a hood body in a collapsed configuration in accordance with embodiments.

FIG. 7A displays a partial cutaway view of a hood body 212 in a collapsed configuration in accordance with embodiments. Inflatable bladder of hood body 212 may cover a portion of distal opening 124 when deflated. An upper end of hood body 212 may be affixed to one end of an inflation tube 216 that may run along an exterior surface of overtube 120. The other end of inflation tube 216 may be affixed to a pilot balloon 217 and a pump device 260 (FIG. 8) having a one-way valve that may feed air into inflatable bladder. When it is determined that device 110 is properly positioned within throat 214, an individual may use pump device 260 to inflate inflatable bladder so that it becomes rigid and concave in shape and pushes out the soft tissue from the hypopharynx and laryngeal vestibule 213 in throat 214, providing an airtight enclosure.

Figure 7B:
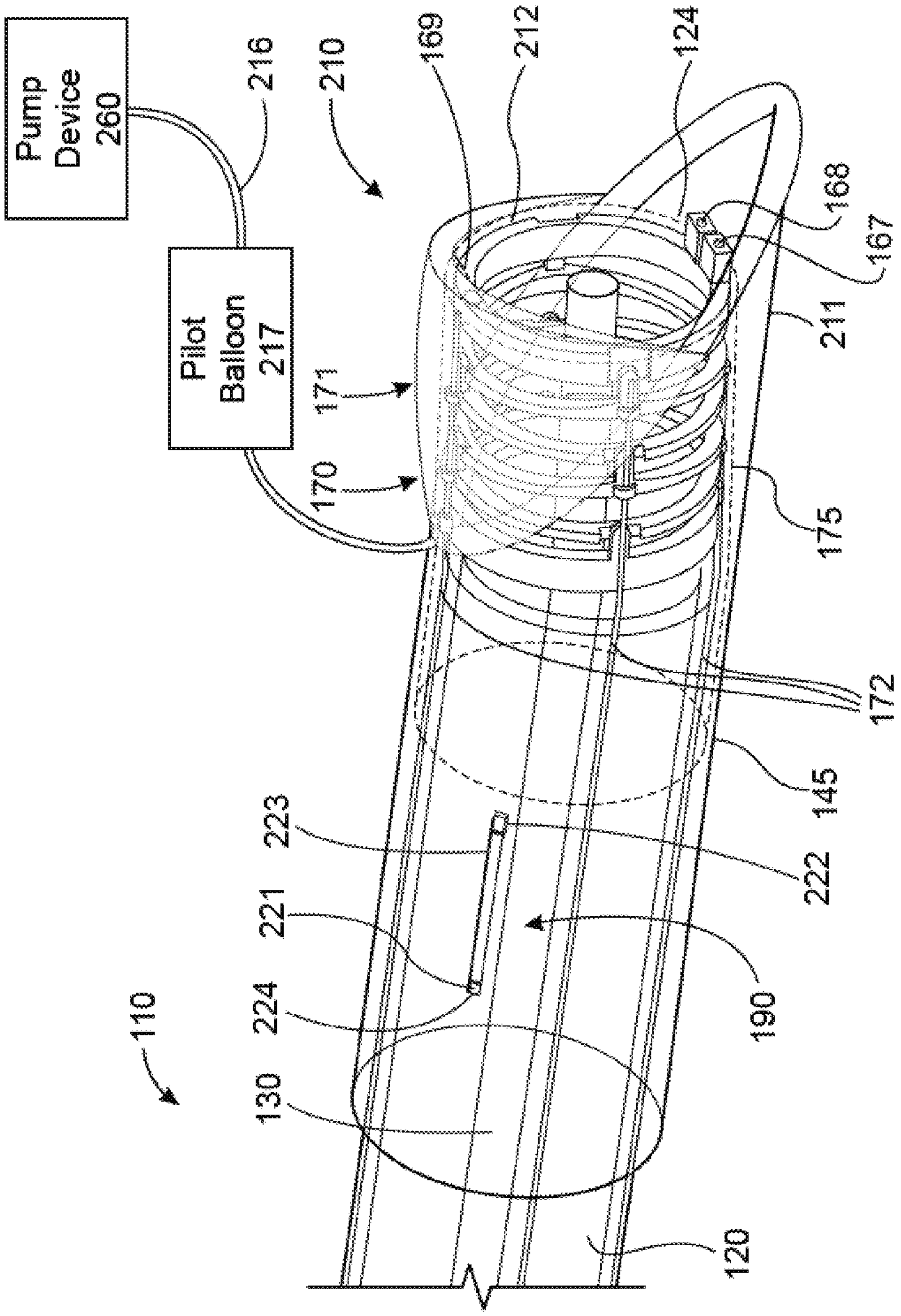
FIG. 7B displays a partial cutaway view of a hood body in an expanded configuration in accordance with embodiments.

As shown in FIG. 7B, when inflatable bladder is inflated/hood body 212 is expanded with tip director 169 being affixed to flexible tip 170 and hood body 212, one or more additional mechanisms may be triggered. In embodiments, tip director 169 may be at least one of a wire, an elastic cord, and an elastic polymer. The inflation of inflatable bladder may clear the soft tissue from the hypopharyngeal and laryngeal vestibule and may also automatically pull flexible tip 170 anteriorly and inferiorly and position flexible tip 170 at the laryngeal opening 213 of patient 105 and increases the likelihood of successful insertion of ETT 130 into the laryngeal opening 213. Flexible tip 170 may be pulled farther (along with overtube 120) in response to locking mechanism 190 being unlocked/in an unlocked position or state and in response to the expansion of hood body 212. In this case, stem 145 may be slidably attached to overtube 120 via the locking mechanism 190. As shown, a protrusion 221 affixed to the interior surface of stem 145 is pulled out of a pocket 222 positioned on the exterior surface of overtube 120 in response to the force exerted by the inflation of inflatable bladder on flexible tip 170 by way of tip director 169. Protrusion 221 is pulled along a path 223 (with a depth shallower than pocket 222) as flexible tip 170 and overtube 120 are pulled by hood body 212 until protrusion 221 hits wall 224 that is positioned at an end of path 223. In embodiments, device 110 may comprise this aforementioned embodiment of locking mechanism 190 in multiple areas around overtube 120 and 145. In certain embodiments, protrusion 221 may circumnavigate the interior surface of stem 145, while pocket 222, path 223, and wall 224 may circumnavigate the exterior surface of overtube 120 and may function similarly to the above described locking mechanism 190.

Figure 7C:
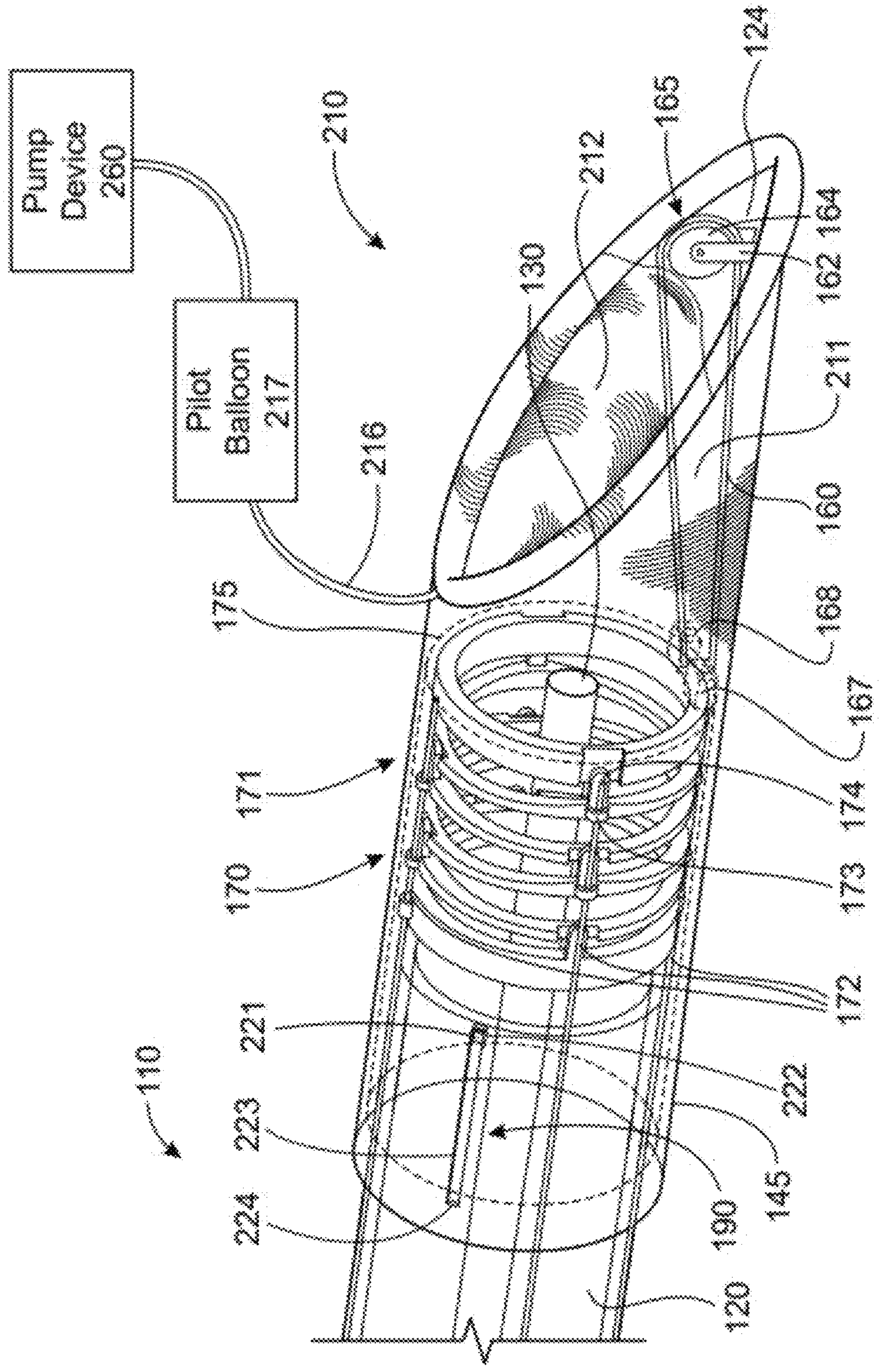
FIG. 7C displays a partial cutaway view of a hood body in a collapsed configuration including an alternative tip director in accordance with embodiments.

FIG. 7C displays a partial cutaway view of a hood body 212 in a collapsed configuration including an alternative tip director 165 in accordance with embodiments. Alternative tip director 165 may include pulley wire 160, pulley base 162, and pulley 164. Pulley wire 160 may, in embodiments, be the bottom wire 172 and may be positioned the same as the bottom wire 172. In other embodiments, pulley wire 160 may be positioned adjacent the bottom wire 172 and may be affixed to loops (similar to 173) or a covering on the exterior surface of overtube 120 or may exist freely of loops or guidance means. Pulley 164 may be affixed to hood base 211 via pulley base 162, which may be affixed to hood base 211 or may be integrated with hood base 211 as a single, integrated piece. It is noted that pulley wire 160 may be positioned along the underside of overtube 120 between overtube 120 and stem 145 so that alternative tip director 165 functions properly. In embodiments, pulley wire 160 may be at least one of a wire, an elastic cord, and an elastic polymer.

Figure 7D:
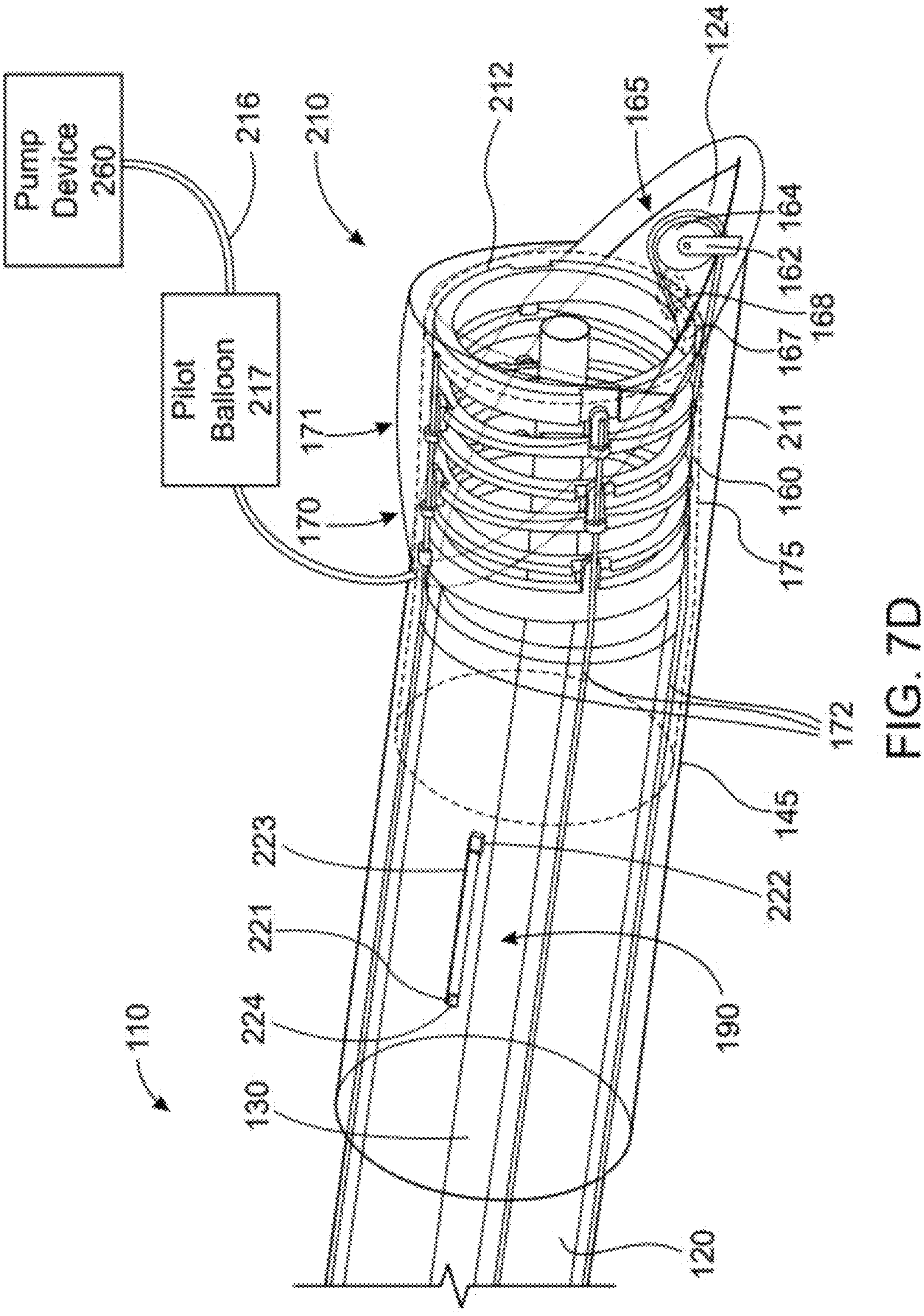
FIG. 7D displays a partial cutaway view of a hood body in an expanded configuration including an alternative tip director in accordance with embodiments.

As shown in FIG. 7D, the pulling forward of the flexible tip 170, in this embodiment, may be separate from the expansion of body 212 (which is what is used to pull flexible tip 170 forward in FIGS. 7A and 7B). In this embodiment, pulley wire 160 may be pulled toward the rear of overtube 120 via automatic or manual means (pulled by a user of device 110 or actuated via actuation module 200). The opposite end of pulley wire 160 may be affixed to the bottom front portion of flexible tip 170 (attached to the front disc 171). Once pulley wire 160 is pulled, it is wound around pulley 164 and simultaneously pulls flexible tip 170 anteriorly and inferiorly to position flexible tip 170 at the laryngeal opening 213 of patient 105 and increases the likelihood of successful insertion of ETT 130 into the laryngeal opening 213. It is noted that flexible tip 170 is able to be pulled anteriorly and inferiorly (as shown) due to the top of pulley 164 being positioned above the bottom of flexible tip 170 (where pulley wire 160 is affixed).

Positioning of the flexible tip 170 may occur once the expansion of hood body 212 is separately carried out to clear the soft tissue from the hypopharyngeal and laryngeal vestibule. Additionally, flexible tip 170 may be pulled farther (along with overtube 120) by alternative tip director 165 in response to locking mechanism 190 being unlocked/in an unlocked position or state an in response to the expansion of hood body 212.

In embodiments, locking mechanism 190 may be controlled via user input entered into control unit 270. User input for unlocking locking mechanism 190 may include the use of screens, buttons, switches, controls etc. Control unit 270 may receive the user input as gestures such as, but not limited to touch screen gestures and button/switch/control actuating. In other embodiments, locking mechanism 190 may comprise multiple configurations besides the protrusion-groove mechanism that may be easily conceived of by one skilled in the art. Other configurations may include, but are not limited to male-female engagement mechanisms, twist-lock mechanisms, threaded bearing mechanisms, and magnetic mechanisms. It is noted that in the case where locking mechanism 190 is controlled by user input, locking mechanism 190 may be unlocked prior to hood body 212 being expanded since the unlocking is not dependent on the expansion of hood body 212 in this case.

In embodiments, hood body 212 may be affixed to the free edge of hood base 211 (side walls of hood base 211) via one or more attachment means such as, but not limited to, adhesive, heat bonding, solvent bonding, and ultrasonic welding.

FIG. 8 displays a components diagram of an intubation device 110 in accordance with embodiments. Actuation module 200 may house one or more motors 250 affixed to one or more gears 255. The motors 250 and gears 255 in actuation module 200 may be utilized to move the flexible tip 170 using wires 172 as well as to actuate first chain 188 and second chain 198 to rotate first roller 181 of feeder mechanism 180 and to pull second roller 191 adjacent ETT 130. Power source 257 may be electrically connected to video monitor 140, camera 168, and light source 167 in order to provide power and have the video monitor 140, camera 168, and light source 167 function. Pump device 260 may be affixed to hood 210 via inflation tube 214 and may provide air to inflatable bladder for inflation. Pump device 260 may comprise devices such as, but not limited to, a hand pump, electric pump, a free syringe, etc. Control unit 270 may be electrically connected to power source 257 and at least one of actuation module 200, feeder mechanism 180, video monitor 140, pump device 260, camera 168, and light source 167. Control unit 270 may receive user input that may be translated into functions for the mentioned elements; these functions may include, but are not limited to: up, down, left, right, inflate, deflate, on, off, power up (scaled), power down (scaled), fast (scaled), and slow (scaled). In embodiments, user input may be input into control unit 270 via at least one of buttons and dials. Power source 257 may be electrically connected to at least one of control unit 270, actuation module 200, feeder mechanism 180, video monitor 140, pump device 260, camera 168, and light source 167 in order to provide electricity to these components. It is noted that FIG. 8 displays one or more embodiments of an intubation device 110; these embodiments may include one or more elements of this disclosure that are not found in FIG. 8.

Figure 9A:
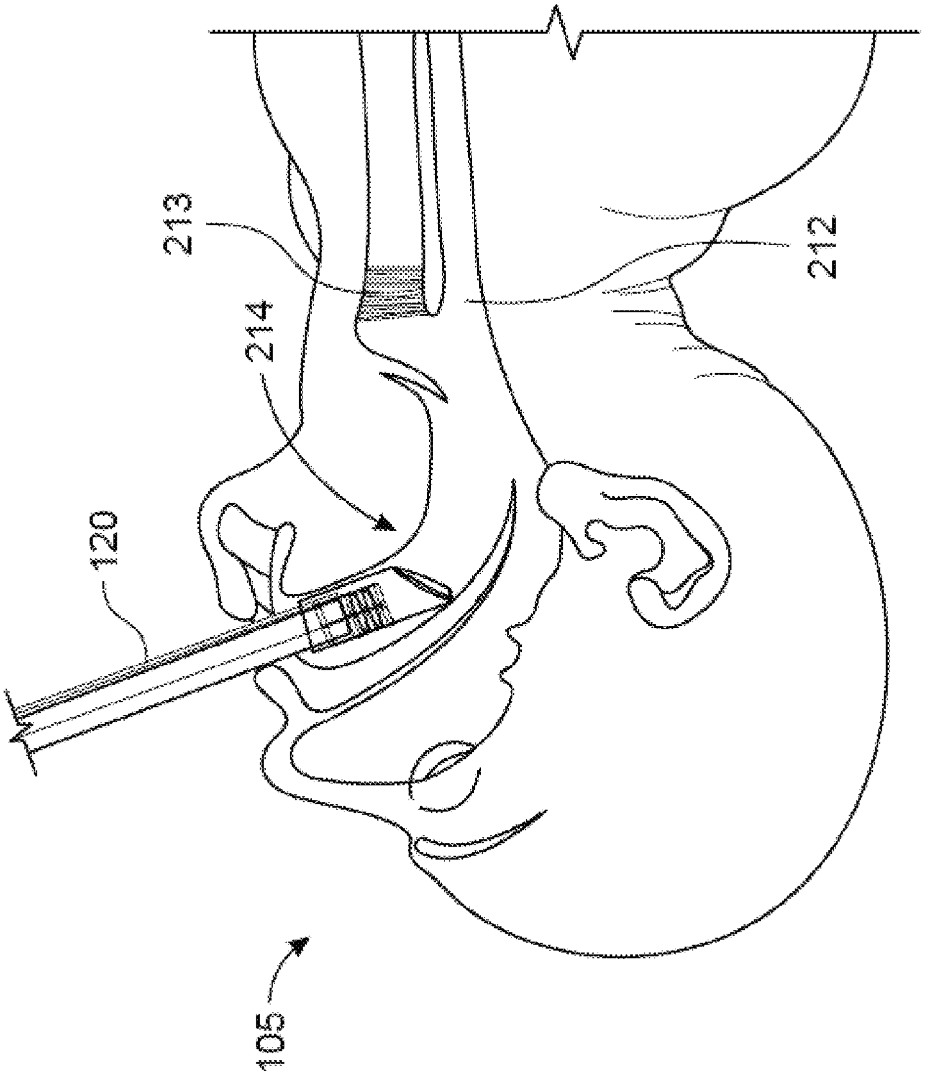
FIG. 9A displays an internal view of an intubation device partially inserted into a patient's throat in accordance with embodiments.
Figure 9B:
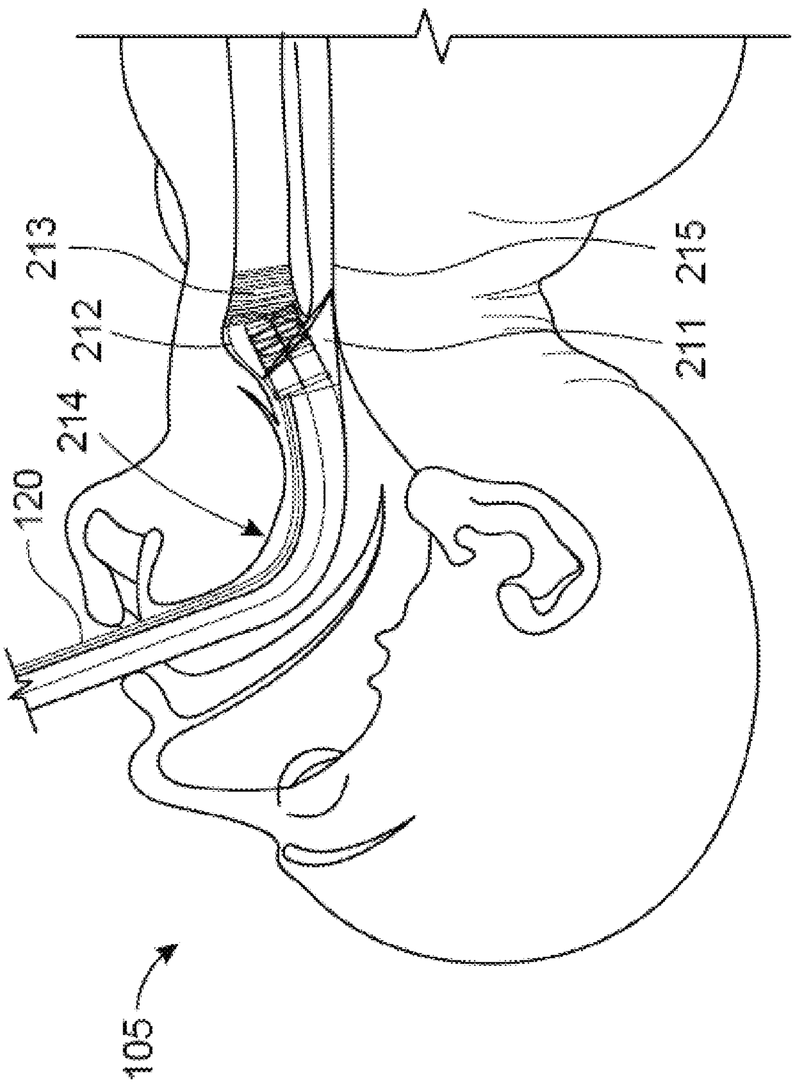
FIG. 9B displays an internal view of an intubation device fully inserted into a patient's throat in accordance with embodiments.

FIG. 9A displays an internal view of an intubation device 110 partially inserted into a patient's throat 214 in accordance with embodiments. When a patient 105 is not breathing and needs an ETT 130 inserted into their laryngeal opening 213, a distal end 121 of overtube 120 and flexible tip 170 may be inserted into the throat 214 of a patient 105. When in a proper position, hood base 211 may sit against the posterior hypopharyngeal wall with the esophageal seal occluding the esophageal inlet 215. As shown in FIG. 9B, hood body 212 may then be expanded, thus becoming rigid and is able to push out the soft tissue from the hypopharynx and laryngeal vestibule 213 in throat 214.

Figure 9C:
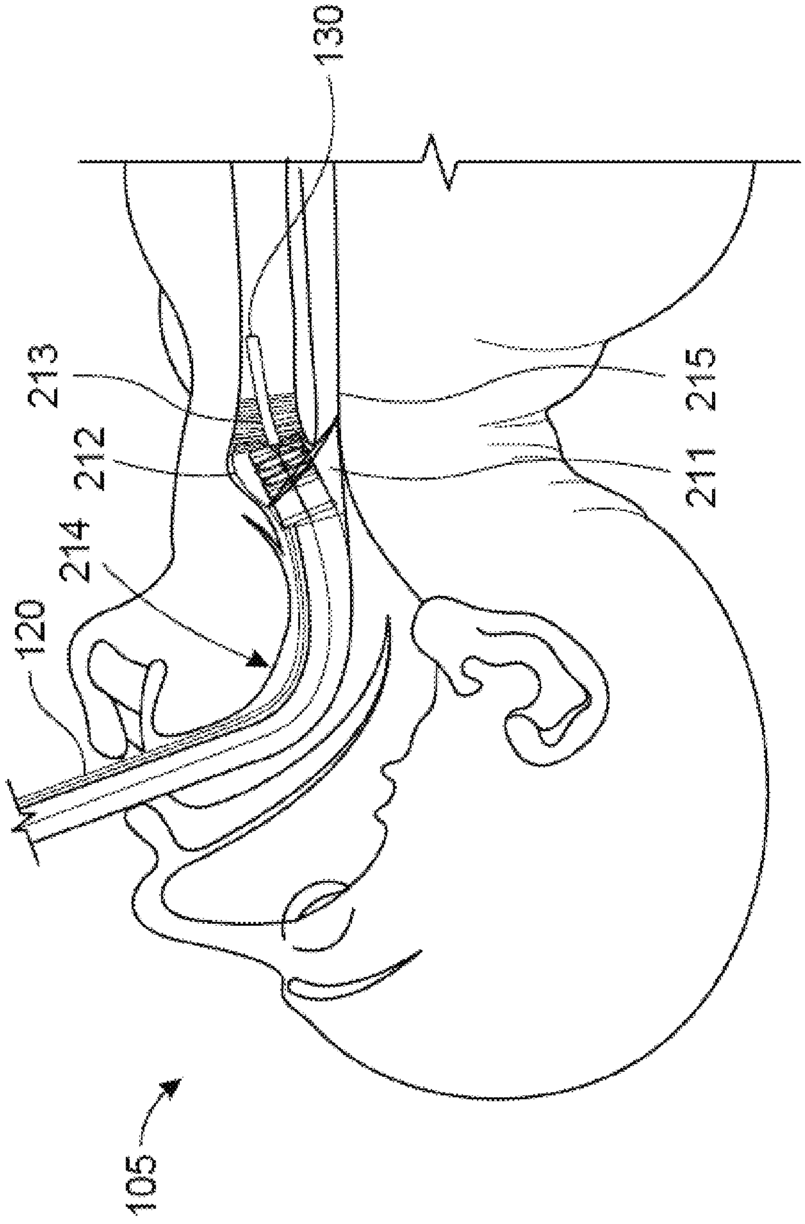
FIG. 9C displays an internal view of an intubation device fully inserted into a patient's throat with an ETT positioned in a larynx in accordance with embodiments.

When hood body 212 is expanded, flexible tip 170 may be automatically pulled anteriorly and inferiorly via tip director 169/alternative tip director 165 and may position flexible tip 170 (and ETT 130 positioned within flexible tip 170) at the laryngeal opening 213 of patient 105 and increases the likelihood of successful insertion of ETT 130 into the laryngeal opening 213 (see FIG. 9C). Additionally, when expanded, hood body may expand outwardly away from base 211 to push out the soft tissue from the hypopharynx and laryngeal vestibule 213 in the throat 214, clearing the visual pathway. In this position, hood body 212/inflatable bladder may provide an airtight seal so that the oxygen from ventilator 103 is directed into patient 105 rather than escaping out of the patient 105.

Camera 168 and light source 167 may be utilized to see if the ETT 130 is in a position to be fed into the laryngeal opening 213. If the ETT 130 is not optimally positioned, actuation module 200 may be utilized to adjust the lengths of wires 172 to move flexible tip 170, and thus ETT 130, into an optimal position to be fed into laryngeal opening 213.

Figure 10A:
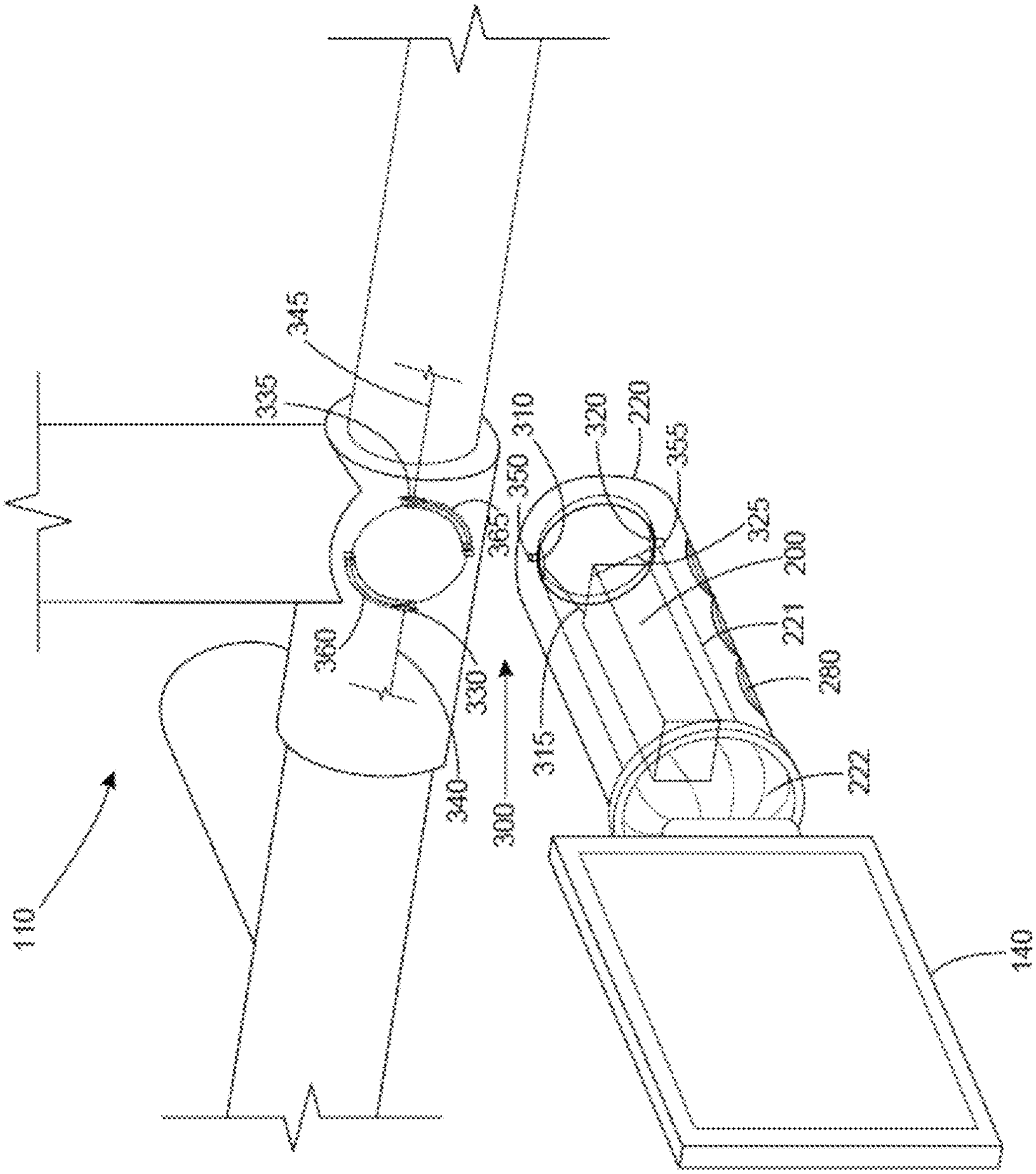
FIG. 10A displays a perspective view of a snap-twist locking mechanism in accordance with embodiments.

FIG. 10A displays a perspective view of a snap-twist locking mechanism 300 in accordance with embodiments. Handle 220 is shown detached from the rest of device 110. In this embodiment, handle 220 may be removably affixable to the rest of device 110 via a twist-locking mechanism 300 as shown. Twistlocking mechanism 300 may include first passage 360 and second passage 365 positioned internally inside of device 110. First and second passages 360,365 may each extend roughly 45 to 100 degrees. In order to provide a passage for a first and second protrusion 350,355 to a first and second conductive receiver 330,335. Handle 220 may include first protrusion 350 and second protrusion 355 which are affixed to first and second wire terminals 310,320, respectively. First and second wire terminals 310,320 may be positioned on an interior wall of handle 220 and may be affixed to first wire 315 and second wire 325, respectively. First and second wire 315,325 may also be affixed to power source 257 housed in actuation module 200 (positioned within interior section 230 of handle 220) of in order to supply electricity through the circuit that is created when handle 220 is properly affixed to the rest of device 110. In embodiments, handle 220 may also include control unit 270 (not depicted) that may also be positioned within interior section 230. On the distal end of handle 220 (opposite locking mechanism 300), video monitor 140 may be affixed to handle 220 via monitor retainer 232. In embodiments, video monitor 140 may be removably affixable to monitor retainer 232 via means such as, but not limited to threading, twist-lock engagement, O-ring attachment, magnetic attachment, form-fitting, and male-female engagement. In other embodiments, monitor retainer 232 may be removably affixable to handle 220 via means such as, but not limited to threading, twist-lock engagement, O-ring attachment, magnetic attachment, form-fitting, and male-female engagement; monitor retainer 232 may then be affixed to another portion of device 110.

Figure 10B:
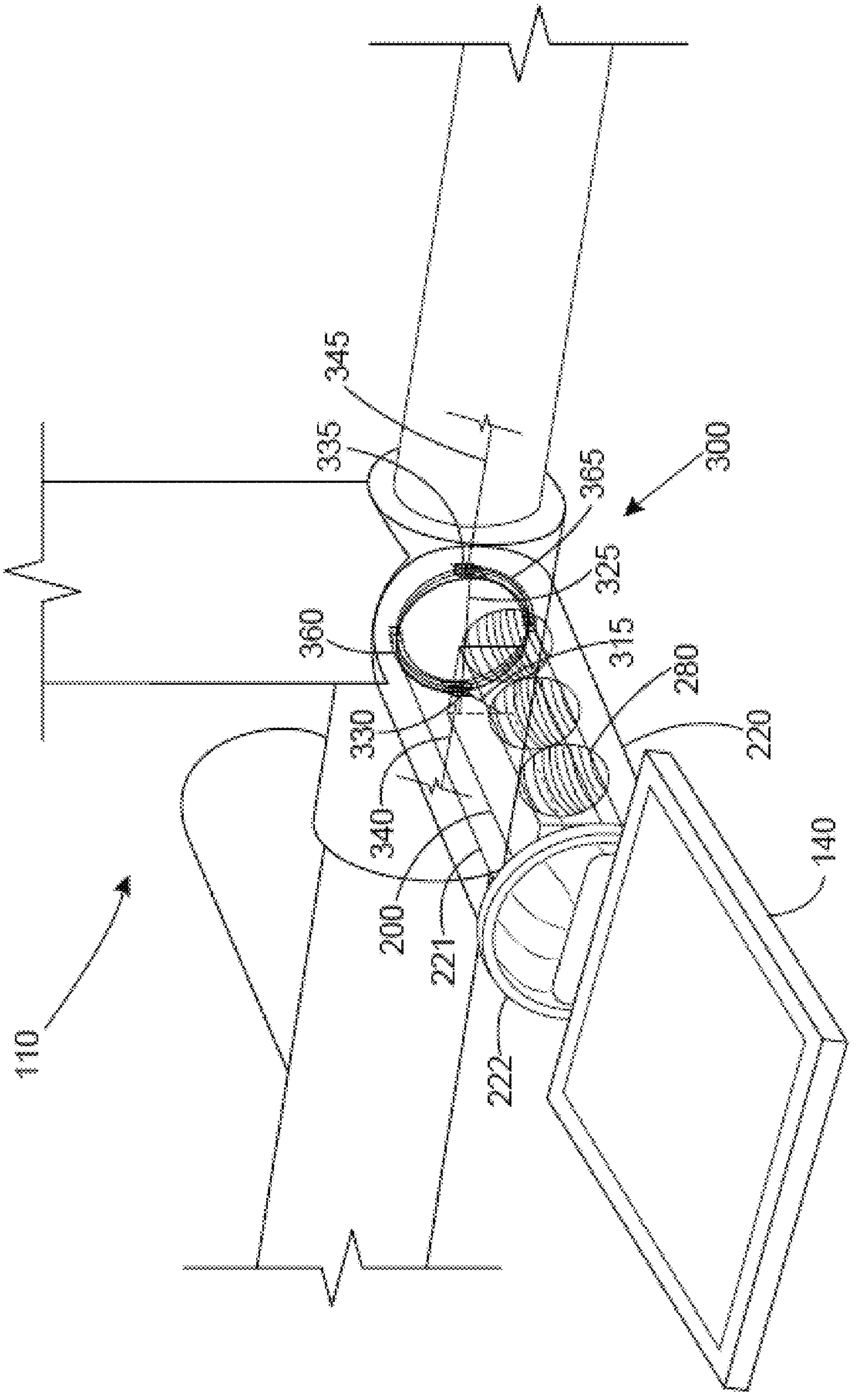
FIG. 10B displays a perspective view of a snap-twist locking mechanism completing a circuit in accordance with embodiments.

In order to close the circuit, first and second protrusions 350,355 of handle 220 are inserted into first and second passages 360,365. Once inserted, handle 220 is turned counterclockwise 45 to 100 degrees until first and second protrusions 350,355 contact first and second conductive receivers 330,335, as shown in FIG. 10B. First and second conductive receivers 330,335 may comprise a configuration for securely receiving first and second protrusions 350,355 such as, but not limited to an orifice and an indented shape. When this positioning is accomplished, the circuit between the handle 220 and the device 110 becomes closed and one or more motors (motor 250 or otherwise) contained in device 110 (in handle 220/actuation module 200 or in another part of device 110) may provide power to one or more of the aforementioned electric powered elements of device 110 (pending the use of any control switches) via third wire 340 and fourth wire 345 positioned in device 110. It is noted that when the circuit is closed, electricity is sent from power source 257 to one or more motors (motor 250 or otherwise) that may be positioned anywhere along/within device 110 and connected via third and fourth wires 340, 345. In order to keep the handle 220 contained within device 110, handle 220 may be secured using a male-female engagement mechanism with device 110 such as the mechanisms mentioned previously. In certain embodiments, first and second protrusions 350,355 may be spring-loaded in order for handle 220 to be more easily inserted into and/or removed from device 110.

In embodiments, the spring-loaded mechanism of first and second protrusions 350,355 may be controlled using trigger mechanism 280. It is noted that one skilled in the art can conceive of and create the components for using trigger mechanism 280 as an actuator for the spring-loaded mechanism of first and second protrusions 350,355. In other embodiments, trigger mechanism 280 may be used as a switch for the circuit of device 110. It is noted that one skilled in the art can conceive of and create the components for using trigger mechanism 280 as a switch for the circuit of device 110.

When handle 220 comprises actuation module 200 and/or power source 257, it is noted that handle 220 (and any components it contains) may be kept in a medical setting as a standard piece of equipment, while the rest of device 110 may be disposable (as a single-use product or a product that is only used a few times). In this embodiment, handle 220 may also include control unit 270.

Figure 11:
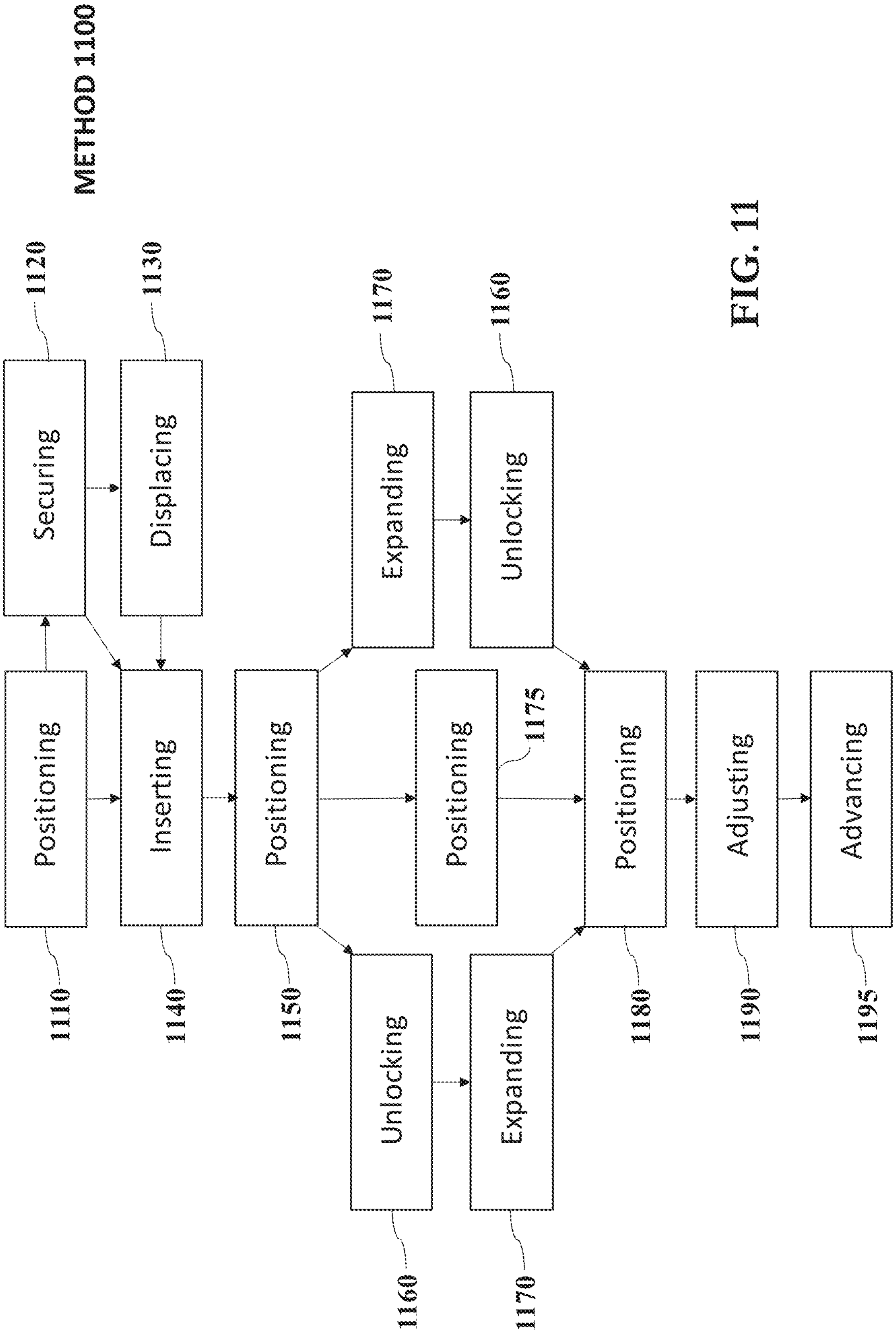
FIG. 11 displays a method for inserting an ETT into a patient's trachea in accordance with embodiments.

FIG. 11 displays a method 1100 for inserting an ETT 130 into the trachea of a patient 105 in accordance with embodiments. Method 1100 may comprise positioning 1110 an ETT 130 within an overtube 120. This may be carried out by inserting ETT 130 through either the proximal opening (actuation module orifice 123) or distal opening 124 (opening in hood 210) of the overtube 120 until the ETT 130 is completely inside overtube 120. Device 110 may then be inserted 1140 into a patient's throat 214. Once the device 110 is in the throat 214 of patient 105, device 110 may be moved down the throat 214 until flexible tip 170 of device 110 is positioned 1150 adjacent a patient's laryngeal opening 213. Locking mechanism 190 between hood 210 and overtube 120 may then be unlocked 1160, allowing overtube 120 to slide/advance within hood 210 (the unlocking 1160 may be carried out via user input entered into control unit 270). Hood body 212 is then expanded 1170 (via means previously discussed such as, in embodiments, via inflation tube 216). Since the anteroinferior portion of hood body 212 and the distal end 121 of overtube 120 are connected via tip director 169, hood body 212 pulls overtube 120 anteroinferiorly. The end result of this expanding 1170 motion is the positioning 1180 of flexible tip 170 at the laryngeal opening 213. In another embodiment, alternative tip director 165 is utilized to position 1175 the overtube adjacent the laryngeal opening 213. Thusly positioned overtube 120 may optionally be further adjusted 1190 via articulating function of the flexible portion of overtube 120 (extension and retraction of the plurality of wires 172). ETT 130 may then be advanced 1195 into the trachea through a plurality of means, such as, but not limited to any of the aforementioned feeder mechanisms 180.

In embodiments, method 1100 may include securing 1120 ETT 130 within the overtube 120 via a feeder mechanism 180 positioned within overtube 120 after the positioning 1110. The securing 1120 may further include laterally displacing 1130 a first roller 181 of the feeder mechanism 180 towards a second roller 191 of feeder mechanism 180 so that ETT 130 is secured within overtube 120.

In embodiments, method 1100 may comprise providing air to an end of the overtube 120 adjacent the laryngeal opening 213 via a ventilator The providing of air may be performed after the positioning 1150 of flexible tip 170 and may be performed if hood body 212 is inflatable (includes an inflatable bladder).

In other embodiments of method 1100, the unlocking 1160 may be dependent upon the expanding 1170 if a locking mechanism 190 not controlled by user input is utilized. In this case, locking mechanism 190 unlocks 1160 when tip director 169 is pulled due to the expanding 1170; expanding 1170 may therefore occur before the unlocking 1160.

Figure 12:
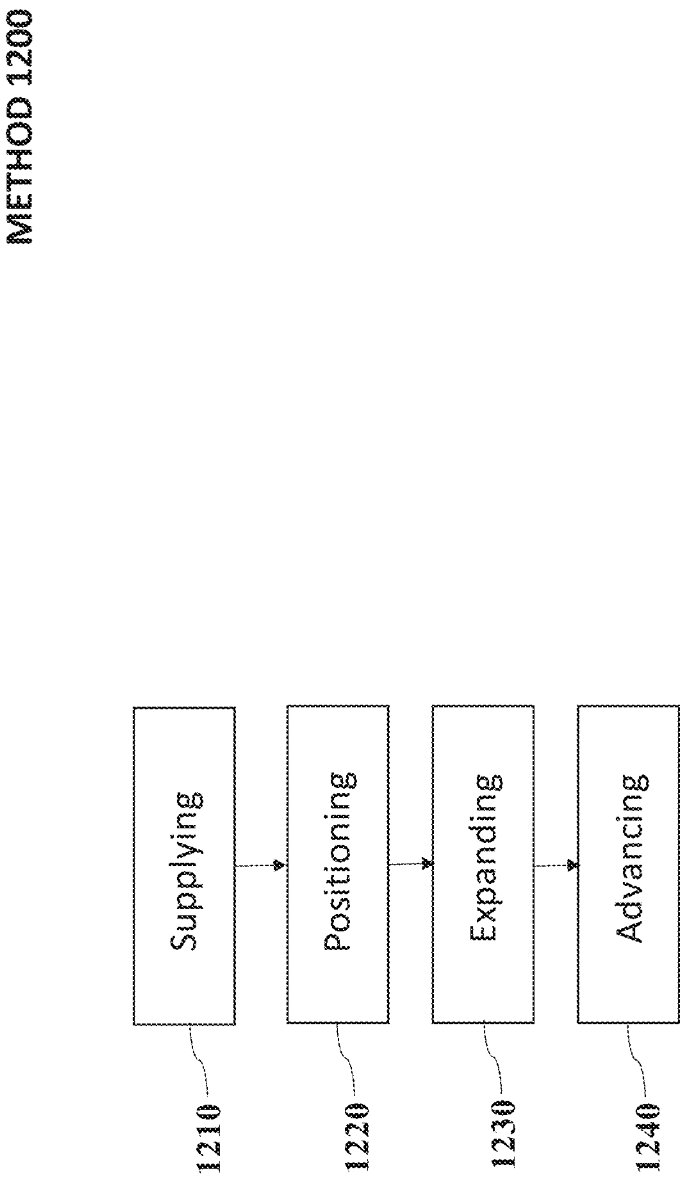
FIG. 12 displays a method for clearing soft tissue from a larynx and hypopharynx of a patient in accordance with embodiments.

FIG. 12 displays a method 1200 for clearing soft tissue from a larynx and hypopharynx of a patient 105 in accordance with embodiments. Method 1200 may utilize any of the aforementioned embodiments of device 110. Method 1200 may include supplying 1210 a device 110 having an overtube 120, an ETT 130 disposed in overtube 120, a hood 210 having an expandable hood body 212, and, in embodiments where the hood body 212 is inflatable, a pump device 260 and an inflation tube 216 connecting an inflatable bladder of hood body 212 and pump device 260. Device 110 may then be positioned 1220 in a throat 214 of a patient 105 adjacent the laryngeal opening 213. Hood body 212 may then be expanded 1230 (via means previously discussed such as, in embodiments, via inflation tube 216) and may become rigid and expand in a centrifugal manner in an environment adjacent the laryngeal opening 213. As the expansion 1230 occurs, the soft tissue of the larynx and hypopharynx may be pushed away from the line of vision of device 110, allowing space for advancement 1240 of ETT 130 into the trachea. Advancement 1240 of ETT 130 may occur through a plurality of means, such as, but not limited to any of the aforementioned feeder mechanisms 180.

It is noted that certain elements are not drawn to scale and it would be obvious to one skilled in the art how to amend the elements to be properly scaled in relation to other elements.

It is noted that the utilization of handle 220 adds increased stability to the removal process of removing device 110 from a patient's throat 214.

In any of the aforementioned embodiments, any wiring or wires 172 may be embedded within the thickness/wall of overtube 120 instead of being covered by flexible sheath 176.

In any of the aforementioned embodiments, gears 187, 197, 255 may not include cogs and may comprise a pulley structure. In other embodiments, the pully structure may include cogs in the grooved portion of the pulley structure. Additionally, in other embodiments, chains 188, 198 may instead comprise a wire-like structure. In other embodiments, the wirelike structure may include protrusions (similar to cogs) that may fit properly into any cogs on gears 187, 197, 255 and/or pulley structure.

For the purposes of this disclosure, the terms "hood 210" and "hood portion 210" may be synonymous. For the purposes of this disclosure, the terms "ETT 130" and "endotracheal tube 130" may be synonymous. For the purposes of this disclosure, the terms "wire 172" and "control wire 172" may be synonymous. For the purposes of this disclosure, the terms "malleable covering 175" and "covering 175" may be synonymous. For the purposes of this disclosure, the terms "inflatable bladder" and "bladder" may be synonymous. For the purposes of this disclosure, the terms "laryngeal opening 213" and "laryngeal vestibule 213" may be synonymous.

Figure 13:
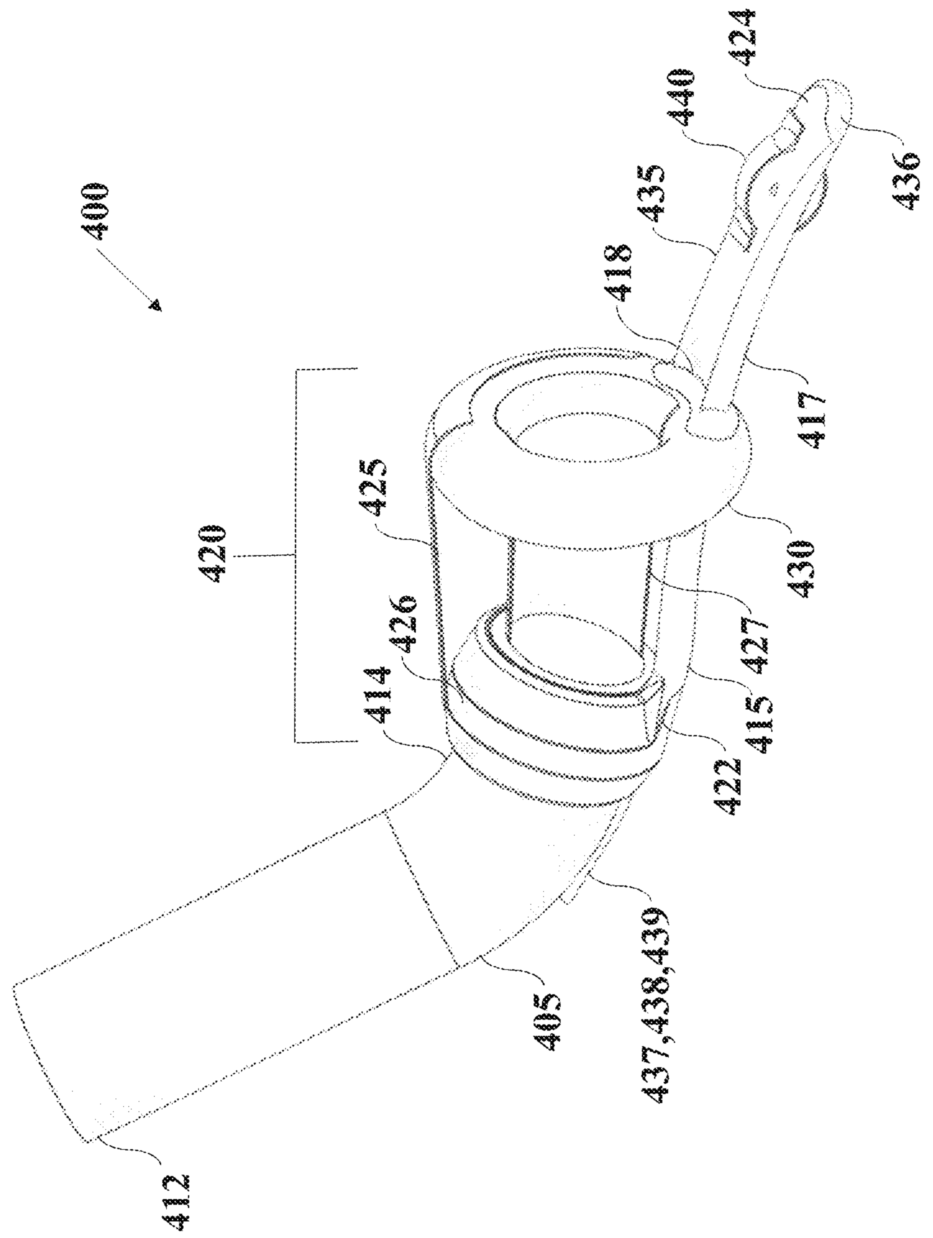
FIG. 13 displays a partial cross-sectional perspective view of an airway device, as shown and described herein.

FIG. 13 displays a partial cross-sectional perspective view of an airway device 400, as shown and described herein. As shown, a sheath 425 and inflatable esophageal obturator cuff 440 are partially depicted in order to effectively view all components of device 400. Device 400 includes an inflatable bladder 430 having an adaptable construction that may effectively deliver oxygenated air into a patient 402 (an individual in need of oxygenated support). The device 400 may further comprise an overtube 405, configured as a conduit, having a proximal and distal end 412, 414. Overtube 405 may be configured to deliver at least one of air, an ETT 410, and an endoscope 445 to a trachea 520 of the patient 402. As an exemplary embodiment that may be configured to carry out the previous functionality, overtube 405 may comprise a length of 15 centimeters and a diameter of 2 centimeters.

A mask section 415 attached to the distal end 414 of overtube 405 includes a spine section 417 having a proximal end 422 and a distal end 424 and an expandable body 420 disposed on a proximal portion of spine section 117. Expandable body 420 includes an inlet portion 426 disposed adjacent overtube 405 and an inflatable bladder 430 disposed about spine section 417 a distance from inlet portion 426. Spine section 417 passes through a second (lower) portion 432 of inflatable bladder 430 via spine orifice 418. Spine section 417 alternatively may pass anteriorly or posteriorly to the inflatable bladder 430. Inflatable bladder 430 additionally includes a shape and surface configured to seamlessly contact the circumference of the elliptical construction of the laryngeal opening 510 when mask section 415 is inserted into a patient's throat 530.

A sheath 425 of expandable body 420 spans along the spine section 417 from the inlet portion 426 to the inflatable bladder 430 to create a sealed environment between the inlet portion 426, inflatable bladder 430, and spine section 417. A tunnel section 427 disposed within sheath 425 extends from (and is proximally affixed to) inlet portion 426 to the inner surface of the inflatable bladder 430 to create a sealed (airtight) connection between the inlet portion 426 and the inflatable bladder 430 within the sheath 425. Mask section 415, when utilized within a patient's throat 530, is configured for sealing engagement with a laryngeal opening 510 of the patient 402 to create an unobstructed path into the trachea 520 of the patient 402. Additionally, the distal end 424 of spine section 417 includes an esophageal obturator 435 that protrudes from the distal end 424 of spine section 417 and includes a retroverted configuration configured to engage the hypopharynx/proximal esophagus and mitigate the device 400 from dislodging when the mask section 415 is positioned adjacent laryngeal opening 510 of the patient 402. Once lodged in the hypopharynx/proximal esophagus of patient 402, an inflated inflatable esophageal obturator cuff 440 affixed to a distal end 436 of the esophageal obturator 435 is configured to securely lodge the esophageal obturator 435 in hypopharynx/proximal esophagus of the patient 402.

It is noted that, as shown, three areas/components of device 400 are inflatable, allowing device 400 to efficiently and effectively function within a patient's throat 530. These areas/components include the volume of space within sheath 425 (excluding the inner volume of tunnel section 427), inflatable bladder 430, and inflatable esophageal obturator cuff 440. In order for these components to be inflated, a plurality of inflating tubes 437, 438, 439 extending along the length of overtube 405 (and portions of mask section 415) may provide air to each of the components. As shown, inflating tubes 437, 438, 439 may be positioned on an outer surface of device 400 but in other embodiments, inflating tubes 437, 438, 439 may be positioned within walls of device 400 or within an inner volume of device 400. It is further noted that the inner volume of tunnel section 427 may allow for gases to pass through, but may not specifically configured to receive an inflating tube for inflation purposes.

As designed, device 400 may precisely approximate the ellipsoid shape of laryngeal inlet 510 to produce occlusion using inflatable bladder 430 resting on top of laryngeal inlet 510. The anatomy-dictated design (also see FIGS. 15 and 16) of device 400 makes it possible for device 400 to be significantly smaller in all dimensions (length, width, height, and profile) when compared to conventional airway devices. In addition, the compact size and slimmer profile of device 400 should substantially enhance the insertion of device 400 into a patient 402. Furthermore, the design of device 400 avoids the application of undue pressure in undesirable locations, which is known to cause serious sequelae.

Figure 14A:
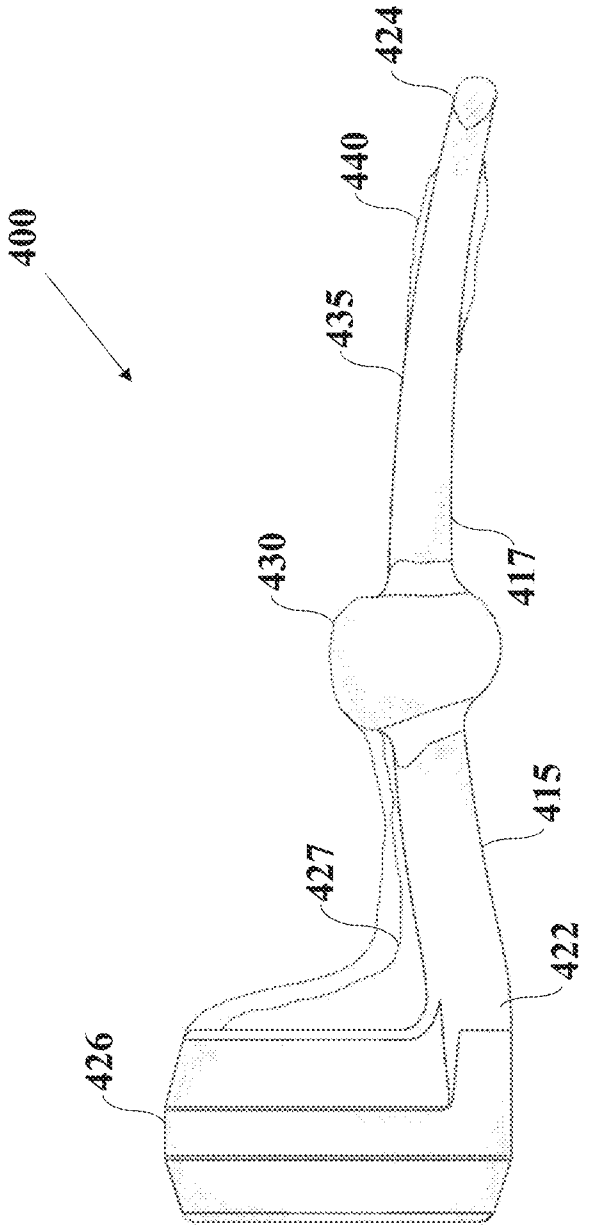
FIG. 14A displays a side view of an airway device illustrating a deflated mask section, as shown and described herein.
Figure 14B:
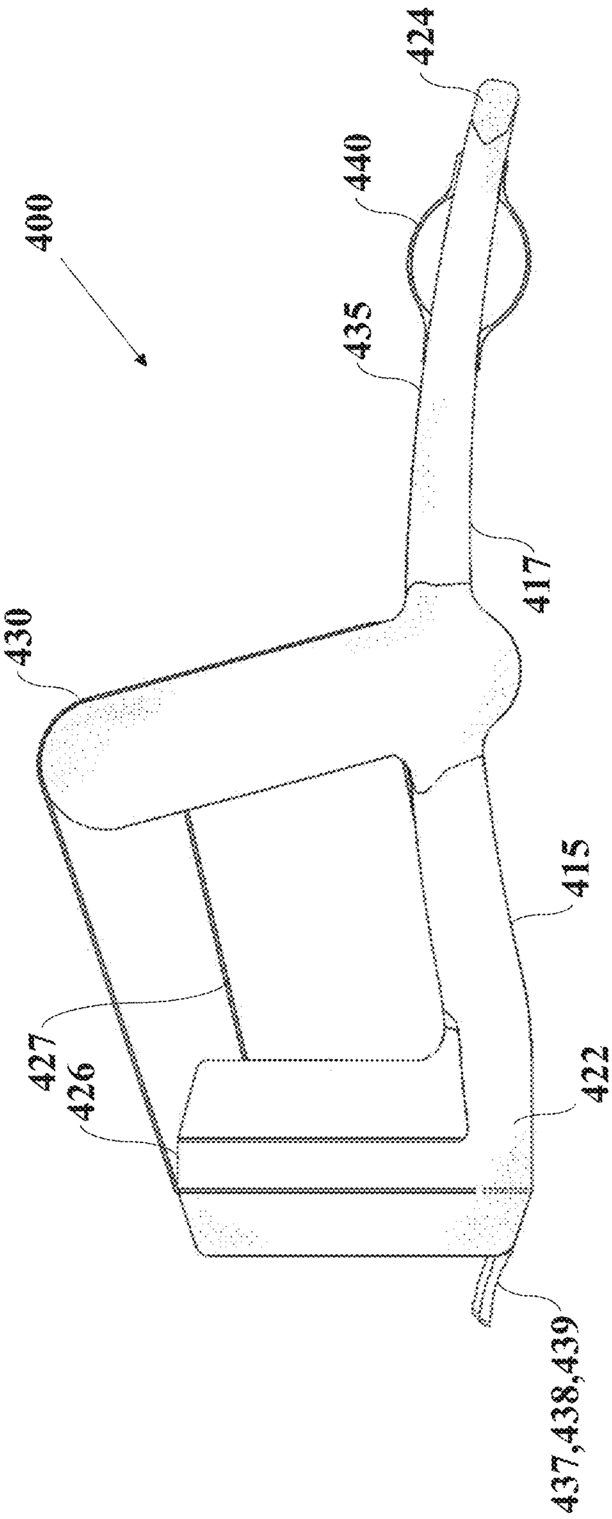
FIG. 14B displays a side view of an airway device illustrating an inflated mask section, as shown and described herein.

FIGS. 14A and 14B display side views of an inflated and deflated mask section 415, or mask section, of device 400, as shown and described herein. As shown, the configuration of mask section 415 may provide enhanced facility of introduction into a patient 402. Specifically, spine section 417 may allow this functionality to be carried out effectively. When mask section 415 is deflated, device 400 may be seamlessly guided into a patient's throat 530 to the patient's laryngeal opening 510, where mask section 430 may be inflated in order to create a sealed engagement with laryngeal opening 510 of a patient 402 so that an unobstructed path into the trachea 520 of the patient 402 is created.

As shown in FIGS. 14A and 14B (and as similarly presented in FIG. 13), mask section 415 includes a spine section 417 and an expandable body 420 disposed on a proximal portion of spine section 417. The expandable body 420 includes an inlet portion 426 disposed on a proximal end 422 of the spine section 417 that forms a contiguous structure with spine section 417. An inflatable bladder 430 disposed about spine section 417 is positioned a distance from the inlet portion 426 while a sheath 425 spans along spine section 417 from the inlet portion 426 to inflatable bladder 430. A tunnel section 427 disposed within sheath 425 may be affixed to inlet portion 426 proximally and inflatable bladder 430 distally and forms an airtight seal between inlet portion 426 and inflatable bladder 430. When inflated, mask section 415 is configured for sealing engagement with a laryngeal opening 510 of a patient 402 in order to create an unobstructed path into the trachea 520 of the patient 402. Mask section 415 is further configured to conform to the tissue structure circumferentially in the hypopharynx adjacent a laryngeal opening 510 of the patient 402 when mask section 415 is in an inflated state. It is noted that "inflated" or "inflated state" (when referring to mask section 415) may refer to mask section 415 including at least one of sheath 425, inflatable bladder 430, and inflatable esophageal obturator cuff 440 in an inflated state.

Additionally, the distal end 424 of spine section 417 includes an esophageal obturator 435 that protrudes from the distal end 424 of spine section 417 and includes an inflatable esophageal obturator cuff 440 affixed to a distal end 436 of esophageal obturator 135. When inflated, inflatable esophageal obturator cuff 440 may be configured to securely lodge esophageal obturator 435 in an esophagus 550 of patient 402. Once lodged in the esophagus 550, esophageal obturator 435 and an inflated inflatable esophageal obturator cuff 440 may provide a secure engagement of the airway device 400 within the patient's throat 415 when positioned in a hypopharynx/proximal esophagus of the patient 402. It is noted that a proximal portion of mask section 415 may rest against the body (as opposed to the free superior edge) of the epiglottis of patient 402 where the AE (aryepiglottic) folds connect with the epiglottis. In this location, the epiglottis firmly attaches to the thyroid cartilage, thus, a secure seal can be achieved when mask section 415 is in sealed engagement with laryngeal opening 510 of patient 402.

As further shown in FIGS. 14A and 14B, an esophageal obturator 435 may protrude from the distal end 424 of spine section 417. The retroverted configuration of spine section 417 may be configured to more effectively guide the esophageal obdurator 435 into the hypopharynx/proximal esophagus of the patient 402 as well as engage a dorsal surface 560 of the patient's esophagus 550 to increase stability to the mask section 415 when mask section 415 is positioned adjacent laryngeal opening 510 of patient 402. In order to securely lodge esophageal obturator 435 in an esophagus 550 of patient 402, distal end 436 of esophageal obturator 435 may include an inflatable esophageal obturator cuff 440 configured to effectively carry out said function. In certain embodiments, inflatable bladder 430 may be positioned at a fixed, negative inclination angle 433 in the range of 15 to 35 degrees from a "tire angle" (as defined in SAE J670), which is orthogonal from the anchor point 434 of inflatable bladder 430 so that inflatable bladder 430 is provided increased adaptability to aryepiglottic folds of patient 402.

Figure 15:
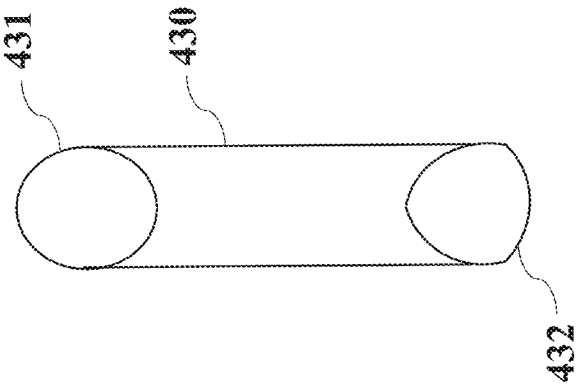
FIG. 15 displays a cross-sectional view of an inflatable bladder of a airway device, as shown and described herein.
Figure 16:
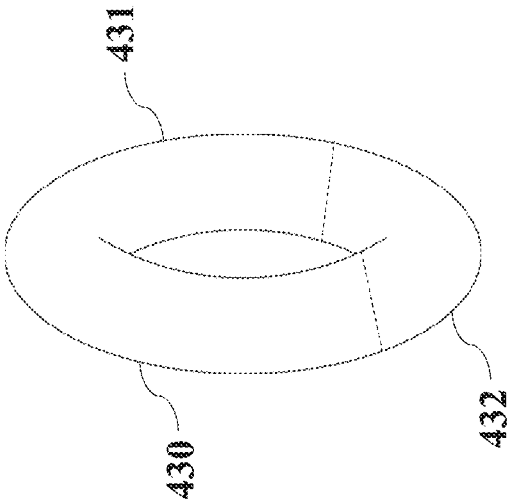
FIG. 16 displays a segmented view of an inflatable bladder of an airway device embodying a plurality of physical configurations, as shown and described herein.
Figure 17A:
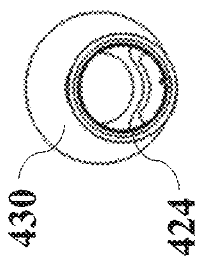
FIG. 17A displays a perspective view of a portion of an airway device mask section, as shown and described herein.
Figure 17B:
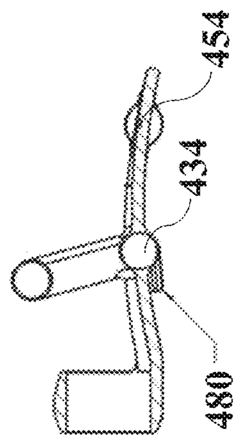
FIG. 17B displays a cross-sectional view of a portion of an airway device mask section, as shown and described herein.
Figure 17C:
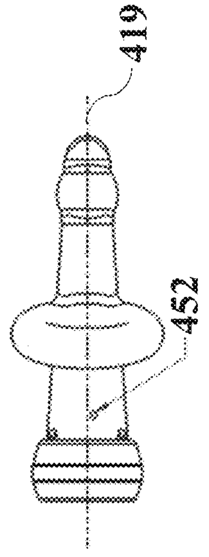
FIG. 17C displays a top view of a portion of an airway device mask section, as shown and described herein.
Figure 17D:
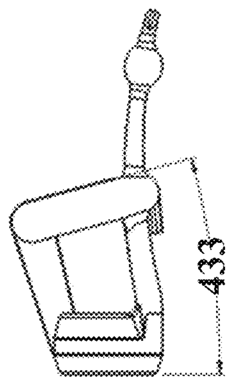
FIG. 17D displays a side view of a portion of an airway device mask section, as shown and described herein.
Figure 17E:
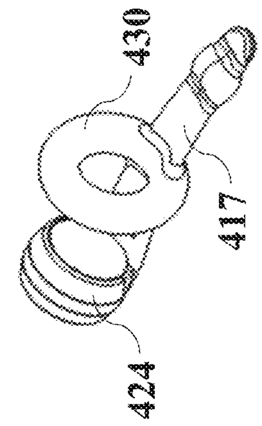
FIG. 17E displays a rear view of a portion of an airway device mask section, as shown and described herein.
Figure 17F:
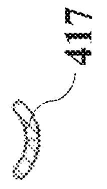
FIG. 17F displays a cross-sectional view of a spine section of a airway device, as shown and described herein.

FIG. 15 displays a cross-sectional view of an inflatable bladder 430 of an airway device 400, as shown and described herein. As shown, inflatable bladder 430 is configured to conform to at least two tissue structures adjacent the laryngeal opening 510 of patient 402 when the inflatable bladder 430 is in an inflated state by providing an anatomically inverse construction (in relation to laryngeal opening 510). This may be carried out efficiently due to the multiple surface configurations incorporated into the design of inflatable bladder 430. In the embodiment shown in FIG. 15, a first portion 431 of inflatable bladder 430 may include a first surface configuration configured to conform to a first tissue structure adjacent laryngeal opening 510 and a second portion 432 of inflatable bladder 430 may include a second surface configuration configured to conform to a second tissue structure adjacent laryngeal opening 510 when inflatable bladder 430 is in an inflated state. A specific embodiment of inflatable bladder 130 shown in FIG. 16. includes a first portion 431 making up substantially 260 to 315 degrees of an anterior of the inflatable bladder 430 and a second portion 432 making up substantially 45 to 100 degrees of a posterior of the inflatable bladder 430. First portion 431, as shown, comprises an elliptical shape/cross-section (but may also comprise a circular shape/cross-section in other embodiments) that may be positioned anterior to the inflatable bladder's 430 attachment to the spine section 417 and is adapted for effective sealed engagement with aryepiglottic folds of patient 402 while second portion 432 comprises a curvilinear shape/cross-section that may be positioned posterior to the inflatable bladder's 430 attachment to the spine section 417 and is adapted for effective sealed engagement with the interarytenoid fold of patient 402. In further embodiments, inflatable bladder 430 may comprise a single shape/cross-section that may include, but is not limited to, an elliptical shape/cross-section, a circular shape/cross-section, and a curvilinear shape/cross-section.

In embodiments, the body of inflatable bladder 430 may not include spine orifice 418 and may instead include a contiguous outer surface similar to the rest of the body of inflatable bladder 430 (a full body around the circumference of inflatable bladder 430). This configuration of inflatable bladder 430 may be configured to be positioned on top of or below spine section 417. In this case, spine section 417 may include a divot (on a top or bottom surface of spine section 417) configured to comfortably receive inflatable bladder 430.

FIGS. 17A-17F display various views of a portion of an airway device mask section 415, as shown and described herein. As shown, inlet portion 426 and spine section 417 may be constructed as a single, contiguous piece. First and second tube orifices 452, 454 extend from the lower surface of spine section 417 to the upper surface of spine section 417 so that one of the first, second, and third inflating tubes 437, 438, 439 may provide air to the interior volume of sheath 425 and another of the first, second, and third inflating tubes 437, 438, 439 may be affixed to inflatable bladder 430 in order to provide air to inflatable bladder 430. First and second tube orifices 452, 454 extend from a lower surface of spine section 417 to an upper surface of spine section 417 in order to provide pathways of delivery for air to expandable body 420 and inflatable esophageal obturator cuff 440. It is noted that the plurality of inflating tubes 437, 438, 439 may run along the length of spine section 417 parallel with spine axis 419.

An anchor point 434 is shown adjacent the apex of the curvature of spine section 117 and includes an indented configuration for effective attachment of inflatable bladder 130. A mid-portion of spine section 117 (FIGS. 17B, 17D, and 17F) includes a convexity having a radius, in embodiments, between 100 and 500 millimeters. The proximal end 422 of spine section 417, in embodiments, may converge with a lower section of inlet portion 426 in a direction along the curvature of spine section 417 while in other embodiments, spine section 417 may converge with lower section of inlet portion 426 at a 90-degree angle to the height of inlet portion 426. It is noted that the configuration of spine section 417 having a dorsal convexity may lessen the mask section's 415 anteriorly directed movement tendency toward the laryngeal opening 510 and may instead allow spine section 417 to proceed in a more favorable inferior trajectory toward the esophagus 550. A collection pouch 480 is positioned adjacent second portion 432 of inflatable bladder 430 so that when device 400 is positioned within a patient's throat 530, phlegm and other nasal congestion may be effectively trapped, leading to a more effective and less disturbed anchoring of device 400 within the patient's throat 530. In embodiments, spine section 417 may comprise a length ranging between 50 millimeters and 120 millimeters, a width ranging between 5 millimeters and 20 millimeters, and a thickness ranging between 1 millimeter and 10 millimeters.

Figure 18A:
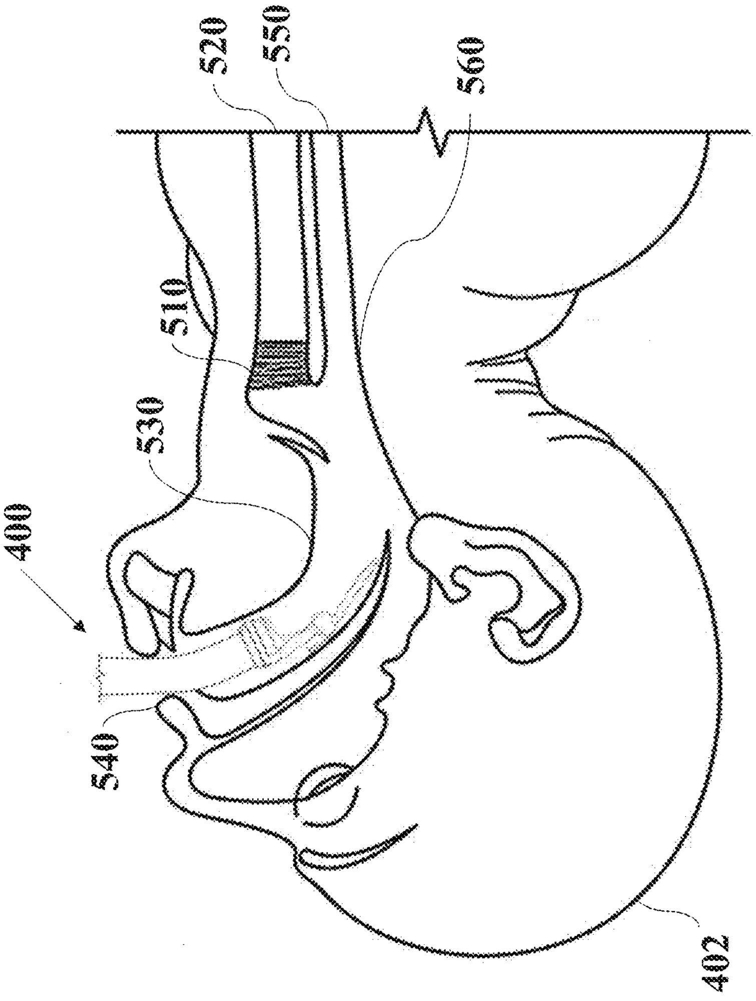
FIG. 18A displays an internal view of an airway device partially inserted into a patient's throat, as shown and described herein.
Figure 18B:
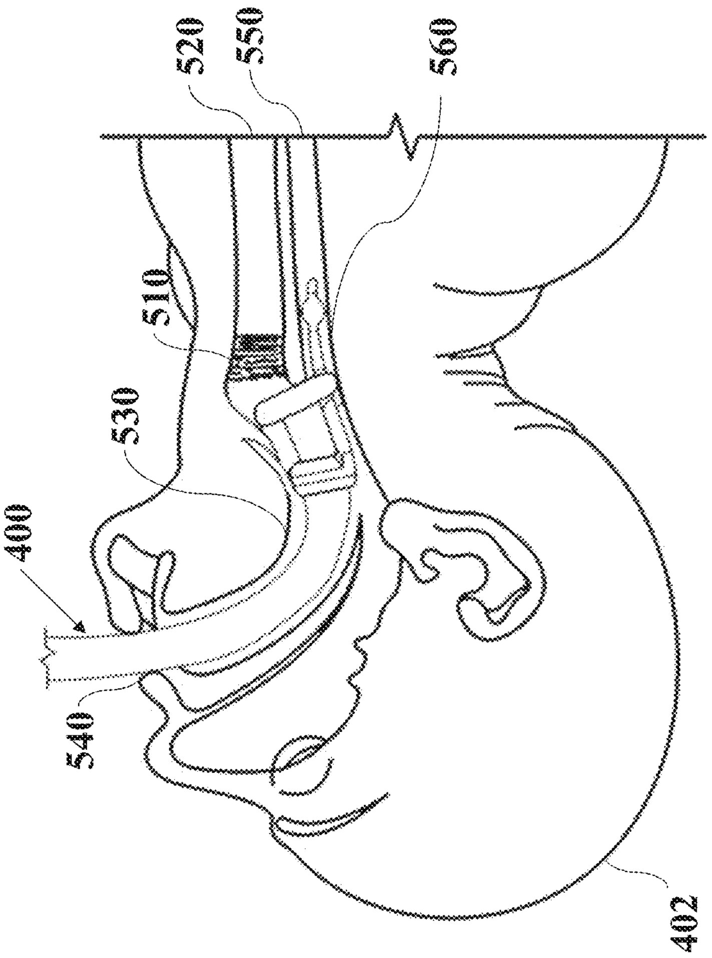
FIG. 18B displays an internal view of an inflated airway device fully inserted into a patient's throat, as shown and described herein.
Figure 18C:
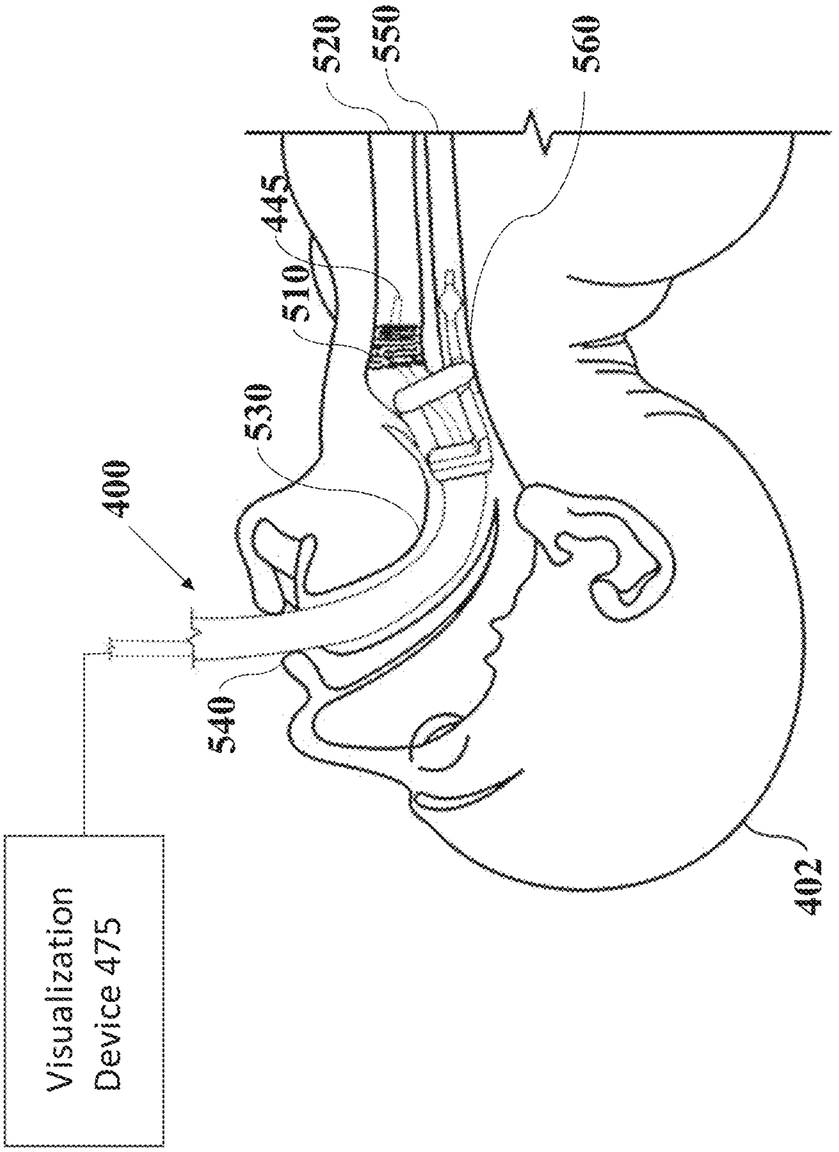
FIG. 18C displays an internal view of an inflated airway device fully inserted into a patient's throat with an endoscope partially positioned in a trachea of the patient, as shown and described herein.
Figure 18D:
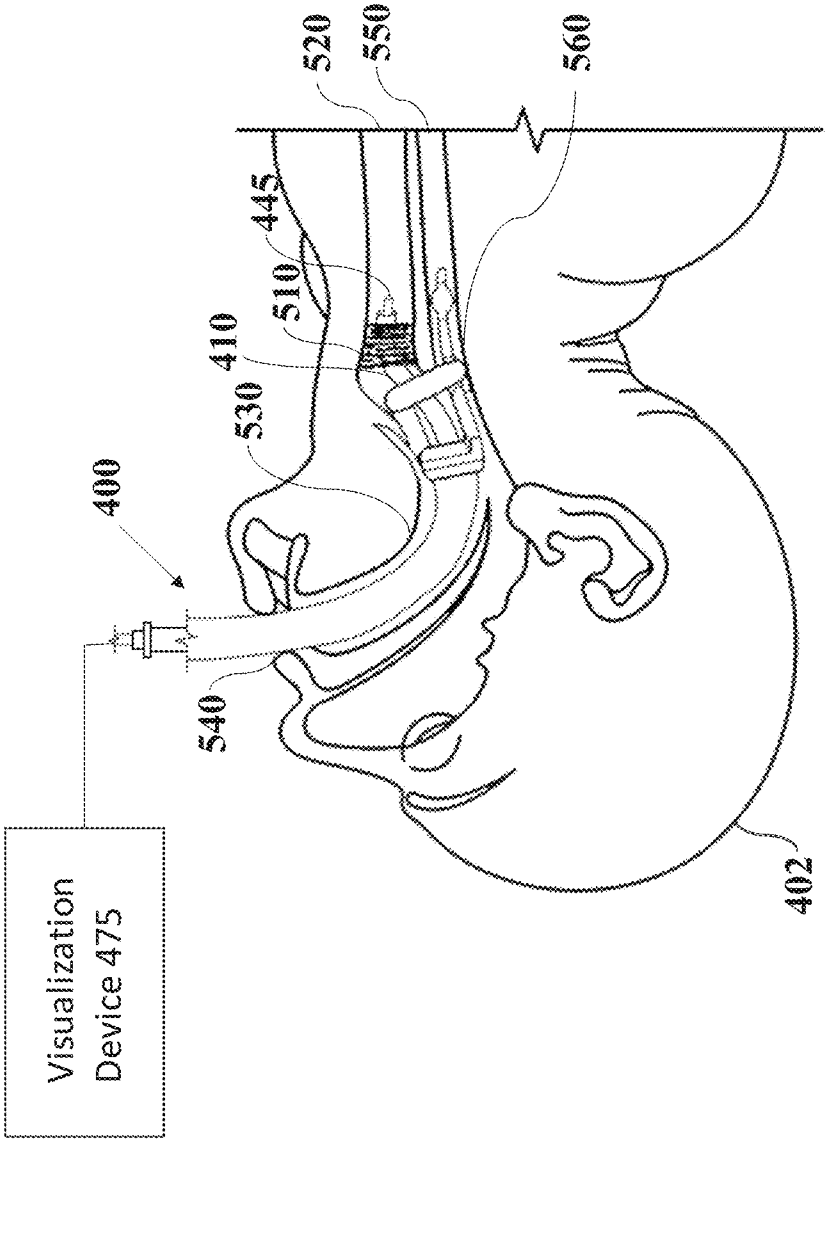
FIG. 18D displays an internal view of an inflated airway device fully inserted into a patient's throat additionally with an ETT partially positioned in a trachea of the patient, as shown and described herein.
Figure 18E:
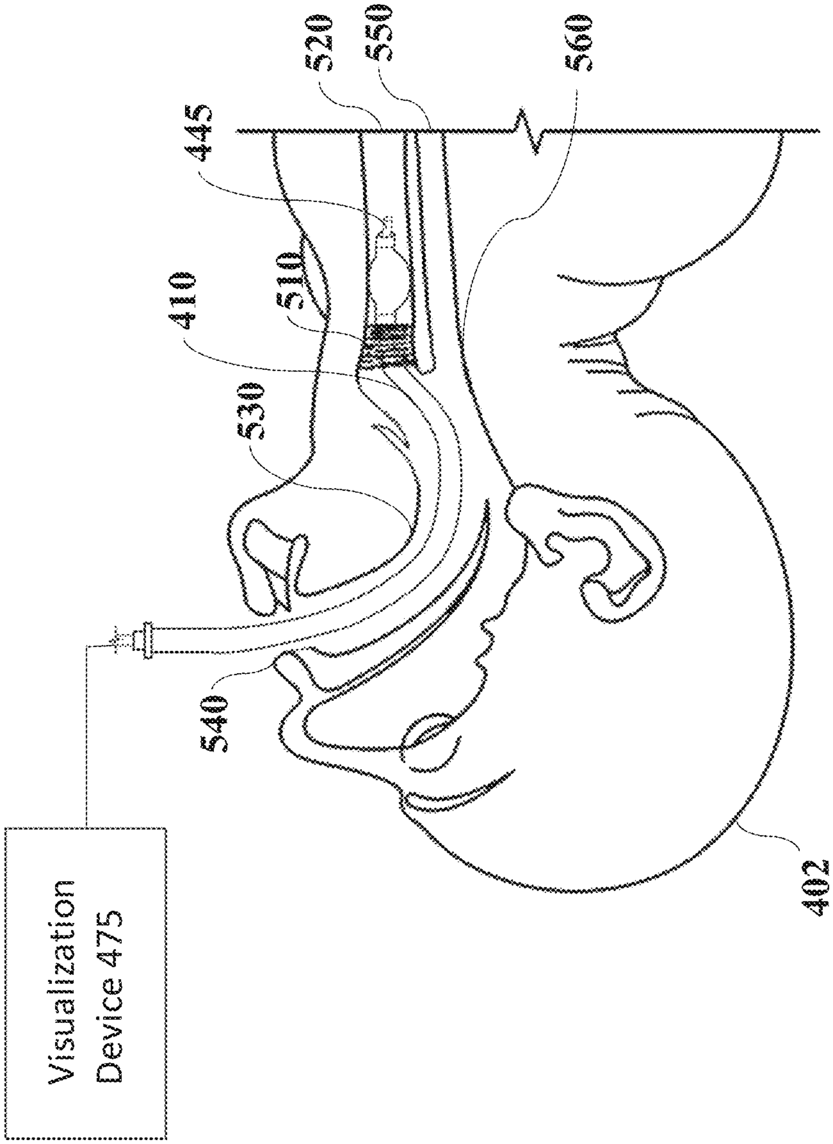
FIG. 18E displays an internal view of an airway device partially removed from a patient's throat, as shown and described herein.
Figure 18F:
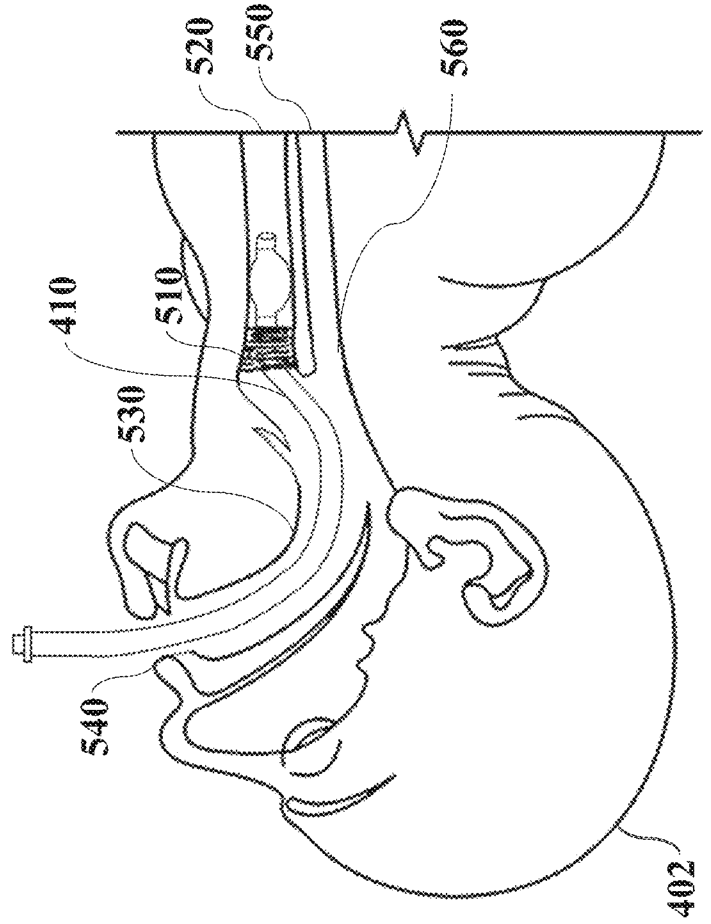
FIG. 18F displays an internal view of an ETT remaining in a patient's throat, as shown and described herein.
Figure 21:
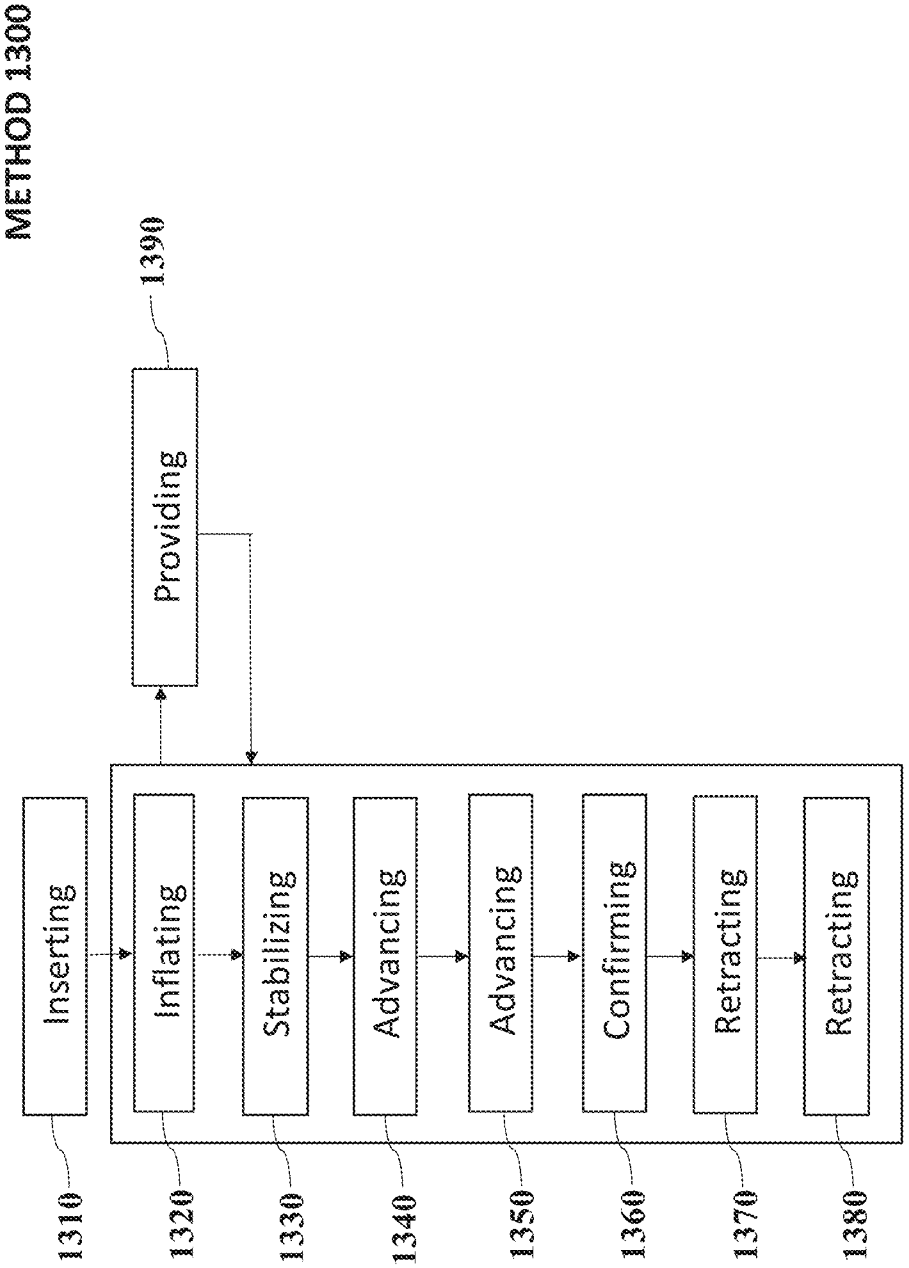
FIG. 21 displays a method for intubating a patient, as shown and described herein.

FIG. 21 displays a method 1300 for intubating a patient 402, as shown and described herein. Method 1300, unless otherwise noted, may utilize an airway device 400 similar to any of the embodiments of device 400 disclosed. The steps of method 1300 may additionally be illustrated via FIGS. 18A-18F. As shown in FIG. 18A, an airway device 400 may be partially inserted 1310 into a patient's throat 530. Once inserted 1310, inflatable bladder 430 of the device 400 may be inflated 1320 (FIG. 18B) in order to form an airtight seal around a laryngeal opening 510 of patient 402.

Once inflatable bladder 430 is inflated and positioned adjacent laryngeal opening 510, enhanced sealing properties may be created so that the axis of airflow entering device 400 matches the axis of the trachea 520, allowing for improved delivery of oxygenated air into the patient's 402 lungs. Furthermore, inflatable bladder 430 may be stabilized 1330 adjacent the laryngeal opening 510 of the patient 402 via lodging of an esophageal obturator 435 and an inflated inflatable esophageal obturator cuff 440 of spine section 417 in the esophagus 550 (hypopharynx/proximal esophagus) of patient 402. The lodging of an esophageal obturator 435 and an inflated inflatable esophageal obturator cuff 440 of spine section 417 may additionally secure engagement of the airway device 400. Once the inflatable bladder is stabilized 1330, an endoscope 445 may then be advanced 1340 (FIG. 18C) through mask section 415 of airway device 400 and into the trachea 520 of patient 402. Endoscope 445 may include a light and a camera (not depicted) affixed to a visualization device 475 so that a provider of device 400 (such as a doctor) may view the interior of patient 402. Subsequently, an ETT 410 may be advanced 1350 (FIG. 18D) along endoscope 445 and into the trachea 520 of patient 402. At this point, the user of device 400 may confirm 1360 ETT 410 is at least partially positioned within the trachea 520 of the patient 402 via the light, camera, and visualization device 475 associated with endoscope 445.

Overtube 405/airway device 400 may then be retracted 1370 (FIG. 18E) from the throat 530 of the patient 402 until the overtube 405/airway device 400 is fully removed from the throat 530 and mouth of the patient 402. Endoscope 445 may then also be retracted 1380 (FIG. 18F) from the throat 530 of the patient 402 until the endoscope 445 is fully removed from the throat 530 and mouth of the patient 402 and only the ETT 410 remains. It is noted that ventilation may be continuously provided 1390 to the patient 402 starting at the inflating 1310 so that the patient 402 remains alive or in stable condition. The ventilation may be supplied by any means or machine known in the art such as, but not limited to, ventilators.

It is noted that in embodiments, endoscope 445 may be detached from visualization device 475 so that components such as, but not limited to airway device 400 and ETT 410, may be slid in and out of patient 402 around/along the length of endoscope 445 (so that the components may be effectively added or removed).

Figure 19:
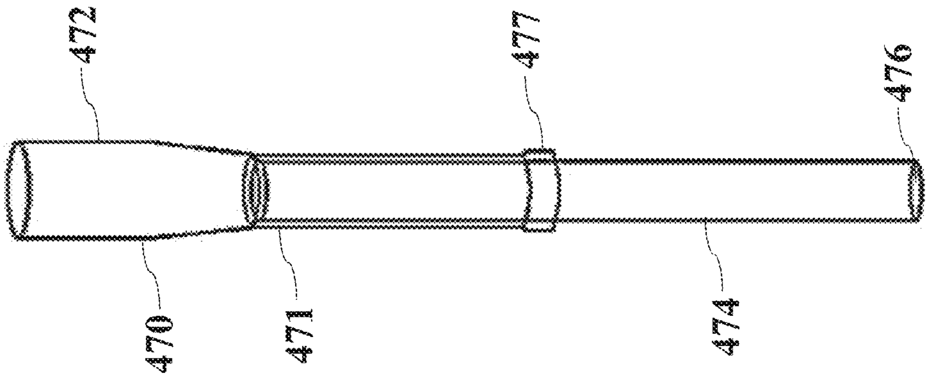
FIG. 19 displays a perspective view of a telescopic intubating pole utilized with an airway device, as shown and described herein.

FIG. 19 displays a perspective view of a telescopic intubating pole 470 utilized with an airway device 400, as shown and described herein. Intubating pole 470, as shown, includes an elongatable body 471 having a proximal portion 472 and a distal portion 474 (shown partially disposed within proximal portion 472). An upper receptacle 473 may be configured to receive and stabilize an endoscope 445 (within at least one of airway device 400 and ETT 410, in embodiments) while a distal tip 476 may be configured to affix to an ETT 410 via a universal adaptor (not depicted). When in use, a cam lock 477 may be switched between a "locked" and an "unlocked" position so that proximal portion 472 and distal portion 474 may slide along one another, effectively lengthening and shortening intubating pole 470.

Figure 20:
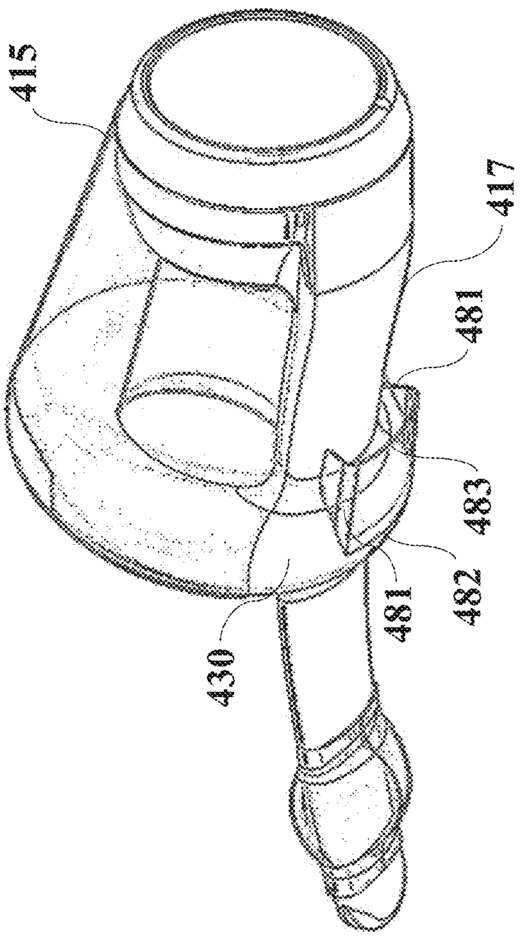
FIG. 20 displays a perspective view of a mask section of an airway device including a collection apparatus, as shown and described herein.

FIG. 20 displays a perspective view of a mask section 415 of an airway device 400 including a collection apparatus 480, as shown and described herein. Collection apparatus 480 may be utilized to collect and assist in evacuating oronasal secretion from a patient 402. Airway device 400 may be similar to the airway device 400 mentioned previously and may additionally include a collection apparatus 480 attached to the posterior surface of the mask section 415/spine section 417 and the inflatable bladder 430. Collection apparatus 480 includes a thin walled, semi-rigid plastic that spans the entire posterior wall of inflatable bladder 430. Collection apparatus 480 may be configured to flare out in the inferior to superior direction via sealed sides 481 and inferior edge 482 to the open superior edge 483. Collection apparatus may be hermetically sealed (by means of adhesives, chemicals, heat, ultrasonic bonding, etc.), minus the opening edge 483, to the posterior surface of the spine section 417 and the inflatable bladder 430. Once the airway device 400 is properly positioned adjacent the laryngeal opening 510 of the patient 402, the collection apparatus 480 may be positioned below the patient's oronasal cavity in an open configuration so that oronasal secretion may be collected in the collection apparatus 480 instead of having the oronasal secretion travel near or into the laryngeal opening 510 of the patient 402, thus creating a more efficient working environment. A suction catheter (not depicted) may then be utilized to evacuate the oronasal secretion or blood from the collection apparatus 480. The suction catheter may be pre-installed on a wall of the overtube 405 or may be introduced along the pre-formed path (along the bottom of the airway device 400) after the airway device 400 is inserted into a patient 402.

Figure 22:
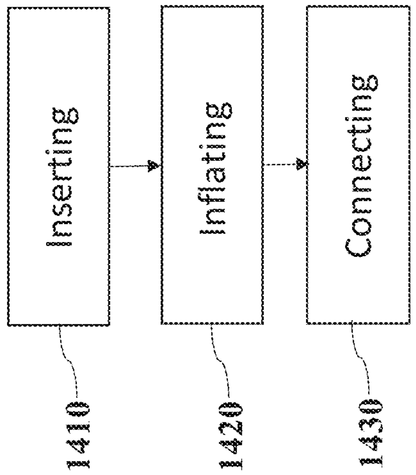
FIG. 22 displays a method for maintaining ventilation of a patient, as shown and described herein.

FIG. 22 displays a method 1400 for maintaining ventilation of a patient 402, as shown and described herein. Method 1400, unless otherwise noted, may utilize an airway device 400 similar to any of the embodiments of airway device 400 disclosed. Method 1400 includes inserting 1410 an airway device 400 into a throat 530 of a patient 402. An inflatable bladder 430 adapted to retract soft tissue adjacent a laryngeal opening 510 of the patient 402 to expose vocal cords and a trachea 520 of the patient 402 may then be inflated 1420 to form an airtight seal around the laryngeal opening 510 of the patient 402. Once the inflatable bladder 430 is inflated, the overtube 405 of the device 400 may then be connected 1430 to a ventilator (not depicted) that may deliver at least one of oxygen, air, and anesthetic to the patient 402.

Figure 23:
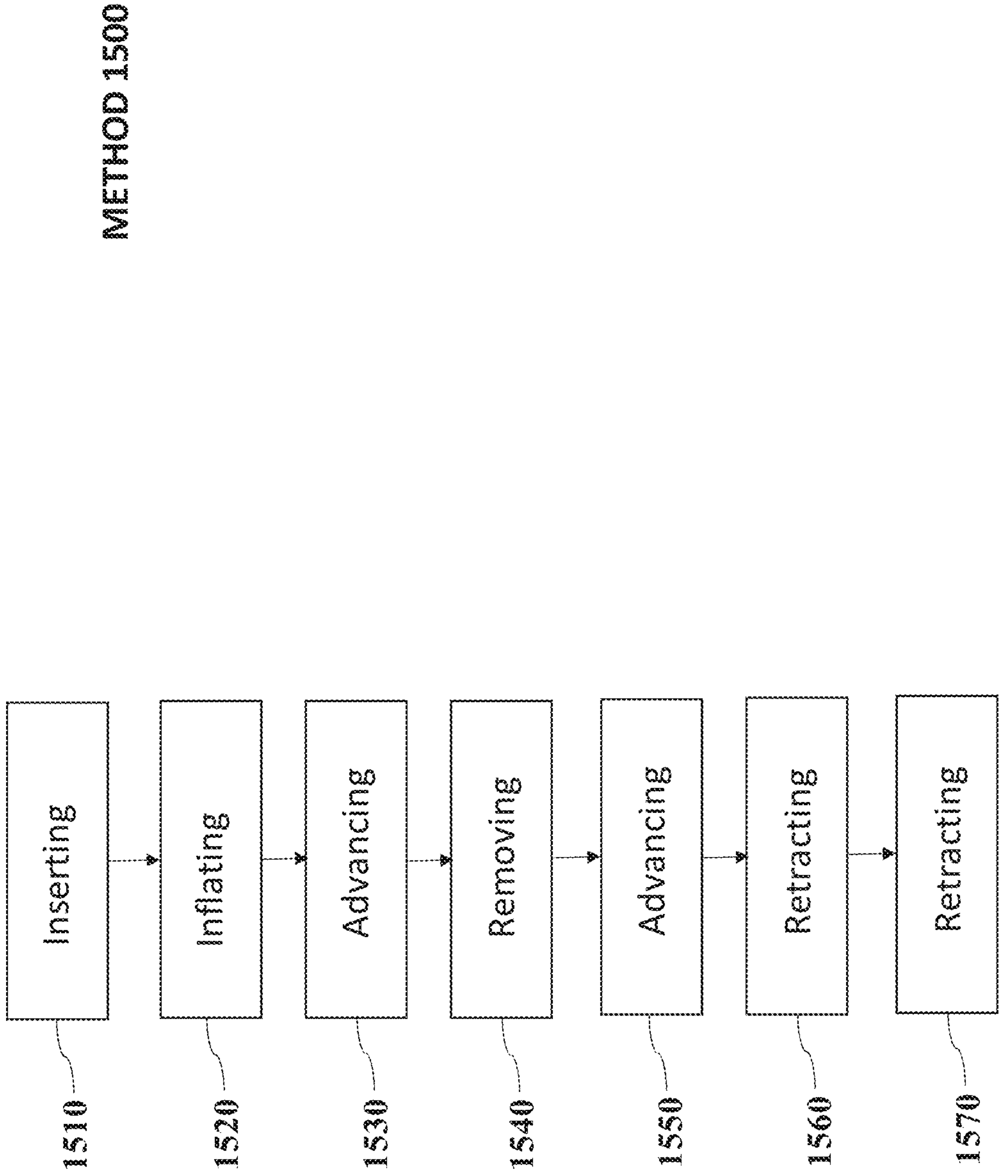
FIG. 23 displays a method for exchanging an ETT on an intubated patient, as shown and described herein.

FIG. 23 displays a method 1500 for exchanging an ETT 410 on an intubated patient 402, as shown and described herein. Method 1500, unless otherwise noted, may utilize an airway device 400 similar to any of the embodiments of airway device 400 disclosed. Method 1500 includes inserting 1510 the airway device 400 over an inserted/preexisting ETT 410 into a throat 530 of a patient 402. Once inserted 1510, an inflatable bladder 430 adapted to retract soft tissue adjacent a laryngeal opening 510 of the patient 402 to expose vocal cords and a trachea 520 of the patient 402 is inflated 1520 to form an airtight seal around a laryngeal opening 510 of the patient 402. An endoscope 445 may then be advanced 1530 through a mask section 415 of the airway device 400 and into the trachea 520 of the patient 402. Once the endoscope 445 is advanced 1530 and properly positioned, the preexisting ETT 410 may then be removed 1540 and a new ETT 410 may be advanced 1550 along the endoscope 445 and into the trachea 520 of the patient 402. At this point, the overtube 405 may be retracted 1560 until the airway device 400 is fully removed from the throat 530 and mouth 540 of the patient 402. Subsequently, the endoscope 445 is then retracted 1570 until the endoscope 445 is fully removed from the throat 530 of the patient 402.

Figure 24:
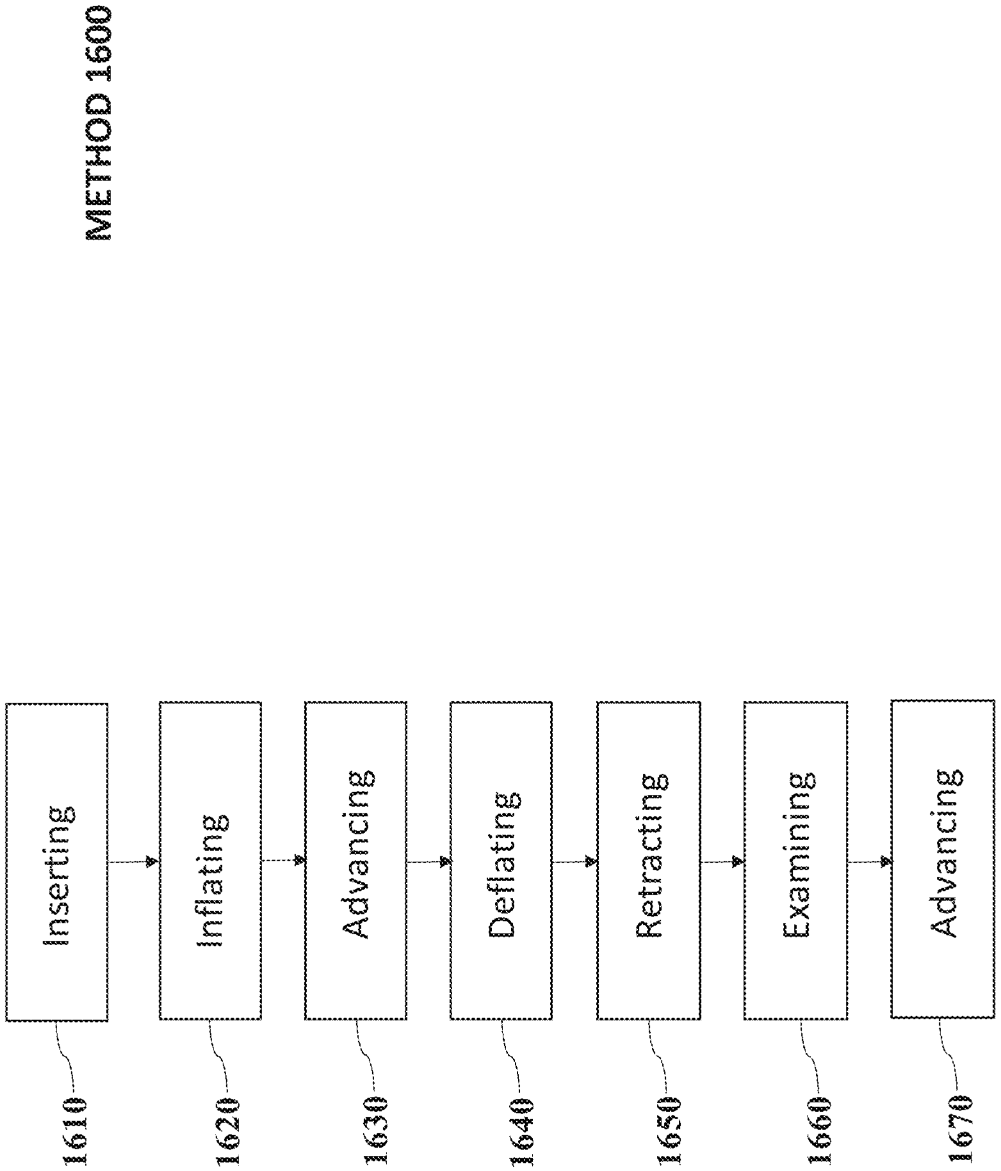
FIG. 24 displays a method for examining at least one of the larynx and trachea of an intubated patient, as shown and described herein.

FIG. 24 displays a method 1600 for examining at least one of the larynx and trachea 520 of an intubated patient 402, as shown and described herein. Method 1600, unless otherwise noted, may utilize an airway device 400 similar to any of the embodiments of device 400 disclosed. Method 1600 includes inserting 1610 the airway device 400 over an inserted/preexisting ETT 410 into a throat 530 of a patient 402. Once inserted 1610, an inflatable bladder 430 adapted to retract soft tissue adjacent a laryngeal opening 510 of the patient 402 to expose vocal cords and a trachea 520 of the device 400 is inflated 1620 to form an airtight seal around a laryngeal opening 510 of the patient 402. An endoscope 445 may then be advanced 1630 through a mask section 415 of the airway device 400 and into the trachea 520 of the patient 402. Once the endoscope 445 is advanced 1630 and properly positioned, the inflatable bladder 430 may be deflated 1640 and the preexisting ETT 410 may then be retracted 1650 proximal to the larynx. At this point, the larynx and/or trachea 520 may then be examined 1660 and subsequently at least one of a new ETT 410 and the preexisting ETT 410 may then be advanced 1670 back into the airway device 400.

Figure 25:
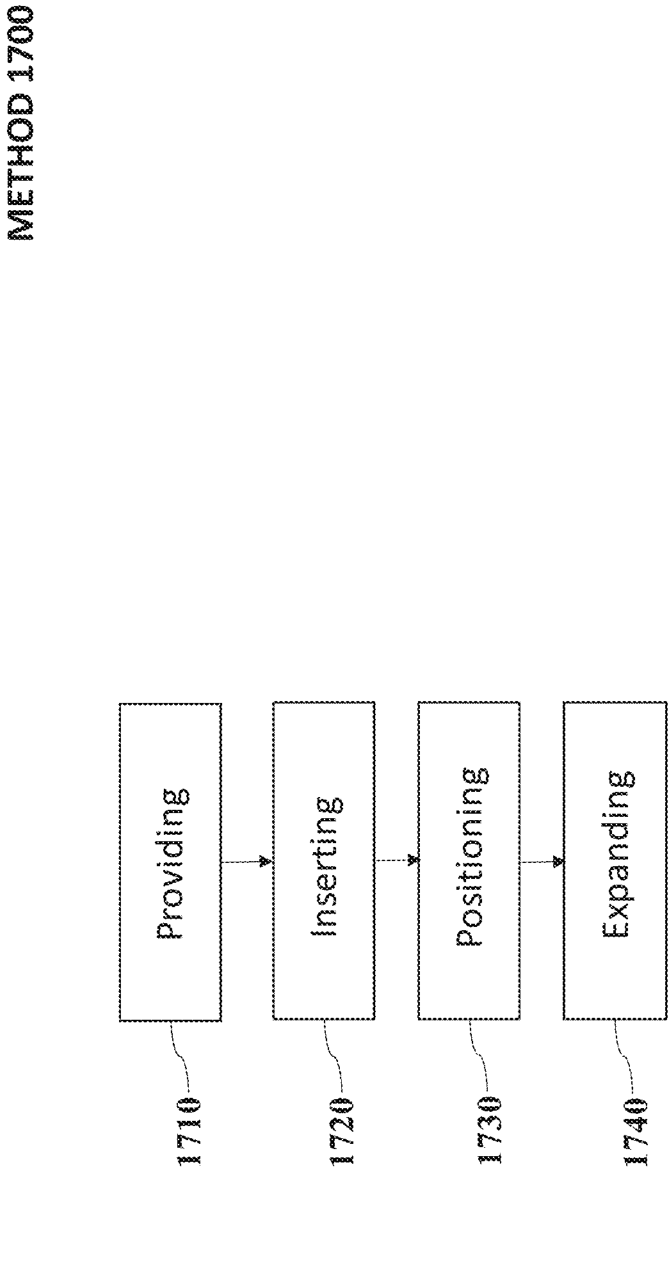
FIG. 25 displays a method for clearing the soft tissue from the larynx and hypopharynx of a patient, as shown and described herein.

FIG. 25 displays a method 1700 for clearing the soft tissue from the larynx and hypopharynx of a patient 402. Inflatable bladder 430 utilized in method 1700 may be configured, when inflated, to generate a displacement force to radially displace soft tissue from a hypopharyngeal lumen of a patient 402 toward a periphery of the hypopharyngeal lumen and clear the passage to the laryngeal opening 510 and the trachea 520 of the patient 402. Method 1700 includes providing 1710 an airway device 400 similar to that mentioned above and includes an expandable, torus-shaped bladder (inflatable bladder 430) attached to the mask section 417 in its transverse axis. The airway device 400 is inserted 1720 into the patient 402 and subsequently positioned 1730 so that inflatable bladder 430 is adjacent the larynx and hypopharynx of the patient 402. Once inserted 1720 into the patient 402, the inflatable bladder 430 is expanded 1740 and becomes rigid while expanding in a radial manner. As this occurs, soft tissue is pushed away from the center of the hypopharynx into the periphery, clearing the pathway to the laryngeal opening 510 and the trachea 520 of the patient 402.

Figure 26:
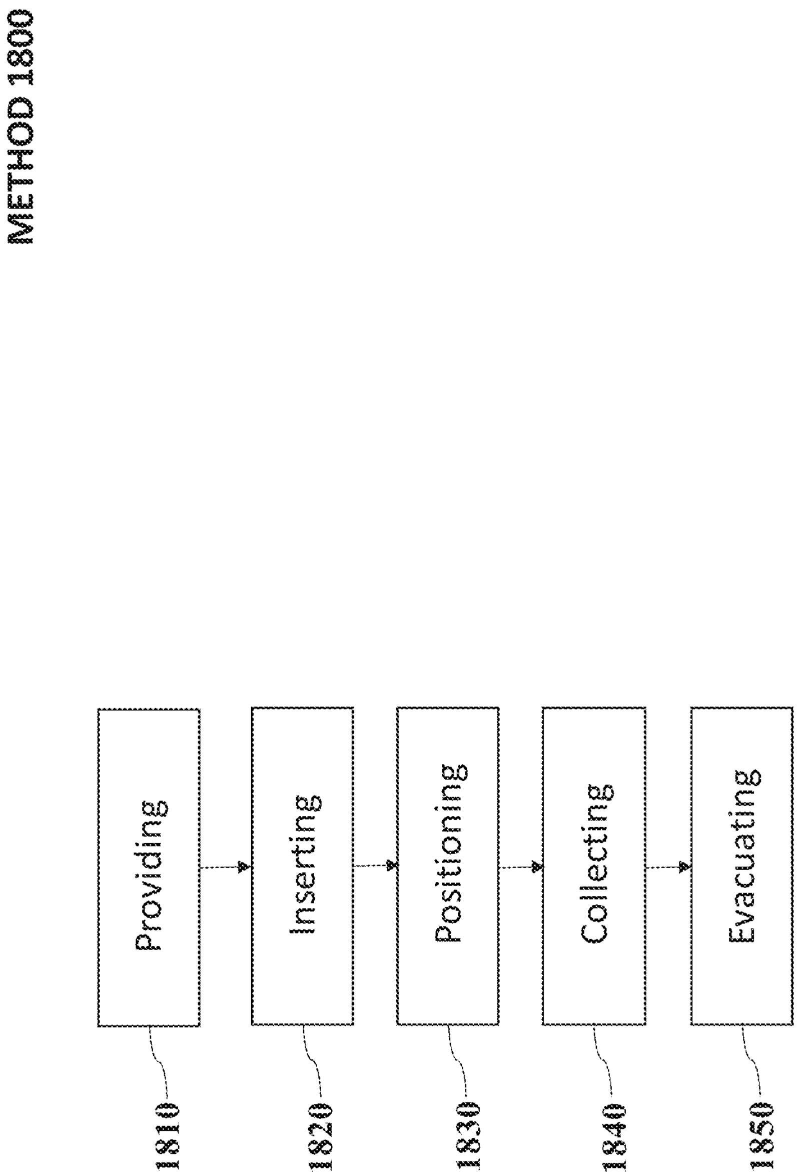
FIG. 26 displays a method for collecting and evacuating oronasal secretion from a patient, as shown and described herein.

FIG. 26 displays a method 1800 for collecting and evacuating oronasal secretion from a patient 402. The method 1800 includes providing 1810 and inserting 1820 an airway device 400 that is equipped with a collection apparatus 480 into a patient 402. The airway device 400 provided may be similar to the airway device 400 mentioned above and additionally includes a collection apparatus 480 attached to the posterior surface of the mask section 115/spine section 117 and the inflatable bladder 430. Collection apparatus 480 includes a thin walled, semi-rigid plastic that spans the entire posterior wall of the inflatable bladder 430. The collection apparatus 480 is configured to flare out in the inferior to superior direction via the sealed sides 481 and inferior edge 482 to the open superior edge 483. The collection apparatus 480 may be hermetically sealed (by means of adhesives, chemicals, heat, welding, etc.), minus the opening edge 483, to the posterior surface of the spine section 417 and the inflatable bladder 430. Once the airway device 400 is properly positioned adjacent the laryngeal opening 510 of the patient 402, the collection apparatus 480 may be positioned 1830 below the patient's oronasal cavity in an open configuration so that oronasal secretion may be collected 1840 in the collection apparatus 480 instead of having the oronasal secretion travel near or into the laryngeal opening 510 of the patient 402, thus creating a more efficient working environment. A suction catheter (not depicted) may then be utilized to evacuate 1850 the oronasal secretion or blood from the collection apparatus 480. The suction catheter may be pre-installed on a wall of the overtube 405 or may be introduced along the pre-formed path (along the bottom of the airway device 400) after the airway device 400 is inserted into a patient 402.

In embodiments, the suction catheter may be configured to be at least one of: preinstalled on a wall of an overtube 405 and introduced along a pre-formed path of the airway device 400 after the inserting 1820.

Figure 27:
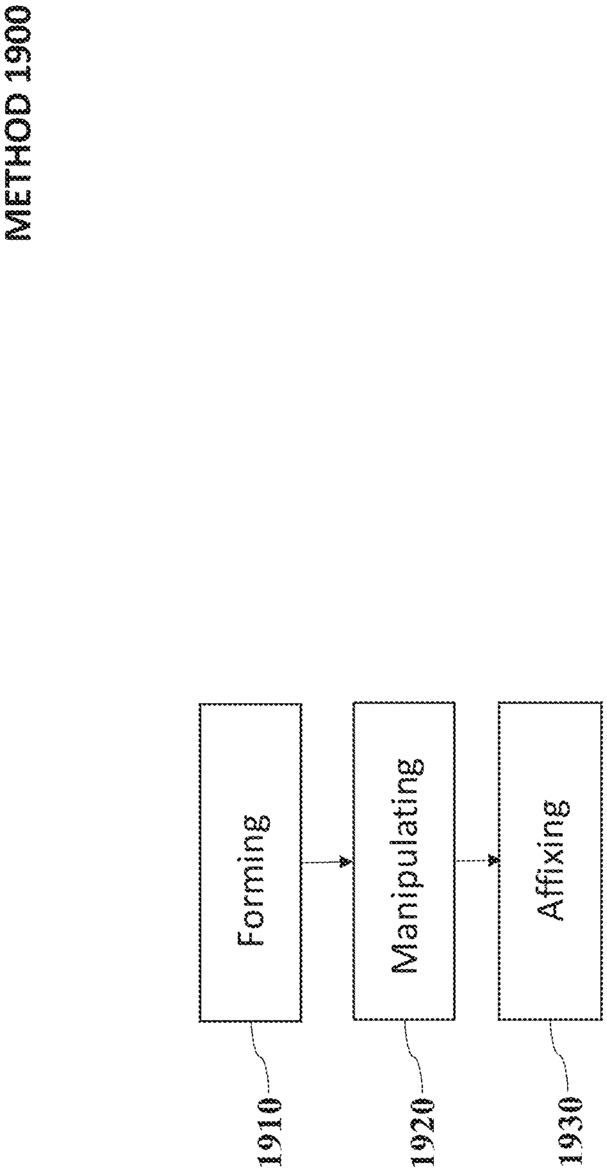
FIG. 27 displays a method for producing an airway device, as shown and described herein.

FIG. 27 displays a method 1900 for producing an airway device 400, as shown and described herein. The airway device 400 may include a structure similar to the airway device 400 mentioned previously and may enhance facility with which it can be introduced into a patient 402. Method 1900 includes forming 1910 a spine section 417 as a thin strip that may embody a length ranging from 50 millimeters to 120 millimeters, a width ranging from 5 millimeters to 20 millimeters, and a thickness ranging from 1 millimeter to 10 millimeters. Spine section may then be manipulated 1920 so that a convexity (with a radius ranging from 100 millimeters to 500 millimeters) is formed along the bottom side of the spine section 417 (the convex surface may face anteriorly). Once formed, spine section 417 may then be affixed 1930 to a mask section 415 (similar to that described above in relation to the airway device 400) so that the spine section 417 spans the entire length of the mask section 415 and the additional length of the spine section 417 forms an esophageal obturator 435 (including an esophageal obturator cuff 440). The configuration of the spine section 417 embodying the dorsal convexity may lessen the mask section's 415 tendency to move anteroinferiorly toward the larynx and encourage the mask section 415 to advance (preferably) in the inferior direction into the hypopharynx/proximal esophagus of the patient 402.

In embodiments, inflatable bladder 430 and esophageal obturator cuff 440 may each comprise at least one of the following materials: polyethylene teraphthalate (PET/PETP), low-density polyethylene (LDPE), polyvinyl chloride (PVC), silicone, neoprene, polyisoprene, and polyurethane (PU). In further embodiments, at least one of inflatable bladder 430 and esophageal obturator cuff 440 may be formed via blow molding.

In embodiments, esophageal obturator cuff 440 may be positioned over a distal end of one of a plurality of inflating tubes 437, 438, 439 (each affixed to an air supply) located at the distal end 436 of the esophageal obturator 435 so that esophageal obturator cuff 440 may be inflated. In further embodiments, esophageal obturator cuff 440 may be hermetically sealed via means including, but not limited to, adhesives, chemicals, welding, and heat.

In embodiments, one or more of the plurality of inflating tubes 437, 438, 439 may be integrated with the body of inflatable bladder 430. In further embodiments, at least one of the plurality of inflating tubes 437, 438, 439 may be integrated with expandable body 420.

In embodiments, the inflatable bladder 430 and the esophageal obturator cuff 440 may each comprise a wall thickness ranging between 5 micrometers and 100 micrometers and a safe pressure level range ranging from 0.1 PSI to 2 PSI.

In embodiments, inflatable bladder 430 may be affixed to a mid-portion of the spine section 417 with a longitudinal axis of the inflatable bladder 430 parallel with a transverse axis of the patient 402 and a "tire plane" rotated between 1 degree and 45 degrees.

In embodiments, inflatable bladder 430 may be affixed to spine section 417 via at least one of adhesives, chemicals, welding, and heat.

In embodiments, inflatable bladder 430 may be constructed as at least one of: abutting at least one of an anterior surface and a posterior surface of spine section 417, centering within a body of spine section 417 with anterior and posterior portions of the spine encircling inflatable bladder 430, and encircling spine section 417 so that spine section 417 runs through inflatable bladder 430.

In embodiments, sheath 425 may comprise a plurality of thin sheets of material each of a similar material and each sheet of material ranging in thickness from 5 micrometers to 500 micrometers. The plurality of thin sheets may be formed into a tubular structure and may be hermetically attached, by means of at least one of adhesives, chemicals, welding, and heat, to the inlet portion 426 superiorly, the inflatable bladder 430 inferiorly, and the spine section 417 posteriorly.

In embodiments, each of the spine section 417 and the overtube 405 may comprise a semirigid material. In embodiments, each of the spine section 417 and the overtube 405 may comprise a material selected from the group consisting of: polyethylene teraphthalate (PET/PETP), low-density polyethylene (LDPE), polyvinyl chloride (PVC), silicone, neoprene, polyisoprene, and polyurethane (PU). In further embodiments, each of the spine section 417 and the overtube 405 may comprise a Shore A hardness ranging between 20 and 90 on the Shore A hardness scale.

In embodiments, the inlet portion 426 and the spine section 417 may be constructed as a contiguous piece. This contiguous construction may, in embodiments, may be formed via injection molding. In further embodiments, inlet portion 426 may be configured to fit over and affix to the distal end 414 (or tip) of overtube 405 by means including at least one of adhesives, chemicals, welding, and heat.

It is noted that in embodiments, esophageal obturator 135 may be integral with spine section 117.

It is noted that in embodiments, any of the applicable steps of retracting 1370, 1560, 1650 airway device 400 out of the patient 402 without dislodging the ETT 410 may be carried out in a plurality of ways. One way to remove airway device 400 includes utilizing an endotracheal tube holder/ETT holder to assist in the removal.

In embodiments, various attachment and fitting techniques and equipment (male-female engagement, fastening means, magnets, welding, adhesives, bonding, etc.) may be utilized in any of the disclosed embodiments in order for components of the embodiments to properly attach themselves to and/or efficiently position themselves with one another and so that the airway device 400 can efficiently and/or properly function. As an example, the mask section 415 of airway device 400 may include inflatable bladder 430 that may be heat bonded to the body 420 of mask section 415, as opposed to an inflatable bladder 130 affixed to body 420 via fasteners.

For the purposes of this disclosure, the terms "laryngeal inlet" and "laryngeal opening" may be synonymous.

For the purposes of this disclosure, the terms "hood body" and "mask section" may be synonymous.

For the purposes of this disclosure, the terms "endotracheal tube" and "ETT" may be synonymous. In certain embodiments, an "ETT" may be a device for intubating a patient or individual other than an endotracheal tube.

For the purposes of this disclosure, the terms "obturator" and "obdurator" may be synonymous.

For the purposes of this disclosure, the terms "bladder", "inflating bladder", and "inflatable bladder" may be synonymous. It is further noted that each of the terms "bladder", "inflating bladder", and "inflatable bladder" may be used to refer to any disclosed embodiment of a bladder found in airway device 400 and/or intubation device 110.

For the purposes of this disclosure, the term "medially affixed" may refer to an element of the disclosure being connected to at least one other object at or around its midpoint or middle point.

For the purposes of this disclosure, the term "retroverted", in relation to spine section 417, may refer to the convex nature of the spine section 417 wherein the spine section along its entire length assumes a gentle curve with the convexity facing in the anterior direction.

For the purposes of this disclosure, the position and configuration of the inflating bladder/inflatable bladder may be described using the terminology and the coordinate system as defined in the Standard Automotive Engineering (SAE) J670.

A plurality of additional features and feature refinements are applicable to specific embodiments. These additional features and feature refinements may be used individually or in any combination. It is noted that each of the following features discussed may be, but are not necessary to be, used with any other feature or combination of features of any of the embodiments presented herein.

Unless otherwise defined, all technical and scientific terms used herein have the same meanings as are commonly understood by one of ordinary skill in the art to which this disclosure belongs. Although methods similar or equivalent to those described herein can be used in the practice or testing of the present disclosure, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present disclosure is not limited to what has been particularly shown and described hereinabove. Rather, the scope of the present disclosure is defined by the appended claims and includes both combinations and sub-combinations of the various features described hereinabove as well as variations and modifications thereof, which would occur to persons skilled in the art upon reading the foregoing description.

I claim:

1. An airway device, comprising:

an overtube having a proximal end and a distal end;

a mask section attached to the distal end of the overtube, the mask section including:

a spine section comprising an esophageal obturator protruding from a distal end of the spine section; and an expandable body disposed on a proximal portion of the spine section, the expandable body including:

an inlet portion disposed adjacent the overtube;

an inflatable bladder anchored to the spine section a distance from the inlet portion;

a sheath spanning along the spine section from the inlet portion to the inflatable bladder; and a tunnel section disposed within the sheath and extending from the inlet portion to the inflatable bladder; and wherein the mask section is configured for radially retracting soft tissue away from the laryngeal opening to create an unobstructed path into the trachea of the patient and sealing engagement with a laryngeal opening of the patient;

and wherein the esophageal obturator further comprises an inflatable esophageal obturator cuff affixed to a distal end of the esophageal obturator.

2. The device of claim 1, wherein the inlet portion and the spine section are constructed as a contiguous piece.

3. The device of claim 1, wherein the tunnel section and the sheath are affixed to the inlet portion proximally and to the inflatable bladder distally and forms an airtight seal between the inlet portion and the inflatable bladder.

4. The device of claim 1, wherein the inflatable bladder comprises a torus-shaped expandable body.

5. The device of claim 1, wherein the inflatable bladder is positioned at a fixed, negative inclination angle in the range of 15 to 35 degrees orthogonal from an anchor point of inflatable bladder, the fixed angle configured to provide increased adaptability to aryepiglottic folds of the patient.

6. The device of claim 1, wherein a first portion of the inflatable bladder comprises substantially a portion of the body of the inflatable bladder anterior to its attachment to the spine section and at least one of a circular cross-section and an elliptical cross-section and a second portion of the inflatable bladder comprises substantially a portion of the body of the inflatable bladder posterior to its attachment to the spine section and a curvilinear cross-section.

7. The device of claim 1, wherein the spine section comprises a retroverted configuration configured to effectively engage the patient's hypopharynx/proximal esophagus.

8. The device of claim 7, wherein the airway device is configured to effectively engage the patient's hypopharynx/proximal esophagus, via lodging of the esophageal obturator and the inflated Inflatable esophageal obturator cuff of the spine section to the patient's hypopharynx/proximal esophagus.

9. The device of claim 8, further comprising a plurality of inflating tubes, each of the inflating tubes configured to inflate a respective one of the inflatable bladder, the inflatable esophageal obturator cuff, and the sheath.

10. A method for clearing soft tissue from a larynx and a hypopharynx of a patient, comprising:

inserting an airway device into a throat of the patient, the airway device including:

an overtube having a proximal end and a distal end;

a mask section attached to the distal end of the overtube, the mask section including a spine section and an expandable body disposed on a proximal portion of the spine section, the expandable body including:

an inlet portion disposed adjacent the overtube; and an inflatable bladder anchored to the spine section a distance from the inlet portion;

a sheath spanning along the spine section from the inlet portion to the inflatable bladder; and a tunnel section disposed within the sheath and extending from the inlet portion to the inflatable bladder;

inflating the inflatable bladder to form an airtight seal around a laryngeal opening of the patient, wherein the inflatable bladder is adapted to retract soft tissue adjacent the laryngeal opening of the patient to expose vocal cords and a trachea of the patient.

11. The method of claim 10, wherein the inflatable bladder is configured, when inflated, to generate a displacement force to radially displace soft tissue from a hypopharyngeal lumen toward a periphery of the hypopharyngeal lumen and clear the passage to the laryngeal opening and the trachea of the patient.

12. A method for intubating a patient, the method comprising:

inserting an airway device into a throat of the patient, the airway device including:

an overtube having a proximal end and a distal end;

a mask section attached to the distal end of the overtube, the mask section including a spine section and an expandable body disposed on a proximal portion of the spine section, the expandable body including:

an inlet portion disposed adjacent the overtube; and an inflatable bladder anchored to the spine section a distance from the inlet portion;

a sheath spanning along the spine section from the inlet portion to the inflatable bladder; and a tunnel section disposed within the sheath and extending from the inlet portion to the inflatable bladder;

inflating the inflatable bladder to form an airtight seal around a laryngeal opening of the patient, wherein the inflatable bladder is adapted to retract soft tissue adjacent the laryngeal opening of the patient to expose vocal cords and a trachea of the patient;

advancing an endoscope through the mask section of the airway device and into the trachea of the patient;

advancing an ETT over the endoscope and into the trachea of the patient;

retracting the overtube from the throat of the patient until the overtube is fully removed from the throat and mouth of the patient; and retracting the endoscope from the throat of the patient until the endoscope is fully removed from the throat and the mouth of the patient.

13. The method of claim 12, further comprising continuously providing ventilation to the patient starting at the inflating.

14. The method of claim 12, further comprising confirming the ETT is at least partially positioned within the trachea of the patient via the endoscope.

15. A mask section for an airway device, comprising:

a spine section and an expandable body disposed on a proximal portion of the spine section, the expandable body including:

an inlet portion disposed on a proximal end of the spine section and forming a contiguous structure with the spine section;

an inflatable bladder anchored to the spine section a distance from the inlet portion;

a sheath spanning along the spine section from the inlet portion to the inflatable bladder; and a tunnel section disposed within the sheath and extending from the inlet portion to the inflatable bladder;

and wherein the inflatable bladder is configured for sealing engagement with a laryngeal opening of a patient to create an unobstructed path into the trachea of the patient.

16. The mask section of claim 15, wherein the tunnel section is proximally affixed to the inlet portion and distally affixed to the inflatable bladder, further wherein the tunnel section forms an airtight seal between the inlet portion and the inflatable bladder.

17. A method for exchanging the endotracheal tube of an intubated patient, the method comprising:

inserting an airway device, over a preexisting endotracheal tube, into a throat of the patient, the airway device including:

an overtube having a proximal end and a distal end;

a mask section disposed on the distal end of the overtube, the mask section including: a spine section and an expandable body disposed on a proximal portion of the spine section, the expandable body including:

an inlet portion disposed on a proximal end of the spine section and forming a contiguous structure with the spine section;

an inflatable bladder anchored to the spine section a distance from the inlet portion;

a sheath spanning along the spine section from the inlet portion to the inflatable bladder; and a tunnel section disposed within the sheath and extending from the inlet portion to the inflatable bladder;

inflating the inflatable bladder to form an airtight seal around a laryngeal opening of the patient, wherein the inflatable bladder is adapted to retract soft tissue adjacent the laryngeal opening of the patient to expose vocal cords and a trachea of the patient;

advancing an endoscope through the mask section of the airway device and into the trachea of the patient;

removing the preexisting endotracheal tube;

advancing a new endotracheal tube along the endoscope and into the trachea of the patient;

retracting the overtube from the throat of the patient until the overtube is fully removed from the throat and mouth of the patient; and retracting the endoscope from the throat of the patient until the endoscope is fully removed from the throat and mouth of the patient.

18. A method for examining the larynx and trachea of an intubated patient, the method comprising:

inserting an airway device into a throat of the patient, the airway device including:

an overtube having a proximal end and a distal end;

a mask section disposed on the distal end of the overtube, the mask section including:

a spine section comprising an esophageal cuff protruding from a distal end of the spine section; and an expandable body disposed on a proximal portion of the spine section, the expandable body including:

an inlet portion disposed adjacent the overtube;

an inflatable bladder anchored to the spine section a distance from the inlet portion;

a sheath spanning along the spine from the inlet portion to the inflatable bladder; and a tunnel section disposed within the sheath and extending from the inlet portion to the inflatable bladder;

inflating the inflatable bladder to form an airtight seal around a laryngeal opening of the patient, wherein the inflatable bladder is adapted to retract soft tissue adjacent the laryngeal opening of the patient to expose vocal cords and a trachea of the patient;

inflating the esophageal cuff to secure the device in the patient and prevent gastric reflux;

advancing an endoscope through the mask section of the airway device and into the trachea of the patient;

deflating the esophageal cuff;

retracting a preexisting endotracheal tube proximal to the larynx;

examining and evaluating the larynx and trachea; and performing at least one of: advancing a new endotracheal tube and removing the preexisting endotracheal tube.

19. A method for collecting and evacuating oronasal secretion from a patient, comprising:

inserting an airway device into a throat of the patient, the device including:

an overtube having a proximal end and a distal end;

a mask section disposed on the distal end of the overtube, the mask section including:

a spine section and an expandable body disposed on a proximal portion of the spine section, the expandable body including:

an inlet portion disposed on a proximal end of the spine section and forming a contiguous structure with the spine section;

an inflatable bladder anchored to the spine section a distance from the inlet portion;

a sheath spanning along the spine section from the inlet portion to the inflatable bladder; and a tunnel section disposed within the sheath and extending from the inlet portion to the inflatable bladder; and a collection apparatus affixed to a posterior surface of each of the mask section and the inflating bladder;

positioning the airway device adjacent a laryngeal opening of the patient;

and positioning the collection apparatus in the patient's hypopharynx in an open configuration so that oronasal secretion is collected in the collection apparatus.

20. The method of claim 19, wherein the collection apparatus comprises a thin walled, semi-rigid plastic that spans an entire posterior wall of the inflatable bladder.

21. The method of claim 19, wherein the collection apparatus is configured to flare out in the inferior to superior direction in regards to the sealed sides and inferior edge, and the open superior edge.

22. The method of claim 19, wherein the collection apparatus is hermetically sealed to the posterior surface and the inflatable bladder via at least one of adhesives, chemicals, welding, and heat.

23. The method of claim 19, further comprising evacuating at least one of oronasal secretion and blood out of the collection apparatus via a suction catheter.

24. The method of claim 23, wherein the suction catheter is configured to be at least one of: preinstalled on an overtube wall and introduced along a pre-formed path of the device after insertion.

* * * * *